US012692271B2

(12) United States Patent
Cecere et al.

(10) Patent No.: US 12,692,271 B2
(45) Date of Patent: *Jul. 28, 2026

(54) SUBSTITUTED BENZO[f][1,2,4]TRIAZOLO [4,3-a][1,4]DIAZEPINES AS GABA A GAMMA1 POSITIVE ALLOSTERIC MODULATORS

(71) Applicant: Hoffmann-La Roche Inc., Little Falls, NJ (US)

(72) Inventors: Giuseppe Cecere, Basel (CH); Jaclyn Ivy Wamsteeker Cusulin, Muttenz (CH); Nicolas Zorn, Durmenach (FR); Luca Gobbi, Basel (CH); Maria-Clemencia Hernandez, Delémont (CH); Frédéric Knoflach, Arlesheim (CH); Andreas Koblet, Bottmingen (CH); Eoin Cornelius O'Connor, Basel (CH); Andres Miguel Olivares Morales, Binningen (CH); Michael Reutlinger, Freiburg (DE); Valerie Runtz-Schmitt, Rixheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/355,538

(22) Filed: Jul. 20, 2023

(65) Prior Publication Data

US 2024/0002393 A1 Jan. 4, 2024

Related U.S. Application Data

(63) Continuation of application No. 17/217,687, filed on Mar. 30, 2021, now Pat. No. 11,739,095.

(30) Foreign Application Priority Data

Mar. 31, 2020 (EP) .................................... 20167239

(51) Int. Cl.
*C07D 487/12* (2006.01)
*C07D 487/04* (2006.01)

(52) U.S. Cl.
CPC .................................. *C07D 487/04* (2013.01)

(58) Field of Classification Search
CPC .................................................... C07D 487/12
USPC .......................................................... 540/578
See application file for complete search history.

(56) References Cited

U.S. PATENT DOCUMENTS

| | | | |
|---|---|---|---|
| 3,681,343 | A | 8/1972 | Hester, Jr. |
| 3,734,922 | A | 5/1973 | Hester, Jr. |
| 3,927,016 | A | 12/1975 | Hester, Jr. et al. |
| 3,987,052 | A | 10/1976 | Hester, Jr. |
| 4,201,712 | A | 5/1980 | Weber et al. |
| 4,621,083 | A | 11/1986 | Weber et al. |
| 5,185,442 | A | 2/1993 | Weber et al. |
| 5,532,233 | A | 7/1996 | Weber et al. |
| 10,259,815 | B2 | 4/2019 | Cook et al. |
| 11,739,095 | B2 | 8/2023 | Cecere et al. |
| 12,344,614 | B2 | 7/2025 | Bartels et al. |
| 12,365,687 | B2 | 7/2025 | Bartels et al. |
| 2012/0295892 | A1 | 11/2012 | Cook et al. |
| 2021/0309664 | A1 | 10/2021 | Cecere et al. |
| 2022/0324867 | A1 | 10/2022 | Ke et al. |
| 2023/0109111 | A1 | 4/2023 | Cecere et al. |
| 2023/0136326 | A1 | 5/2023 | Bartels et al. |
| 2023/0141603 | A1 | 5/2023 | Cecere et al. |
| 2023/0142171 | A1 | 5/2023 | Bartels et al. |
| 2024/0002393 | A1 | 1/2024 | Cecere et al. |
| 2024/0190889 | A1 | 6/2024 | Cecere et al. |
| 2024/0270744 | A1 | 8/2024 | Cecere et al. |
| 2024/0287082 | A1 | 8/2024 | Cecere et al. |
| 2024/0294543 | A1 | 9/2024 | Bartels et al. |

(Continued)

FOREIGN PATENT DOCUMENTS

| | | | |
|---|---|---|---|
| AT | 328458 | B | 3/1976 |
| CH | 551993 | A | 7/1974 |

(Continued)

OTHER PUBLICATIONS

Forkuo, G., et al., "Alleviation of Multiple Asthmatic Pathologic Features with Orally Available and Subtype Selective GABA A Receptor Modulators" Mol Pharm 14(6):2088-2098 (Jun. 5, 2017).

(Continued)

*Primary Examiner* — Douglas M Willis

(74) *Attorney, Agent, or Firm* — Morgan, Lewis & Bockius LLP

(57) ABSTRACT

Compounds having the general formula (I)

(I)

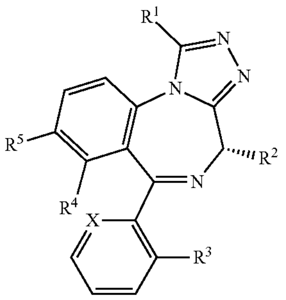

wherein $R^1$, $R^2$, $R^3$, $R^4$, $R^5$ and X are as described herein, compositions including the compounds and methods of using the compounds.

18 Claims, No Drawings

(56) References Cited

U.S. PATENT DOCUMENTS

| | | | |
|---|---|---|---|
| 2025/0049967 | A1 | 2/2025 | Cecere et al. |
| 2025/0388586 | A1 | 12/2025 | Bartels et al. |
| 2026/0008781 | A1 | 1/2026 | Bartels et al. |

FOREIGN PATENT DOCUMENTS

| | | | |
|---|---|---|---|
| CH | 567025 | A5 | 9/1975 |
| CH | 569018 | A5 | 11/1975 |
| CH | 569739 | A5 | 11/1975 |
| CH | 572057 | A5 | 1/1976 |
| CH | 574426 | A5 | 4/1976 |
| DE | 2215943 | A1 | 10/1972 |
| DE | 2234652 | A1 | 2/1973 |
| DE | 2304307 | A1 | 8/1973 |
| DE | 2525691 | A1 | 1/1976 |
| DE | 2533924 | A1 | 2/1977 |
| DE | 3724031 | A1 | 1/1988 |
| EP | 0176927 | A2 | 4/1986 |
| JP | S5283498 | A | 7/1977 |
| JP | S6187684 | A | 5/1986 |
| WO | WO9404537 | A2 | 3/1994 |
| WO | 03/082832 | A2 | 10/2003 |
| WO | WO2011042550 | A1 | 4/2011 |
| WO | 2015/200766 | A2 | 12/2015 |
| WO | 2018/035246 | | 2/2018 |
| WO | 2018/035246 | A1 | 2/2018 |
| WO | 2021/198124 | A1 | 10/2021 |
| WO | 2020/198275 | A1 | 10/2022 |
| WO | WO2023057415 | A1 | 4/2023 |

OTHER PUBLICATIONS

Hackam, D.G., et al., "Translation of research evidence from animals to humans" JAMA 296(14):1731-1732 (Oct. 11, 2006).

"International Search Report—PCT/EP2019/058063" (w/Written Opinion),:pp. 1-14 (Apr. 26, 2021).

Jordan, V.C., "Tamoxifen: A Most Unlikely Pioneering Medicine" Nat Rev Drug Discov 2(3):205-213 (Mar. 1, 2003).

Kolbah, D., et al., "Stereoselective in-vitro aromatic-ring oxygenations of chiral 1,4-benzodiazepin-2-ones" Helv Chim Acta 60(1):265-283 (Jan. 26, 1977).

Kooistra, T., et al., "Triazolobenzodiazepines: a new class of stimulators of tissue-type plasminogen activator synthesis in human endothelial cells" Biochem Pharmacol 46(1):61-67 (Jul. 6, 1993).

Lee, S., et al., "Axial chirality and affinity at the GABA(A) receptor of pyrimido [1,2-a][1,4]benzodiazepines and related compounds" Bioorg Med Chem 16(21):9519-9523 (Nov. 1, 2008).

Svetlov, S., et al., "The specific binding of the platelet-activating factor (PAF) receptor antagonist WEB 2086 and the benzodiazepine flunitrazepam to rat hepatocytes" Life Sci 58(5):PL81-PL86 (Dec. 1, 1995).

Waters, L. et al., "The use of a quantitative structure-activity relationship (QSAR) model to predict GABA-A receptor binding of newly emerging benzodiazepines" Sci Justice 58(5):219-225 (May 1, 2018).

Watjen, F., et al., "Novel benzodiazepine receptor partial agonists: oxadiazolylimidazobenzodiazepines" J Med Chem 32(10):2282-2291 (Jan. 1, 1989).

Ben-Cherif, W. et al., "Neuropharmacological screening of two 1,5-benzodiazepine compounds in mice," Comptes Rendus. Biologies, 2010, vol. 333(3), pp. 214-219.

Coghlan, S. et al., "GABA System Dysfunction in Autism and Related Disorders: From Synapse to Symptoms," Neuroscience & Biobehavioral Reviews, 2012, vol. 36(9), pp. 2044-2055.

Elgarf, A.A. et al., "Different Benzodiazepines Bind with Distinct Binding Modes to GABAA Receptors," ACS Chem. Biol., 2013, vol. 13(8), pp. 2033-2039.

Fiakpui et al., "Synthesis and Anticonvulsant Activities of 5-(2-Chlorophenyl)-7H-pyrido[4,3-f][1,2,4] triazolo [4,3-a][1,4] diazepines," Journal of Heterocyclic Chemistry, 1999, vol. 36(2), pp. 377-380.

Heckendorn, R. et al., "Structure and Reactivity of a Triazolobenzodiazepine/Oxalyl Chloride Adduct," Helvetica Chimica Acta, 1978, vol. 61(2), pp. 848-863.

Hou, L. et al., "Positron Emission Tomography Imaging of the Endocannabinoid System: Opportunities and Challenges in Radiotracer Development," Journal of Medicinal Chemistry, 2020, vol. 64(1), pp. 123-149.

Kassenbrock, A. et al., "Selected PET Radioligands for lon Channel Linked Neuroreceptor Imaging: Focus on GABA, NMDA and nACh Receptors," 2016, vol. 16(16), pp. 1830-1842.

Khanna, A. et al., "Limitations of current GABA agonists in neonatal seizures: toward GABA modulation via the targeting of neuronal Cl- transport," Frontiers in Neurology, 2013, vol. 4, Article 78.

Maas, A. I. R. et al., "Traumatic brain injury: progress and challenges in prevention, clinical care, and research," Lancet Neurology Commissions, 2022, vol. 21(11), pp. 1104-1160.

Mitsika, E. E. et al., "Optimized Photo-Fenton degradation of psychoactive pharmaceuticals alprazolam and diazepam using a chemometric approach—Structure and toxicity of transformation products," Journal of Hazardous Materials, 2021, vol. 403, Article 123819.

Nasrallah, I. et al., "An Overview of PET Neuroimaging," Seminars in Nuclear Medicine, 2013, vol. 43(6), pp. 449-461.

Sobańska, A. W. et al., "Comparative (Q)SAR analysis of benzodiazepine derivatives with different biological activity," European Journal of Medicinal Chemistry, 2015, vol. 89, pp. 147-155.

Sudhakar, S. K., "Are GABAergic drugs beneficial in providing neuroprotection after traumatic brain injuries? A comprehensive literature review of preclinical studies," Frontiers in Neurology, 2023, vol. 14, Article 1109406.

WebMD. (Jun. 1, 2022). Fragile X syndrome: Symptoms, causes, diagnosis, and treatment. WebMD. https://www.webmd.com/children/what-is-fragile-x-syndrome (Year: 2022).

SUBSTITUTED BENZO[f][1,2,4]TRIAZOLO[4,3-a][1,4]DIAZEPINES AS GABA A GAMMA1 POSITIVE ALLOSTERIC MODULATORS

CROSS-REFERENCE TO RELATED APPLICATIONS

This application is a continuation of U.S. application Ser. No. 17/217,687 filed on Mar. 30, 2021, which is entitled to the benefit of European Application No. EP20167239.1 filed on Mar. 31, 2020, the disclosures of which are incorporated herein by reference.

BACKGROUND OF THE INVENTION

Receptors for the major inhibitory neurotransmitter, gamma-aminobutyric acid (GABA), are divided into two main classes: (1) $GABA_A$ receptors, which are members of the ligand-gated ion channel superfamily and (2) $GABA_B$ receptors, which are members of the G-protein linked receptor family. The $GABA_A$ receptor complex which is a membrane-bound heteropentameric protein polymer is composed principally of α, β and γ subunits. $GABA_A$ receptors are ligand-gated chloride channels and the principal mediators of inhibitory neurotransmission in the human brain.

There are 19 genes encoding for $GABA_A$ receptor subunits that assemble as pentamers with the most common stoichiometry being two α, two β and one γ subunit. $GABA_A$ subunit combinations give rise to functional, circuit, and behavioral specificity (Sieghart, 2006; Vithlani et al., 2011). $GABA_A$ receptors containing the γ1 subunit ($GABA_A$ γ1) are of particular interest due to their enriched expression in the limbic system (Seeburg et al., 1990; Pirker et al., 2000; Esmaeili et al., 2008; Durisic et al., 2017; Sequeira et al., 2019) and unique physiological and pharmacological properties (Mohler et al., 1996; Wingrove et al., 1997; Sieghart et al., 2005). The $GABA_A$ γ1 subunit-containing receptors, while less abundant (around 5-10% of total expression of $GABA_A$ receptors in the brain) than γ2 subunit-containing receptors exhibit an enriched brain mRNA and protein distribution in key brain areas such as extended amygdala (central, medial, and bed nucleus of the stria terminalis), lateral septum, hypothalamus, and pallidum/nigra. These structures form the interconnected core of a subcortical limbic circuit regulating motivated social and affective behaviors. In abnormal or disease conditions, hyper-recruitment of this circuit promotes anxiety, arousal, aggression, fear and defense while inhibiting foraging and social interactions (Goossens et al., 2007; Hofmann et al., 2011; Fox et al., 2012; Martin-Santos et al., 2014; Anderson et al., 2014; Calhoon et al., 2015).

Hyperactivity in limbic cortical regions (known to form a coordinated functional network with extended amygdala/hypothalamus regions) which are key areas for processing of social and emotionally relevant stimuli, is the common hallmark of a variety of psychiatric, neurological, neurodevelopmental, neurodegenerative, mood, motivational and metabolic disorders. In such a disease state, and given the characteristic anatomical distribution of the γ1 subunit-containing $GABA_A$ receptors, a $GABA_A$ γ1 positive allosteric modulator (PAM) may be an effective treatment as a symptomatic or disease-modifying agent.

Multiple lines of evidence suggest that an imbalance between excitatory/inhibitory (E/I) neurotransmission arising from dysfunction of GABAergic signaling system, the main inhibitory neurotransmitter system in the brain, to be at the core of the pathogenesis a variety of CNS disorders. Given the distribution and function of $GABA_A$ γ1 subunit-containing receptors in the CNS, they are very attractive targets for restoring levels of inhibition within key brain circuits and consequently the E/I balance in these conditions.

SUMMARY OF THE INVENTION

This invention relates to organic compounds useful for therapy or prophylaxis in a mammal, and in particular to $GABA_A$ γ1 receptor positive allosteric modulators (PAMs) for the treatment or prophylaxis of $GABA_A$ γ1 receptor related diseases and diseases or conditions which can be treated by the modulation of $GABA_A$ γ1 receptor activity, such autism spectrum disorders (ASD) targeting core symptoms and associated comorbidities including anxiety and irritability, Angelman syndrome, Rett syndrome, Prader-Willi syndrome, fragile-X disorder, schizophrenia including psychosis, cognitive impairment and negative symptoms, tardive dyskinesia, anxiety, separation anxiety disorder, selective mutism, specific phobia, social anxiety disorder (social phobia), panic disorder, agoraphobia, generalized anxiety disorder, substance/medication-induced anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders including narcolepsy-cataplexy, neurodegenerative conditions including Parkinson's disease (PD), Huntington's chorea, Alzheimer's disease (AD), mild cognitive impairment (MCI) dementia, behavioral and psychological symptoms (BPS) in neurodegenerative conditions, multi-infarct dementia, psychosis and aggression, eating disorders including anorexia nervosa, bulimia nervosa, binge eating disorder, depression and related conditions including treatment-resistant depression (TRD), chronic apathy, anhedonia, chronic fatigue, seasonal affective disorder, postpartum depression, drowsiness, sexual dysfunction, bipolar disorders, epilepsy and pain.

The present invention provides a novel compound of formula (I)

(I)

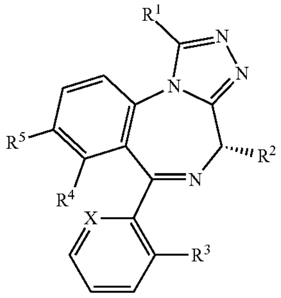

wherein $R^1$ is selected from i) H, ii) $C_{1-6}$alkyl, iii) $C_{1-6}$-alkoxy, iv) $C_{1-6}$-alkoxy-$C_{1-6}$-alkyl, v) hydroxy, vi) hydroxy-$C_{1-6}$-alkyl, vii) $C_{3-8}$-cycloalkyl optionally substituted by $R^7$, $R^8$ and $R^9$,
viii) amino-$C_{1-6}$-alkyl
ix) heteroaryl optionally substituted by $R^7$, $R^8$ and $R^9$, and
x) heterocycloalkyl optionally substituted by $R^7$, $R^8$ and $R^9$;

$R^2$ is selected from
i) $C_{1-6}$-alkyl,
ii) hydroxy
iii) hydroxy-$C_{1-6}$-alkyl, and
iv) $C_{1-6}$-alkoxy-$C_{1-6}$-alkyl;

$R^3$ is selected from
i) Cl, and
ii) F;

X is selected from
i) CR, and
ii) N;

$R^6$ is selected from
i) H,
ii) Cl, and
iii) F;

$R^4$ is selected from
i) Br, and
ii) Cl;

$R^5$ is selected from
i) $C_{1-6}$-alkyl,
ii) $C_{1-6}$-alkoxy,
iii) halogen,
iv) halo-$C_{1-6}$-alkyl,
v) cyano, and
vi) $C_{3-8}$-cycloalkyl;

$R^7$, $R^8$ and $R^9$ are independently selected from
i) $C_{1-6}$-alkyl, and
ii) $C_{1-6}$-alkoxy;

or pharmaceutically acceptable salts.

Compounds described herein and their pharmaceutically acceptable salts and esters can be used, alone or in combination with other drugs, as disease-modifying or as symptomatic agents for the treatment or prevention of acute neurological disorders, chronic neurological disorders, cognitive disorders, autism spectrum disorders (ASD), Angelman syndrome, Rett syndrome, Prader-Willi syndrome, fragile-X disorder, schizophrenia, tardive dyskinesia, anxiety, social anxiety disorder (social phobia), panic disorder, agoraphobia, generalized anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders, Parkinson's disease (PD), Huntington's chorea, Alzheimer's disease (AD), mild cognitive impairment (MCI), dementia, behavioral and psychological symptoms (BPS) in neurodegenerative conditions, multi-infarct dementia, agitation, psychosis, substance-induced psychotic disorder, aggression, eating disorders, depression, chronic apathy, anhedonia, chronic fatigue, seasonal affective disorder, postpartum depression, drowsiness, sexual dysfunction, bipolar disorders, epilepsy and pain.

In certain embodiments the indications treated in accordance with the invention are anxiety, targeting social anxiety disorder (social phobia) and generalized anxiety disorder, and autism spectrum disorder (ASD), targeting core symptoms and associated comorbidities including anxiety and irritability.

ASD is a complex, heterogeneous neurodevelopmental disorder characterized by impairments in two core domains: impairments in social interaction and communication, and presence of repetitive or restricted behaviors, interests, or activities (American Psychiatric Association 2013).

No approved pharmacological treatment exists for core symptoms of social deficits and restricted/repetitive behaviour of ASD, while only inadequate therapeutic options are available for most of ASD's affective and physiological co-morbidities. As a result, this disorder continues to be an area of high unmet medical need. Current approved treatments for associated symptoms of ASD are limited to the antipsychotics (Risperidone and Aripiprazole) indicated for the treatment of irritability associated with ASD symptoms. Emerging evidence suggests that the GABAergic system, the main inhibitory neurotransmitter system in the brain, plays a key role in the pathophysiology of ASD (Dhossche et al., 2002; Pizzarelli and Cherubini, 2011; Robertson et al., 2016).

Both genetic and imaging studies using positron emission tomography study (PET) and magnetic resonance spectroscopy (MRS) suggest alterations in GABAergic signaling in ASD. The gene encoding $GABA_A$ γ1: GABRG1 is located on chromosome 4 (mouse Chr.5) in a cluster with genes encoding α2, α4 and β1 $GABA_A$ receptor subunits. Rare CNVs, including inversion of chromosome 4p12 disrupting GABRG1 have been observed in autistic siblings (Horike et al., 2006), as well as GABRG1 loss in one case of ADHD. Mutations in 4p12 gene cluster have been linked to increased risk of anxiety, substance abuse and eating disorders—providing a link between GABRG1/4p12 and affective dysfunction. MRS studies found altered GABA levels in ASD (Gaetz et al., 2014; Rojas et al., 2014) and in particular some recent studies showed reduced GABA and altered somatosensory function in children with ASD and (Puts et al., 2016; Robertson et al., 2016). In line with these observations, a reduced number of inhibitory interneurons were found from postmortem tissues of ASD and TS patients (Rapanelli et al., 2017). Furthermore, reduced GABA synthesizing enzymes, glutamic acid decarboxylase (GAD) 65 and 67 were found in parietal and cerebellar cortices of patients with autism (Fatemi et al., 2002). Strong evidence in humans points to specific dysfunction in ASD of the limbic cortical regions known to form a coordinated functional network with $GABA_A$ γ1 subunit-containing extended amygdala/hypothalamus regions. These areas: Cortical/lateral amygdala, Insula, PFC, and Cingulate are recognized key for processing of social and emotionally relevant stimuli. While subcortical subnuclei that form specific partnerships with these areas, coordinating behavioural outcomes, are often difficult to study due to spatial resolution limitations, many lines of evidence point to hyper-recruitment of these cortical- to sub cortical connections in ASD. Moreover, recent high resolution studies provide a clear link between extended amygdala activity/functional connectivity and emotional state (Kleinhans et al., 2009, 2016; Swartz et al., 2013; Nordahl et al., 2016; Ehrlich et al., 2017; Avino et al., 2018; Ibrahim et al., 2019). Targeting such highly specific limbic subcortical regions, which exhibit substantial molecular and cellular diversity compared to the neocortex, will create a precision entry point for safe and specific therapeutic modulation of ASD-affected socio-affective circuits, while avoiding broad modulation of global brain state. Enhancement of $GABA_A$ receptor activity by non-selective BZDs have been shown to ameliorate behavioral deficits in mouse models of ASD, however very narrow therapeutic margins were observed due to sedation mediated by the $GABA_A$ al 02 subtype (Han et al., 2012, 2014; Soto et al., 2013). These findings support the notion that rebalancing of GABAergic transmission via $GABA_A$ γ1 receptors can improve symptoms in ASD without the side effects of non-selective benzodiazepines.

Objects of the present invention are compounds of formula (I) and their pharmaceutically acceptable salts and esters, the preparation of the above mentioned compounds, medicaments containing them and their manufacture as well as the use of the above mentioned compounds in the treatment or prevention of diseases related to $GABA_A$ γ1 receptor dysfunction and diseases or conditions which can be treated by the enhancement of $GABA_A$ γ1 receptor activity, such as autism spectrum disorders (ASD), Angelman syndrome, Rett syndrome, Prader-Willi syndrome, fragile-X disorder, schizophrenia, tardive dyskinesia, anxiety, separation anxiety disorder, selective mutism, specific phobia, social anxiety disorder, panic disorder, agoraphobia, generalized anxiety disorder, substance/medication-induced anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders including narcolepsy-cataplexy, neurodegenerative conditions including Parkinson's disease (PD), Huntington's chorea, Alzheimer's disease (AD), mild cognitive impairment (MCI) dementia, behavioral and psychological symptoms (BPS) in neurodegenerative conditions, multi-infarct dementia, psychosis and aggression, eating disorders including anorexia nervosa, bullimia nervosa, binge eating disorder, depression and related conditions including treatment-resistant depression (TRD), chronic apathy, anhedonia, chronic fatigue, seasonal affective disorder, postpartum depression, drowsiness, sexual dysfunction, bipolar disorders, epilepsy and pain.

Compounds of the present invention are selective $GABA_A$ γ1 receptor positive allosteric modulators (PAMs) as they selectively enhance the function of γ1-containing $GABA_A$ receptors by increasing GABAergic currents (influx of chloride) at a given concentration (e.g. $EC_{20}$) of gamma amino butyric acid (GABA). The compounds of the present invention have high PAM efficacy and binding selectivity for the γ1-containing subtypes (α5γ1, α2γ1, α1γ1) relative to the □2-containing subtypes (e.g. α1γ2, α2γ2, α3γ2 and α5γ2). As such, compounds of the present invention are strongly differentiated from classical benzodiazepine drugs such as Alprazolam, Triazolam, Estazolam, Midazolam which are selective for the □2-containing $GABA_A$ subtypes and possess low affinity for the γ1-containing subtypes. Compatible with the γ1-subtypes brain distribution, selective $GABA_A$ γ1 PAMs will restore GABAergic signaling in key brain regions (e.g. extended amygdala: central, medial, and bed nucleus of the stria terminalis, lateral septum, hypothalamus, and pallidum/nigra) without the side-effects of non-selective $GABA_A$ modulators (e.g. benzodiazepines).

The term "amino" denotes a —$NH_2$ group.

The term "amino-$C_{1-6}$-alkyl" denotes an $C_{1-6}$-alkyl group wherein one of the hydrogen atoms of the $C_{1-6}$-alkyl group has been replaced by an amino group. Examples of amino-$C_{1-6}$-alkyl include aminomethyl, aminoethyl, aminopropyl, aminomethylpropyl, aminomethylethyl and aminobutyl.

Particular example includes aminomethyl.

The term "$C_{1-6}$-alkoxy" denotes a group of the formula —O—R', wherein R' is an $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are methoxy and ethoxy. More particular example is methoxy.

The term "$C_{1-6}$-alkoxy-$C_{1-6}$-alkyl" denotes an $C_{1-6}$-alkyl group wherein at least one of the hydrogen atoms of the $C_{1-6}$-alkyl group has been replaced by an $C_{1-6}$-alkoxy group. Exemplary $C_{1-6}$-alkoxy-$C_{1-6}$-alkyl groups include methoxymethyl, ethoxymethyl, methoxymethyl, ethoxyethyl, methoxypropyl and ethoxypropyl. Particular example includes methoxymethyl.

The term "$C_{1-6}$-alkyl" denotes a monovalent linear or branched saturated hydrocarbon group of 1 to 6 carbon atoms. Examples of $C_{1-6}$-alkyl include methyl, ethyl, n-propyl, isopropyl, n-butyl, iso-butyl, sec-butyl, tert-butyl and pentyl. Particular $C_{1-6}$alkyl groups are methyl and ethyl. More particular example is methyl.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having one or two carbon atoms in common. Examples of monocyclic $C_{3-4}$-cycloalkyl are cyclopropyl, cyclobutanyl, cyclopentyl, cyclohexyl or cycloheptyl. Example of bicyclic $C_{3-8}$-cycloalkyl is spiro [3.3]heptanyl. Particular monocyclic $C_{3-8}$-cycloalkyl groups are cyclopropyl and cyclobutanyl. More particular monocyclic $C_{3-8}$-cycloalkyl group include cyclopropyl.

The term "cyano" denotes a —CN group.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhalo-$C_{1-6}$-alkyl-$C_{1-6}$alkyl" denotes an —$C_{1-4}$-alkyl-$C_{1-4}$-alkyl group where all hydrogen atoms of the alkyl group have been replaced by the same or different halogen atoms. Examples of halo-$C_{1-6}$-alkyl include fluoromethyl, difluoromethyl, trifluoromethyl, fluoroethyl, difluoroethyl and trifluoroethyl. Particular halo-$C_{1-6}$-alkyl groups include trifluoromethyl and difluoroethyl. More particular halo-$C_{1-6}$-alkyl group is trifluoromethyl.

The term "halogen" and "halo" are used interchangeably herein and denote fluoro, chloro, bromo or iodo. Particular halogens include fluoro and chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyridinyl, pyrazolyl, pyrimidinyl, pyridazinyl and isoxazolyl. More particular heteroaryl groups are pyrazolyl, pyrimidinyl, pyridazinyl and isoxazolyl.

The term "heterocycloalkyl" denotes a monovalent saturated or partly unsaturated mono- or bicyclic ring system of 4 to 11 ring atoms, comprising 1, 2, or 3 ring heteroatoms selected from N, O and S, the remaining ring atoms being carbon. Bicyclic means consisting of two cycles having one or two ring atoms in common. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydrothiophenyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are oxabicyclo[2.2.1]heptanyl, oxaspiro[3.3]heptanyl, 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular heterocycloalkyl is tetrahydropyranyl.

The term "hydroxy" denotes a —OH group.

The term "hydroxy-$C_{1-6}$-alkyl" denotes an $C_{1-6}$-alkyl group wherein one of the hydrogen atoms of the $C_{1-6}$alkyl group has been replaced by a hydroxy group. Examples of hydroxy-$C_{1-6}$-alkyl include hydroxymethyl, hydroxyethyl, hydroxypropyl, hydroxymethylpropyl hydroxymethylethyl and hydroxybutyl. Particular example includes hydroxymethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry.

Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention is a compound according to formula (I) as described herein and pharmaceutically acceptable salts or esters thereof, in particular compounds according to formula (I) as described herein and pharmaceutically acceptable salts thereof, more particularly compounds according to formula (I) as described herein.

One embodiment of the present invention provides a compound according to formula (I) as described herein, wherein $R^1$ is selected from
- i) H,
- ii) $C_{1-6}$-alkyl,
- iii) $C_{1-6}$-alkoxy,
- iv) $C_{1-6}$-alkoxy-$C_{1-6}$-alkyl,
- v) hydroxy,
- vi) hydroxy-$C_{1-6}$-alkyl,
- vii) $C_{3-8}$-cycloalkyl optionally substituted by $R^7$, $R^8$ and $R^9$,
- viii) amino-$C_{1-6}$-alkyl
- ix) pyrazolyl optionally substituted by $R^7$, $R^8$ and $R^9$,
- x) pyridinyl optionally substituted by $R^7$, $R^8$ and $R^9$,
- xi) pyrimidinyl optionally substituted by $R^7$, $R^8$ and $R^9$,
- xii) pyridazinyl optionally substituted by $R^7$, $R^8$ and $R^9$, and
- xiii) isoxazolyl optionally substituted by $R^7$, $R^8$ and $R^9$;

$R^2$ is selected from
- i) $C_{1-6}$-alkyl,
- ii) hydroxy
- iii) hydroxy-$C_{1-6}$-alkyl, and
- iv) $C_{1-6}$-alkoxy-$C_{1-6}$-alkyl;

$R^3$ is selected from
- i) Cl, and
- ii) F;

X is selected from
- i) CR, and
- ii) N;

$R^6$ is selected from
- i) H,
- ii) Cl, and
- iii) F;

$R^4$ is selected from
- i) Br, and
- ii) Cl;

$R^5$ is selected from
- i) $C_{1-6}$-alkyl,
- ii) $C_{1-6}$-alkoxy,
- iii) halogen,
- iv) halo-$C_{1-6}$-alkyl,
- v) $C_{3-8}$-cycloalkyl;

$R^7$, $R^8$ and $R^9$ are independently selected from
i) $C_{1-6}$-alkyl, and
ii) $C_{1-6}$-alkoxy;
or pharmaceutically acceptable salts.

A more particular embodiment of the present invention provides a compound of formula (I) according to claim 1, wherein
$R^1$ is selected from
i) H,
ii) $C_{1-6}$-alkyl,
iii) hydroxy,
iv) hydroxy-$C_{1-6}$-alkyl,
v) $C_{3-8}$-cycloalkyl optionally substituted by $R^7$, $R^8$ and $R^9$,
vi) pyrazolyl optionally substituted by $R^7$, $R^8$ and $R^9$,
vii) pyrimidinyl optionally substituted by $R^7$, $R^8$ and $R^9$,
viii) pyridazinyl optionally substituted by $R^7$, $R^8$ and $R^9$, and
ix) isoxazolyl optionally substituted by $R^7$, $R^8$ and $R^9$;
$R^2$ is selected from
i) $C_{1-6}$-alkyl,
ii) hydroxy
iii) hydroxy-$C_{1-6}$-alkyl, and
iv) $C_{1-6}$-alkoxy-$C_{1-6}$-alkyl;
$R^3$ is F;
X is selected from
i) $CR^6$, and
ii) N;
$R^6$ is selected from
i) H, and
ii) F;
$R^4$ is selected from
i) Br, and
ii) Cl;
$R^5$ is selected from
i) $C_{1-6}$-alkyl,
ii) halogen, and
iii) halo-$C_{1-6}$-alkyl;
$R^7$, $R^8$ and $R^9$ are independently selected from $C_{1-6}$-alkyl,
or pharmaceutically acceptable salts.

A furthermore particular embodiment of the present invention provides a compound according to formula (I) as described herein,
$R^1$ is $C_{1-6}$-alkyl;
$R^2$ is $C_{1-6}$-alkyl;
$R^3$ is F;
X is $CR^6$;
$R^6$ is F;
$R^4$ is Cl;
$R^5$ is halo-$C_{1-6}$-alkyl;
or pharmaceutically acceptable salts.

Another particular embodiment of the present invention provides a compound according to formula (I) as described herein, wherein $R^1$ is selected from
i) H,
ii) $C_{1-6}$-alkyl,
iii) $C_{1-6}$-alkoxy,
iv) $C_{1-6}$-alkoxy-$C_{16}$-alkyl,
v) hydroxy,
vi) hydroxy-$C_{1-6}$-alkyl,
vii) $C_{3-8}$-cycloalkyl optionally substituted by $R^7$, $R^8$ and $R^9$,
viii) amino-$C_1$-alkyl
ix) pyrazolyl optionally substituted by $R^7$, $R^8$ and $R^9$,
x) pyridinyl optionally substituted by $R^7$, $R^8$ and $R^9$,
xi) pyrimidinyl optionally substituted by $R^7$, $R^8$ and $R^9$,
xii) pyridazinyl optionally substituted by $R^7$, $R^8$ and $R^9$, and
xiii) isoxazolyl optionally substituted by $R^7$, $R^8$ and $R^9$;

Another particular embodiment of the present invention provides a compound according to formula (I) as described herein, wherein $R^1$ is selected from
i) H,
ii) $C_{1-6}$-alkyl,
iii) hydroxy,
iv) hydroxy-$C_{1-6}$-alkyl,
v) $C_{3-8}$-cycloalkyl optionally substituted by $R^7$, $R^8$ and $R^9$,
vi) pyrazolyl optionally substituted by $R^7$, $R^8$ and $R^9$,
vii) pyrimidinyl optionally substituted by $R^7$, $R^8$ and $R^9$,
viii) pyridazinyl optionally substituted by $R^7$, $R^8$ and $R^9$, and
ix) isoxazolyl optionally substituted by $R^7$, $R^8$ and $R^9$;

Another particular embodiment of the present invention provides a compound according to formula (I) as described herein, wherein $R^1$ is $C_{1-6}$-alkyl.

Another particular embodiment of the present invention provides a compound according to formula (I) as described herein, wherein $R^2$ is $C_{1-6}$-alkyl.

Another particular embodiment of the present invention provides a compound according to formula (I) as described herein, wherein $R^3$ is F.

Another particular embodiment of the present invention provides a compound according to formula (I) as described herein, wherein X is $CR^6$.

Another particular embodiment of the present invention provides a compound according to formula (I) as described herein, wherein $R^6$ is F.

Another particular embodiment of the present invention provides a compound according to formula (I) as described herein, wherein $R^4$ is Cl.

Another particular embodiment of the present invention provides a compound according to formula (I) as described herein, wherein $R^5$ is selected from
i) $C_{1-6}$-alkyl,
ii) $C_{1-6}$-alkoxy,
iii) halogen,
iv) halo-$C_{1-6}$-alkyl,
v) $C_{3-8}$-cycloalkyl;

Another particular embodiment of the present invention provides a compound according to formula (I) as described herein, wherein $R^5$ is selected from
i) $C_{1-6}$-alkyl,
ii) halogen, and
iii) halo-$C_{1-6}$-alkyl;

Another particular embodiment of the present invention provides a compound according to formula (I) as described herein, wherein $R^5$ is halo-$C_{1-6}$-alkyl.

Another particular embodiment of the present invention provides a compound according to formula (I) as described herein, wherein $R^7$, $R^8$ and $R^9$ are independently selected from $C_{1-6}$-alkyl.

Particular examples of a compound of formula (I) as described herein are selected from
(4S)-8-bromo-7-chloro-6-(2-fluorophenyl)-4-methyl-4H-[1,2,4]triazolo[4,3-a][1,4]benzodiazepine;
8-bromo-7-chloro-6-(2,6-difluorophenyl)-4H-[1,2,4]triazolo[4,3-a][1,4]benzodiazepin-4-ol;
(4S)-8-bromo-7-chloro-6-(2-fluorophenyl)-4-methyl-1-pyridazin-3-yl-4H-[1,2,4]triazolo[4,3-a][1,4]benzodiazepine;

8-bromo-7-chloro-6-(2-fluorophenyl)-1-pyridazin-3-yl-4H-[1,2,4]triazolo[4,3-a][1,4]benzodiazepin-4-ol;
(4S)-8-bromo-7-chloro-6-(2,6-difluorophenyl)-4-methyl-4H-[1,2,4]triazolo[4,3-a][1,4]benzodiazepine;
(4S)-7,8-dichloro-6-(2,6-difluorophenyl)-4-methyl-1-pyrimidin-4-yl-4H-[1,2,4]triazolo[4,3-a][1,4]benzodiazepine;
(4S)-7,8-dichloro-6-(2,6-difluorophenyl)-4-methyl-1-(1-methylpyrazol-4-yl)-4H-[1,2,4]triazolo[4,3-a][1,4]benzodiazepine;
(4S)-7,8-dichloro-6-(2,6-difluorophenyl)-4-methyl-1-pyridazin-3-yl-4H-[1,2,4]triazolo[4,3-a][1,4]benzodiazepine;
(4S)-7,8-dichloro-6-(3-fluoro-2-pyridyl)-4-methyl-1-pyridazin-3-yl-4H-[1,2,4]triazolo[4,3-a][1,4]benzodiazepine;
(4S)-7,8-dichloro-6-(2,6-difluorophenyl)-4-methyl-2,4-dihydro-[1,2,4]triazolo[4,3-a][1,4]benzodiazepin-1-one;
(4S)-7,8-dichloro-6-(3-fluoro-2-pyridyl)-4-methyl-1-pyrimidin-4-yl-4H-[1,2,4]triazolo[4,3-a][1,4]benzodiazepine;
(4S)-7,8-dichloro-6-(3-fluoro-2-pyridyl)-4-methyl-1-(1-methylpyrazol-4-yl)-4H-[1,2,4]triazolo[4,3-a][1,4]benzodiazepine;
(4S)-7,8-dichloro-1-cyclopropyl-6-(3-fluoro-2-pyridyl)-4-methyl-4H-[1,2,4]triazolo[4,3-a][1,4]benzodiazepine;
(4S)-7-bromo-8-chloro-6-(2,6-difluorophenyl)-4-methyl-1-pyridazin-3-yl-4H-[1,2,4]triazolo[4,3-a][1,4]benzodiazepine;
(4S)-7-bromo-8-chloro-6-(2,6-difluorophenyl)-4-methyl-1-pyrimidin-4-yl-4H-[1,2,4]triazolo[4,3-a][1,4]benzodiazepine;
(4S)-8-bromo-7-chloro-6-(2,6-difluorophenyl)-1,4-dimethyl-4H-[1,2,4]triazolo[4,3-a][1,4]benzodiazepine;
(4S)-7-bromo-8-chloro-6-(2,6-difluorophenyl)-4-methyl-1-(1-methylpyrazol-4-yl)-4H-[1,2,4]triazolo[4,3-a][1,4]benzodiazepine;
(4S)-7-bromo-8-chloro-6-(2,6-difluorophenyl)-1,4-dimethyl-4H-[1,2,4]triazolo[4,3-a][1,4]benzodiazepine;
(4S)-7-bromo-8-chloro-6-(2,6-difluorophenyl)-4-methyl-1-(1-methylpyrazol-3-yl)-4H-[1,2,4]triazolo[4,3-a][1,4]benzodiazepine;
(4S)-7,8-dichloro-6-(2,6-difluorophenyl)-1,4-dimethyl-4H-[1,2,4]triazolo[4,3-a][1,4]benzodiazepine;
(4S)-8-bromo-7-chloro-1-cyclopropyl-6-(3-fluoro-2-pyridyl)-4-methyl-4H-[1,2,4]triazolo[4,3-a][1,4]benzodiazepine;
(4S)-8-bromo-7-chloro-6-(3-fluoro-2-pyridyl)-4-methyl-4H-[1,2,4]triazolo[4,3-a][1,4]benzodiazepine;
(4S)-8-bromo-7-chloro-6-(3-fluoro-2-pyridyl)-1,4-dimethyl-4H-[1,2,4]triazolo[4,3-a][1,4]benzodiazepine;
(4S)-7,8-dichloro-6-(2,6-difluorophenyl)-4-methyl-1-(6-methylpyridazin-3-yl)-4H-[1,2,4]triazolo[4,3-a][1,4]benzodiazepine;
5-[(4S)-7,8-dichloro-6-(2,6-difluorophenyl)-4-methyl-4H-[1,2,4]triazolo[4,3-a][1,4]benzodiazepin-1-yl]-3-methyl-isoxazole;
(4S)-7-bromo-8-chloro-6-(2,6-difluorophenyl)-4-methyl-1-(6-methylpyridazin-3-yl)-4H-[1,2,4]triazolo[4,3-a][1,4]benzodiazepine;
(4S)-7-bromo-8-chloro-6-(2,6-difluorophenyl)-4-methyl-2,4-dihydro-[1,2,4]triazolo[4,3-a][1,4]benzodiazepin-1-one;
(4S)-7-chloro-6-(2,6-difluorophenyl)-1,4-dimethyl-8-(trifluoromethyl)-4H-[1,2,4]triazolo[4,3-a][1,4]benzodiazepine;
(4S)-7-chloro-8-(1,1-difluoroethyl)-6-(2,6-difluorophenyl)-1,4-dimethyl-4H-[1,2,4]triazolo[4,3-a][1,4]benzodiazepine;
(4S)-7,8-dichloro-6-(2,6-difluorophenyl)-4-methyl-1-(6-methylpyrimidin-4-yl)-4H-[1,2,4]triazolo[4,3-a][1,4]benzodiazepine;
(4S)-7,8-dichloro-6-(2,6-difluorophenyl)-4-methyl-1-(2-methylpyrimidin-4-yl)-4H-[1,2,4]triazolo[4,3-a][1,4]benzodiazepine;
(4S)-7,8-dichloro-6-(2,6-difluorophenyl)-1-(2,6-dimethylpyrimidin-4-yl)-4-methyl-4H-[1,2,4]triazolo[4,3-a][1,4]benzodiazepine;
(4S)-7-chloro-6-(2,6-difluorophenyl)-1,4,8-trimethyl-4H-[1,2,4]triazolo[4,3-a][1,4]benzodiazepine;
(4S)-8-bromo-7-chloro-6-(2,6-difluorophenyl)-4-ethyl-1-methyl-4H-[1,2,4]triazolo[4,3-a][1,4]benzodiazepine;
(4S)-7-chloro-8-(difluoromethyl)-6-(2,6-difluorophenyl)-1,4-dimethyl-4H-[1,2,4]triazolo[4,3-a][1,4]benzodiazepine;
(4R)-8-bromo-7-chloro-6-(2,6-difluorophenyl)-4-(methoxymethyl)-1-methyl-4H-[1,2,4]triazolo[4,3-a][1,4]benzodiazepine;
[(4R)-8-bromo-7-chloro-6-(2,6-difluorophenyl)-1-methyl-4H-[1,2,4]triazolo[4,3-a][1,4]benzodiazepin-4-yl]methanol;
(4S)-7-chloro-6-(2,6-difluorophenyl)-8-iodo-1,4-dimethyl-4H-[1,2,4]triazolo[4,3-a][1,4]benzodiazepine;
[(4S)-7-chloro-6-(2,6-difluorophenyl)-4-methyl-8-(trifluoromethyl)-4H-[1,2,4]triazolo[4,3-a][1,4]benzodiazepin-1-yl]methanol;
(4R)-7-chloro-6-(2,6-difluorophenyl)-4-(methoxymethyl)-1-methyl-8-(trifluoromethyl)-4H-[1,2,4]triazolo[4,3-a][1,4]benzodiazepine;
[(4R)-7-chloro-6-(2,6-difluorophenyl)-1-methyl-8-(trifluoromethyl)-4H-[1,2,4]triazolo[4,3-a][1,4]benzodiazepin-4-yl]methanol;
(4S)-7-chloro-6-(2,6-difluorophenyl)-4-methyl-8-(trifluoromethyl)-4H-[1,2,4]triazolo[4,3-a][1,4]benzodiazepine;
(4S)-7-chloro-6-(2,6-difluorophenyl)-1-ethyl-4-methyl-8-(trifluoromethyl)-4H-[1,2,4]triazolo[4,3-a][1,4]benzodiazepine;
(4S)-7-chloro-6-(2,6-difluorophenyl)-8-ethyl-1,4-dimethyl-4H-[1,2,4]triazolo[4,3-a][1,4]benzodiazepine;

or pharmaceutically acceptable salts thereof.

Furthermore particular examples of a compound of formula (I) as described herein are selected from (4S)-7-chloro-6-(2,6-difluorophenyl)-1,4-dimethyl-8-(trifluoromethyl)-4H-[1,2,4]triazolo[4,3-a][1,4]benzodiazepine or pharmaceutically acceptable salts thereof.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^2H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes for the manufacture of a compound of formula (I) as described herein are also an object of the invention.

Scheme 1, a compound of formula (I) can be prepared in two steps starting from lactames (building blocks A, B, G, L, M, O, Q-U) of formula (II). Following thionation reaction using Lawesson's reagent or $P_2S_5$, lactames (II) are converted to corresponding thiolactames (III). Their reaction with hydrazides (IV) via a Pellizzari type process yields 1,2,4-triazoles of general formula (I). In alternative, 1,2,4-triazoles (I) can be obtained by reaction between thiolactames (II) and hydrazine to form hydrazones (V) followed by treatment with triethyl orthoacetate or triethyl orthoformate.

In certain embodiments of the invention where $R^1$ is hydroxyl (OH), benzodiazepines of formula (I) can be obtained in two steps according to the process described in Scheme 2. It is widely accepted that 3-hydroxy-1,2,4-triazoles are existing as two tautomeric forms and in this invention they will be represented exclusively in their most stable form (triazolones). To this end, hydrazones (V) can be reacted with 1,1'-carbonyldiimidazole (CDI) to yield triazolones of formula (I) (Scheme 2).

Scheme 2: synthesis of benzodiazepines (I) wherein $R^1$ is hydroxyl; all other definitions are as described above and in the claims

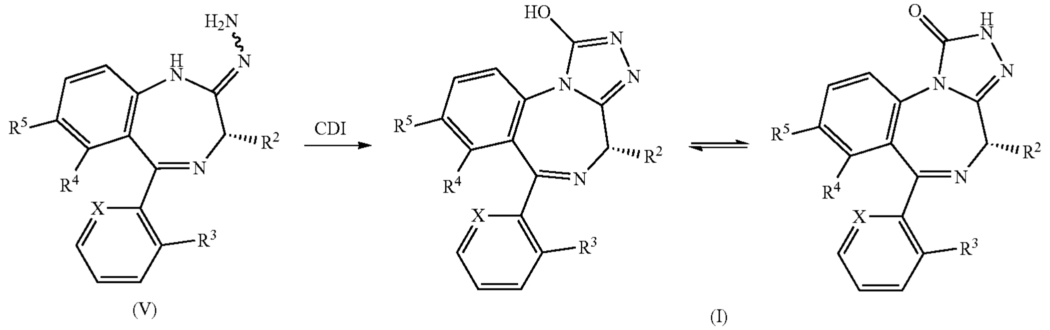

(V)

(I)

The preparation of compounds of formula (I) of the invention may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. The reaction sequence is not limited to the one displayed in schemes 1-4, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula (I) and their pharmaceutically acceptable salts can be prepared by a process described below (Scheme 1).

Scheme 1: synthesis of benzodiazepines (I) wherein all definitions are as described above and in the According to The synthesis of building blocks (A, B, G, L, M, O, Q-U) of formula (II) is highlighted in Scheme 3. Commercially available 2-amino-6-chlorobenzoic acid or 2-amino-6-bromobenzoic acid can be heated in acetic anhydride to form 5-chloro-2-methyl-3,1-benzoxazin-4-one and 5-bromo-2-methyl-3,1-benzoxazin-4-one, respectively. Grignard or organolithium reagents of formula (VI) (prepared by metalation reaction from corresponding aryl bromide or via kinetic deprotonation) can be reacted with benzoxazin-4-ones (electrophiles) at controlled temperatures to provide ketones of formula (VII). Following N-acetamide hydrolysis under acidic conditions (HCl), compounds of formula (VII) are converted into anilines of formula (VIII). Conveniently, at this junction, the halogen at $R^5$ can be installed by treatment with N-chlorosuccinimide (NCS), N-bromosuccinimide (NBS) or N-iodosuccinimide (NIS) to yield intermediates of formula (IX). Final thermal cyclisation reaction with ethyl 2-aminoacetate hydrochloride in pyridine yields the desired benzodiazepines (II), presumably via formation of imine intermediate (X).

Scheme 3: synthesis of building blocks (A, B, G, L, M, O, Q-U) wherein $R^5$ is Cl, Br or I and $R^2$ is H; all other definitions are as described above and in the claims
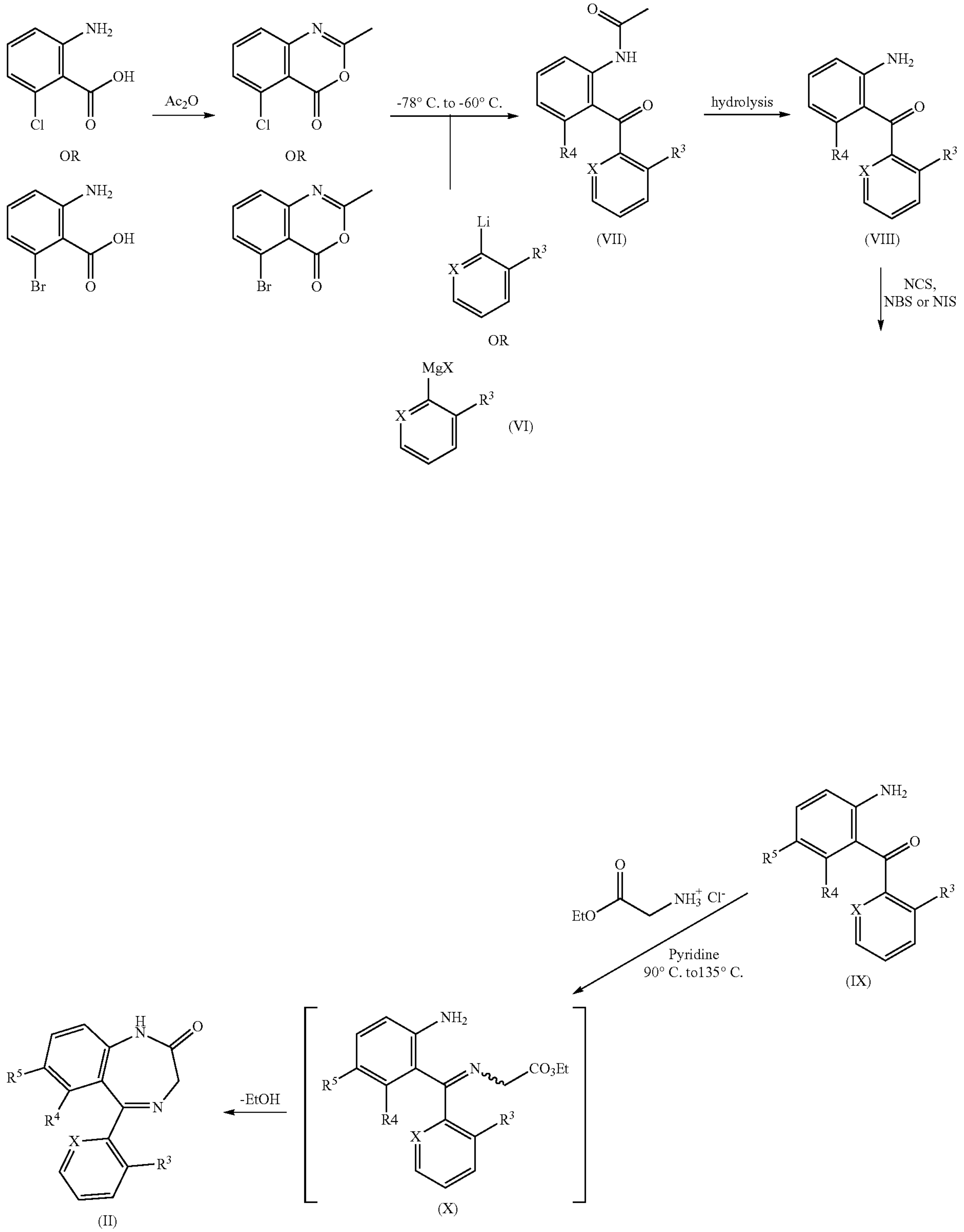
Building block
A, B, G, L, M, O, Q-U In further embodiments of the invention, where $R^2$ is alkyl or substituted alkyl, an alternative process is envisaged and detailed in Scheme 4.

Scheme 4: synthesis of building blocks (A, B, G, L, M, O, Q-U) wherein $R^5$ is Cl, Br or I and $R^2$ is alkyl or substituted alkyl; all other definitions are as described above and in the claims

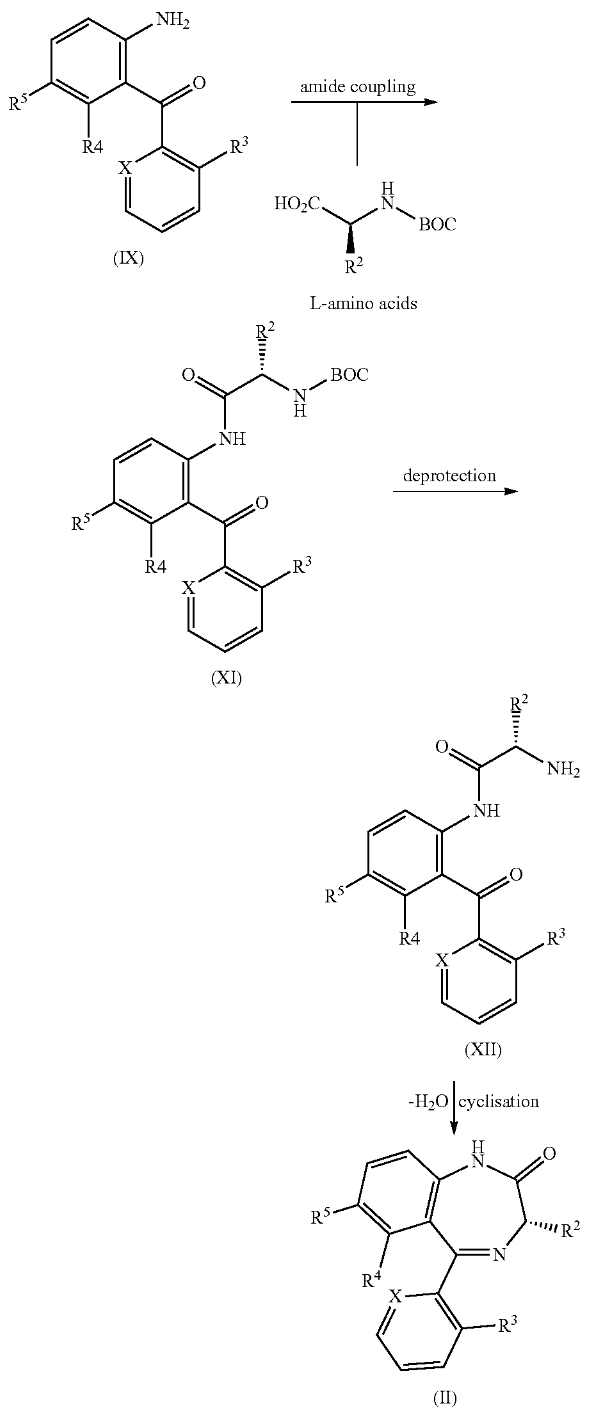

Building block A, B, G, L, M, O, Q-U

In such a case, compounds of formula (XI) can be prepared by amide coupling reaction between anilines (IX) and N-Boc protected L-amino acids upon exposure to phosphoryl chloride ($POCl_3$), or by other methods known to those skilled in the art. Removal of N-Boc protecting group can be effected with mineral acids (e.g. HCl) or organic acids (e.g. trifluoroacetic acid) to yield amines of formula (XII). Final intramolecular condensation reaction promoted by acidic media (e.g. silica or acetic acid) and heat (80-110° C.) provides the desired benzodiazepine building blocks (A-U) of formula (II). Notably, in the processes described in Scheme 1 and 4, racemization at the chiral center occurs to a different extent (20-100%) depending on specific reaction conditions adopted. As a result, chiral purification (e.g. by HPLC or SFC) of final derivatives of formula (I) is required to obtain final derivatives with enantiomeric excess (ee) above 97%.

Also an embodiment of the present invention is a process to prepare a compound of formula (I) as defined above comprising the reaction of a compound of formula (III) with a compound of formula (IV) in a solvent, particularly an alcohol, such as butan-1-ol, and at temperature between room temperature and reflux of solvent, particularly at reflux of solvent.

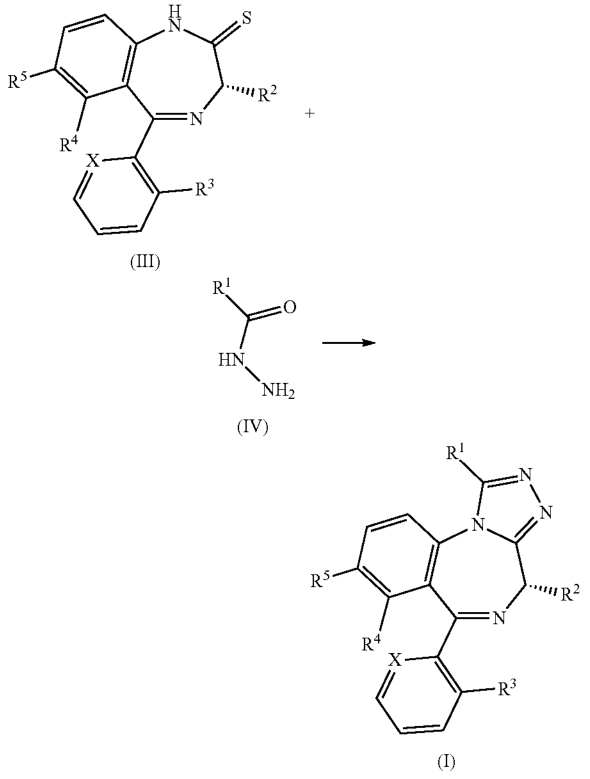

wherein $R^1$, $R^2$, $R^3$, $R^4$ and $R^5$ are as defined herein.

Also an object of the present invention is a compound according to formula (I), more particularly compounds of formula (I), as described herein for use as a therapeutically active substance.

Likewise an object of the present invention is a pharmaceutical composition comprising a compound according to formula (I), more particularly compounds of formula (I), as described herein and a therapeutically inert carrier.

A particular embodiment of the present invention is a compound according to formula (I) or pharmaceutically acceptable salts thereof, as described herein for use in the treatment or prophylaxis, more particularly for use the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

The present invention also relates to the use of a compound according to formula (I) or pharmaceutically acceptable salts thereof, more particularly compounds of formula (I), as described herein for the preparation of a medicament for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

Also an object of the invention is a method for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD), which method comprises administering an effective amount of a compound according to formula (I), more particularly compounds of formula (I), as described herein.

Also an embodiment of the present invention are compounds of formula (I), more particularly compounds of formula (I), as described herein, when manufactured according to any one of the described processes.

Assay Procedures

Membrane Preparation and Binding Assay for γ1-Containing $GABA_A$ Subtypes

The affinity of compounds at $GABA_A$ γ1 subunit-containing receptors was measured by competition for [$^3$H]RO7239181 (67.3 Ci/mmol; Roche) binding to membranes from HEK293F cells (ThermoFisher R79007) expressing human (transiently transfected) receptors of composition α5β2γ1, α2β2γ1, α1β2γ1. For better protein expression of the α2 subunit-containing receptors, the 28 amino acid long signal peptide (Met1 to Ala28) of the human $GABA_A$ α2 subunit was substituted by the 31 amino acid long signal peptide (Met1 to Ser31) of human $GABA_A$ α5 subunit.

Harvested pellets from HEK293F cells expressing the different $GABA_A$ receptor subtypes were resuspended in Mannitol Buffer pH 7.2-7.4 (Mannitol 0.29M, Triethylamine 10 mM, Acetic acid 10 mM, EDTA 1 mM plus protease inhibitors (20 tablets Complete, Roche Diagnostics Cat. No. 05 056 489 001 per liter)), washed two times and then resuspended at 1:10 to 1:15 dilution in the same buffer. Cell disruption was performed by stirring the suspension in a Parr vessel #4637 at 435 psi for 15 minutes, and then the suspensions were centrifuged at 1000×g for 15 minutes at 4° C. (Beckman Avanti J-HC; rotor JS)-4.2). The supernatant (S1) was transferred in a 21 Schott flask and the pellet (P1) was resuspended with Mannitol Buffer up to 175 ml. The resuspended pellet was transferred into a 250 ml Corning centrifugal beaker and centrifuged at 1500×g for 10 minutes at 4° C. (Beckman Avanti J-HC; rotor JS)-4.2). The supernatant (S1) was then transferred in the 21 Schott flask and the pellet was discarded. The supernatants (S1) were centrifuged in 500 ml Beckman polypropylene centrifugal beaker at 15,000×g for 30 minutes at 4° C. (Beckman Avanti J-20 XP; rotor JLA-10.500). The pellet (P2) was resuspended with Mannitol Buffer 1:1 and frozen at −80° C. The supernatant (S2) was centrifuged in 100 ml Beckman polypropylene centrifugal tubes at 48000×g for 50 minutes at 40° C. (Beckman Avanti J-20 XP; rotor JA-18). The supernatant (S3) was discarded and the pellet (P3) was resuspended with 1:1 Mannitol Buffer. The P2 and P3 protein concentration was determined with the BIORAD Standard assay method with bovine serum albumin as standard and measured on the NANO-Drop 1000. The membrane suspension was aliquots (500 μl per tube) and stored at −80° C. until required.

Membrane homogenates were resuspended and polytronised (Polytron PT1200E Kinematica AG) in Potassium Phosphate 10 mM, KCl 100 mM binding buffer at pH 7.4 to a final assay concentration determined with a previous experiment.

Radioligand binding assays were carried out in a volume of 200 □L (96-well plates) which contained 100 μL of cell membranes, [$^3$H]RO7239181 at a concentration of 1.5 nM (α5β2γ1) or 20-30 nM (α1β2γ1, 2β2γ1) and the test compound in the range of $[0.3\text{-}10000]\times10^{-9}$ M. Nonspecific binding was defined by $10\times10^{-6}$ (α5β2γ1) and $30\times10^{-6}$ M RO7235136 and typically represented less than 5% (α5β2γ1) and less than 20% (α1β2γ1, α2β2γ1) of the total binding. Assays were incubated to equilibrium for 1 hour at 4° C. and then, membranes were filtered onto unifilter (96-well white microplate with bonded GF/C filters preincubated 20-50 minutes in 0.3% Polyethylenimine) with a Filtermate 196 harvester (Packard BioScience) and washed 4 times with cold Potassium Phosphate 10 mM pH 7.4, KCl 100 mM binding buffer. After drying, filter-retained radioactivity was detected by liquid scintillation counting. $K_i$ values were calculated using Excel-Fit (Microsoft) and are the means of two determinations.

The compounds of the accompanying examples were tested in the above described assays, and the preferred compounds were found to possess a $K_i$ value for the displacement of [$^3$H]RO7239181 from $GABA_A$ γ1 subunit-containing receptors (e.g. α5β2γ1, α2β2γ1, α1β2γ1) of 100 nM or less. Most preferred are compounds with a Ki (nM)<50. Representative test results, obtained by the above described assay measuring binding affinity to HEK293 cells expressing human (h) receptors, are shown in the Table 1.

Preparation of [$^3$H]RO7239181, 6-chloro-5-(2,6-difluorophenyl-7-methyl-1-(tritritiomethyl)-3H-1,4-benzodiazepin-2-one a) 6-Chloro-5-(2,6-difluorophenyl)-7-methyl-1,3-dihydro-1,4-benzodiazepin-2-one A microwave tube was charged with 7-bromo-6-chloro-5-(2,6-difluorophenyl)-1,3-dihydro-1,4-benzodiazepin-2- one (building block A (see infra), 450 mg, 1.17 mmol), trimethylboroxine (205 mg, 228 μL, 1.63 mmol), potassium carbonate (242 mg, 1.75 mmol) and tetrakis(triphenylphosphine)palladium (0) (67.4 mg, 58.4 μmol). Degassed 1,4-dioxane (8.1 mL) and $H_2O$ (2.7 ml) were added then the vial was capped. The suspension was reacted in microwave at 130° C. for 30 min to give complete conversion. The mixture was evaporated, treated with sat. aq. $NaHCO_3$ (20 mL) and extracted with EtOAc (2×20 mL). The organic layers were dried over $Na_2SO_4$, filtered and solvents were evaporated. The residue was purified by flash chromatography (silica gel, 40 g, eluted with $CH_2Cl_2$/EtOAc in heptane 10% to 40% to 70%) to give the title compound (344 mg, 92%) as light yellow solid. MS (ESI): 321.1 ($[M+H]^+$).

b) 6-Chloro-5-(2,6-difluorophenyl)-7-methyl-1-(tritritiomethyl)-3H-1,4-benzodiazepin-2-one To a solution of [$^3$H]methyl nosylate (1.85 GBq, 50 mCi, 0.61 μmol) in THF (200 μL) were added the N-desmethyl precursor 6-chloro-5-(2,6-difluorophenyl)-7-methyl-1,3-dihydro-1,4-benzodiazepin-2-one (0.43 mg, 1.34 μmol) dissolved in THE (200 μL) and 10 equivalents of sodium tert-butylate (0.5 M in THF, 13.4 μmol). After stirring for 4 h at room temperature the reaction mixture was treated with $H_2O$, evaporated, and the crude product was purified by HPLC (X-Terra Prep RP-18, 10×150 mm, MeCN/$H_2O$ (containing 5% of MeCN) 40:60.4 ml/min, 230 nm). The pure tritium-labeled compound was isolated by solid phase extraction (Sep-Pak Plus C18) and eluted from the cartridge as ethanolic solution to yield 1.6 GBq (43.2 mCi) of the target compound in >99% radio-chemical purity and a specific activity of 2.49 TBq/mmol (67.3 Ci/mmol) as determined by mass spectrometry (MS). The identity of the labeled compound was confirmed by HPLC (by co-injecting the unlabeled reference standard) and by MS.

MS: m/z=335 $[M(H)+H]^+$ (16%), 337 $[M(^3H)+H]^+$ (0%), 339 $[M(^3H_2)+H]^+$ (16%), 341 $[M(^3H_3)+H]^+$ (68%).

Membrane Preparation and Binding Assay for γ2-Containing $GABA_A$ Subtypes

The affinity of compounds at $GABA_A$ γ2 subunit-containing receptors was measured by competition for [$^3$H]Flumazenil (81.1 Ci/mmol; Roche) binding to HEK293F cells expressing human (transiently transfected) receptors of composition α1β3γ2.

Harvested pellets from HEK293F cells expressing the different $GABA_A$ γ2 receptor subtypes were resuspended in Mannitol Buffer pH 7.2-7.4 and processed as described above for the cells expressing the $GABA_A$ γ1 subunit-containing receptors.

Radioligand binding assays were carried out in a volume of 200 μL (96-well plates) which contained 100 μL of cell membranes, [$^3$H]Flumazenil at a concentration of 1 nM and the test compound in the range of $0.1×10^{-9}$ to $30×10^{-6}$ M. Nonspecific binding was defined by $10^{-5}$ M Diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Exel-Fit (Microsoft) and are the means of two determinations.

The compounds of the accompanying examples were tested in the above described assay, and the preferred compounds were found to possess large K, value for displacement of [$^3$H]Flumazenil from the α1β3γ2 subtype of the human $GABA_A$ receptor of 100 nM or above. Most preferred are compounds with a $K_i$ α1β3γ2 (nM)>300. In a preferred embodiment the compounds of the invention are binding selective for the γ1 subunit-containing $GABA_A$ receptors relative to γ2 subunit-containing $GABA_A$ receptors. In particular, compounds of the present invention have γ2/γ1 selectivity ratio defined as "$K_i$ α1β3γ2 (nM)/$K_i$ α2βγ1 (nM)" (above 10-fold, or LogSel defined as "Log[$K_i$ α1β3γ2 (nM)/$K_i$ α2βγ1 (nM)]" above 1. Representative test results, obtained by the above described assay measuring binding affinity to HEK293 cells expressing human (h) receptors, are shown in the Table 1 below.

TABLE 1

| Example | Ki h-$GABA_A$ α5β2γ1 (nM) | Ki h-$GABA_A$ α2β2γ1 (nM) | Ki h-$GABA_A$ α1β2γ1 (nM) | Ki h-$GABA_A$ α1β3γ2 (nM) | γ2/γ1 Selectivity Ratio | LogSel |
|---|---|---|---|---|---|---|
| 30 | 2.6 | 43.6 | 65.0 | 582.2 | 13.3 | 1.13 |
| 31 | 2.8 | 41.0 | 39.7 | 706.8 | 17.3 | 1.24 |
| 32 | 1.3 | 10.5 | 33.3 | 1030.2 | 98.2 | 1.99 |
| 35 | 8.4 | 78.6 | 639.9 | 2801.5 | 35.7 | 1.55 |
| 51 | 0.8 | 4.9 | 9.0 | 393.0 | 79.5 | 1.90 |
| 52 | 1.1 | 5.7 | 10.2 | 637.6 | 112.4 | 2.05 |
| 53 | 1.1 | 3.0 | 14.4 | 246.4 | 82.0 | 1.91 |
| 56 | 0.8 | 4.6 | 3.8 | 850.5 | 186.8 | 2.27 |
| 63 | 5.6 | 39.4 | 332.6 | 4081.1 | 103.5 | 2.02 |
| 64 | 0.5 | 13.2 | 11.5 | 602.2 | 45.8 | 1.66 |
| 66 | 8.0 | 97.8 | 231.3 | 3277.5 | 33.5 | 1.53 |
| 67 | 3.2 | 26.5 | 188.4 | 1420.0 | 53.5 | 1.73 |
| 68 | 7.0 | 38.8 | 359.2 | 1062.4 | 27.4 | 1.44 |
| 73 | 2.0 | 8.8 | 23.5 | 768.3 | 87.5 | 1.94 |
| 74 | 2.6 | 17.3 | 28.3 | 1865.2 | 107.6 | 2.03 |
| 75 | 0.8 | 5.3 | 8.3 | 202.0 | 38.0 | 1.58 |
| 76 | 3.6 | 24.9 | 44.6 | 530.5 | 21.3 | 1.33 |
| 80 | 3.0 | 23.6 | 42.6 | 1070.2 | 45.3 | 1.66 |
| 81 | 4.3 | 36.3 | 100.8 | 1561.9 | 43.0 | 1.63 |
| 82 | 0.6 | 10.6 | 12.8 | 260.8 | 24.6 | 1.39 |
| 83 | 2.7 | 23.2 | 127.7 | 852.7 | 36.8 | 1.57 |
| 84 | 6.5 | 71.3 | 97.1 | 1205.3 | 16.9 | 1.23 |
| 85 | 3.3 | 53.0 | 63.6 | 705.2 | 13.3 | 1.12 |
| 86 | 1.4 | 4.4 | 5.9 | 860.0 | 195.1 | 2.29 |
| 87 | 2.1 | 7.5 | 8.0 | 531.5 | 70.9 | 1.85 |
| 88 | 3.6 | 10.9 | 34.5 | 1453.3 | 133.6 | 2.13 |
| 89 | 4.3 | 77.0 | 106.2 | 1464.1 | 19.0 | 1.28 |
| 92 | 1.8 | 21.9 | 48.3 | 2229.2 | 102.0 | 2.01 |
| 93 | 3.1 | 39.1 | 85.1 | 5955.5 | 152.1 | 2.18 |
| 94 | 2.0 | 8.0 | 10.3 | 608.7 | 76.4 | 1.88 |
| 95 | 1.5 | 14.2 | 24.7 | 465.8 | 32.7 | 1.51 |
| 96 | 3.0 | 13.9 | 27.9 | 473.3 | 34.1 | 1.53 |
| 97 | 2.5 | 27.1 | 33.6 | 425.2 | 15.7 | 1.19 |
| 98 | 4.4 | 72.0 | 57.6 | 1464.6 | 20.3 | 1.31 |
| 99 | 3.2 | 55.4 | 63.4 | 2016.9 | 36.4 | 1.56 |
| 100 | 3.4 | 19.8 | 34.0 | 288.0 | 14.6 | 1.16 |
| 101 | 1.0 | 26.4 | 14.3 | 494.7 | 18.8 | 1.27 |
| 102 | 0.8 | 8.0 | 6.6 | 277.6 | 34.7 | 1.54 |
| 103 | 5.4 | 50.4 | 49.8 | 3377.7 | 67.0 | 1.83 |
| 105 | 20.1 | 99.3 | ND | 7337.0 | 73.9 | 1.87 |
| 106 | 4.3 | 71.3 | ND | 7635.3 | 107.1 | 2.03 |
| 107 | 3.0 | 68.3 | ND | 3532.0 | 51.8 | 1.71 |
| 108 | 2.0 | 47.0 | ND | 2369.5 | 50.4 | 1.70 |
| 109 | 3.7 | 65.8 | ND | 753.5 | 11.5 | 1.06 |

Functional Expression of $GABA_A$ Receptors:

*Xenopus* Oocytes Preparation

*Xenopus laevis* oocytes at maturation stages V-VI were used for the expression of cloned mRNA encoding $GABA_A$ receptor subunits. Oocytes ready for RNA micro-injection were bought from Ecocyte, Castrop-Rauxel, Germany and stored in modified Barth's medium (composition in mM: NaCl 88, KCl 1, $NaHCO_3$ 2.4, HEPES 10, $MgSO_4$ 0.82, $CaNO_3$ 0.33, $CaCl_2$ 0.33, pH=7.5) at 20° C. until the experiment.

*Xenopus* Oocytes Microinjection

Oocytes were plated in 96-well plates for microinjection using the Roboinject automated instrument (MultiChannel-Systems, Reutlingen, Germany). Approximately 50 nL of an aqueous solution containing the RNA transcripts for the subunits of the desired $GABA_A$ receptor subtype was injected into each oocyte. RNA concentrations ranged between 20 and 200 pg/μL/subunit and were adjusted in pilot experiments to obtain GABA responses of a suitable size and a maximal effect of Flunitrazepam, Triazolam and Midazolam, reference benzodiazepine positive allosteric modulators (PAM) at the $GABA_A$ receptor benzodiazepine (BZD) binding site. Oocytes were kept in modified Barth's medium (composition in mM: NaCl 88, KCl 1, $NaHCO_3$ 4, HEPES 10, $MgSO_4$ 0.82, $CaNO_3$ 0.33, $CaCl_2$ 0.33, pH=7.5) at 20° C. until the experiment.

Electrophysiology

Electrophysiological experiments were performed using the Roboocyte instrument (MultiChannelSystems, Reutlingen, Germany) on days 3 to 5 after the micro-injection of mRNA. During the experiment the oocytes were constantly superfused by a solution containing (in mM) NaCl 90, KCl 1, HEPES 5, $MgCl_2$ 1 $CaCl_2$ 1 (pH 7.4). Oocytes were impaled by two glass microelectrodes (resistance: 0.5-0.8 MΩ) which were filled with a solution containing KCl 1M+K-acetate 1.5 M and voltage-clamped to −80 mV. The recordings were performed at room temperature using the Roboocyte two-electrode voltage clamp system (Multichannelsystem). After an initial equilibration period of 1.5 min GABA was added for 1.5 min at a concentration evoking approximately 20% of a maximal current response ($EC_{20}$). After another rest interval of 2.5 min GABA was again added evoking a response of similar amplitude and shape. 0.5 min after the onset of this second GABA application the test compound, at a concentration corresponding to approximatively 30-fold its $K_i$ α2β2γ1, was added while GABA was still present. Current traces were recorded at a digitization rate of 10 Hz during and shortly before and after the GABA application.

Each compound and concentration was tested on at least 3 oocytes. Different oocytes were used for different compound concentrations. The reference PAMs, Flunitrazepam, Triazolam and Midazolam, potentiated the GABA-induced current in α2βγ1 $GABA_A$ receptor subtype expressing oocytes by approximatively 60%.

Data Analysis

For the analysis, the digitized current traces of the first and second GABA response were superimposed and, if necessary, rescaled to equal maximal amplitudes. The ratio between the two responses during the time interval of test compound application was calculated point by point. The extremum of the resulting "ratio trace" was taken as the efficacy ("Fold increase") of the compound expressed as "% modulation of GABA $EC_{20}$" (100*(Fold increase−1)).

The results are shown in Table 2.

TABLE 2

| Example | Ki h-$GABA_A$ α2β2γ1 (nM) | Fold increase h-GABA-A α2β2γ1 oocyte @ 30-fold Ki | Efficacy (GABA)% |
|---|---|---|---|
| 30 | 43.6 | 1.57 | 57 |
| 31 | 41.0 | 1.74 | 74 |
| 32 | 10.5 | 2.05 | 105 |

TABLE 2-continued

| Example | Ki h-$GABA_A$ α2β2γ1 (nM) | Fold increase h-GABA-A α2β2γ1 oocyte @ 30-fold Ki | Efficacy (GABA)% |
|---|---|---|---|
| 35 | 78.6 | 2.08 | 108 |
| 51 | 4.9 | 1.56 | 56 |
| 52 | 5.7 | 2.00 | 100 |
| 53 | 3.0 | 1.32 | 32 |
| 56 | 4.6 | 1.78 | 78 |
| 63 | 39.4 | 9.91 | 891 |
| 64 | 13.2 | 1.74 | 74 |
| 66 | 97.8 | 2.43 | 143 |
| 67 | 26.5 | 1.69 | 69 |
| 68 | 38.8 | 2.09 | 109 |
| 73 | 8.8 | 2.05 | 105 |
| 74 | 17.3 | 1.62 | 62 |
| 75 | 5.3 | 1.57 | 57 |
| 76 | 24.9 | 1.52 | 52 |
| 80 | 23.6 | 1.59 | 59 |
| 81 | 36.3 | 1.46 | 46 |
| 82 | 10.6 | 1.45 | 45 |
| 83 | 23.2 | 2.02 | 102 |
| 84 | 71.3 | 3.03 | 203 |
| 85 | 53.0 | 2.14 | 114 |
| 86 | 4.4 | 1.80 | 80 |
| 87 | 7.5 | 1.42 | 42 |
| 88 | 10.9 | 2.05 | 105 |
| 89 | 77.0 | 1.88 | 88 |
| 92 | 21.9 | 1.92 | 92 |
| 93 | 39.1 | 2.69 | 169 |
| 94 | 8.0 | 1.47 | 47 |
| 95 | 14.2 | 1.53 | 53 |
| 96 | 13.9 | 1.52 | 52 |
| 97 | 27.1 | 2.48 | 148 |
| 98 | 72.0 | 2.07 | 107 |
| 99 | 55.4 | 2.35 | 135 |
| 100 | 19.8 | 1.64 | 64 |
| 101 | 26.4 | 2.19 | 119 |
| 102 | 8.0 | 1.89 | 89 |
| 103 | 50.4 | 2.23 | 123 |
| 105 | 99.3 | 1.75 | 75 |
| 106 | 71.3 | 2.21 | 121 |
| 107 | 68.3 | 2.47 | 147 |
| 108 | 47.0 | 1.94 | 94 |
| 109 | 65.8 | 3.30 | 230 |

Reference Compounds

The reference compounds (classical marketed benzodiazepines) and their structural analogues listed below were also tested for their affinity towards the $GABA_A$ receptor α1β2γ1 and α2β2γ1 subtypes as well as in the $GABA_A$ receptor α1β3γ2 subtype. The results are shown in Table 3.

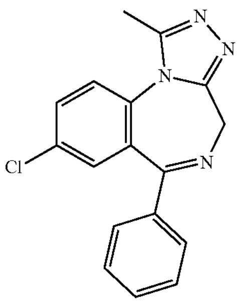

Alprazolam

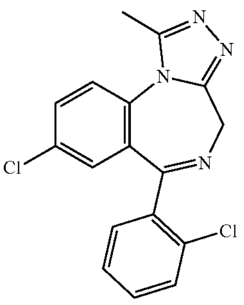

Triazolam

-continued

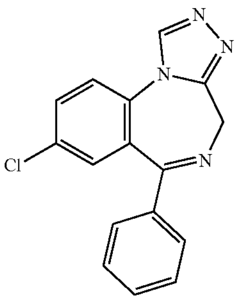

Estazolam

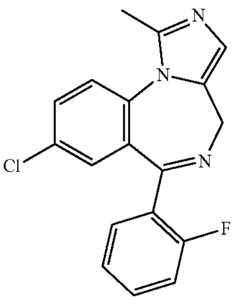

Midazolam

RE-A

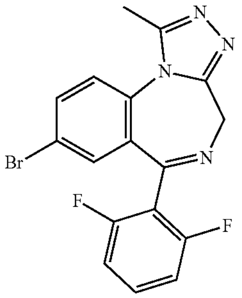

RE-B

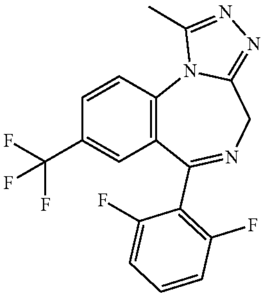

RE-C

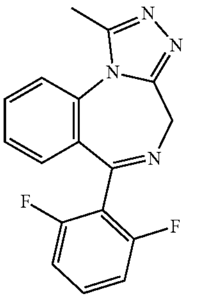

RE-D

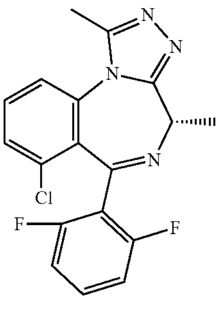

TABLE 3

| Example | Ki h-GABA$_A$ α1β2γ1 (nM) | Ki h-GABA$_A$ α2β2γ1 (nM) | Ki h-GABA$_A$ α1β3γ2 (nM) | γ2/γ1 Selectivity Ratio | LogSel |
|---|---|---|---|---|---|
| Alprazolam | 5923 | 3945 | 19.6 | 0.0050 | −2.3 |
| Triazolam | 44.2 | 46.2 | 1.5 | 0.032 | −1.5 |
| Estazolam | ND | 3182 | 28.4 | 0.0089 | −2.0 |
| Midazolam | 1153.2 | 737.7 | 5.0 | 0.0068 | −2.2 |
| RE-A | ND | 32.1 | 5.6 | 0.18 | −0.74 |
| RE-B | ND | 68.4 | 15.6 | 0.23 | −0.64 |
| RE-C | ND | 626.7 | 5.8 | 0.0092 | −2.0 |
| RE-D | ND | 453.9 | 1005.5 | 2.215 | 0.35 |
| Example 30 | 65.0 | 43.6 | 582.2 | 13.3 | 1.1 |
| Example 51 | 9.0 | 4.9 | 393.0 | 80 | 1.9 |
| Example 86 | 5.9 | 4.4 | 860.0 | 195 | 2.3 |

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Preparation of Pharmaceutical Compositions Comprising Compounds of the Invention:

Tablets of the following composition are manufactured in the usual manner:

| | mg/tablet | | | |
|---|---|---|---|---|
| Ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| | mg/capsule | | | |
|---|---|---|---|---|
| Ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions of the following composition are manufactured:

| Ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

Building Block A 7-bromo-6-chloro-5-(2,6-difluorophenyl)-1,3-dihydro-1,4-benzodiazepin-2-one

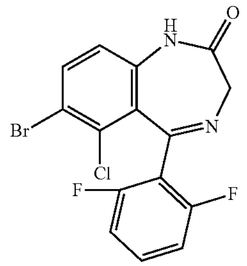 [SMILES: O=C1CN=C(c2c(F)cccc2F)c2c(ccc(Br)c2Cl)N1]

a) 5-chloro-2-methyl-3,1-benzoxazin-4-one

A solution of 2-amino-6-chlorobenzoic acid (250 g, 1.46 mol) in acetic anhydride (1250 mL) was stirred at 140° C. for 2 h. The reaction mixture was concentrated in vacuo. The resulting crude residue was suspended in ethyl acetate (1000 mL), stirred for 30 min, filtered and dried in vacuo to afford the title compound (238 g, 84%) as a grey solid. $^1H$ NMR (DMSO-$d_6$, 400 MHz): δ: 7.80 (app t, J=8.0 Hz, 1H), 7.62 (d, J=8.0 Hz, 1H), 7.49 (d, J=7.6 Hz, 1H), 2.36 (s, 3H).

b) N-[3-chloro-2-(2,6-difluorobenzoyl)phenyl]acetamide

To a solution of 5-chloro-2-methyl-3,1-benzoxazin-4-one (100 g, 511.2 mmol) and 2-bromo-1,3-difluorobenzene (118.4 g, 613.5 mmol) in tetrahydrofuran (1000 mL) was added dropwise i-PrMgCl LiCl (1.3 M, 500 mL, 650 mmol) at −70° C. under nitrogen. The mixture was allowed to warm up to room temperature within 1 h, quenched with saturated aqueous ammonium chloride (1500 mL) and extracted with ethyl acetate (2×1500 mL). The organic phase was washed with brine (2000 mL), dried over sodium sulfate and concentrated in vacuo. The residue was suspended in ethyl acetate (150 mL). The resulting suspension was stirred at room temperature for 20 min, filtered and dried in vacuo to afford the title compound (113 g, 71%) as an off-white solid. $^1H$ NMR (DMSO-$d_6$, 400 MHz): δ: 9.85 (s, 1H), 7.65-7.45 (m, 1H), 7.40 (t, J=7.2 Hz, 1H), 7.38-7.34 (m, 2H), 7.16 (t, J=8.8 Hz, 2H), 1.85 (s, 3H).

c) (2-amino-6-chloro-phenyl)-(2,6-difluorophenyl) methanone

To a solution of N-[3-chloro-2-(2,6-difluorobenzoyl)phenyl]acetamide (113 g, 364.9 mmol) in ethanol (250 mL) was added aqueous hydrochloric acid (12 M, 200 mL). The reaction mixture was stirred at 100° C. for 1 h, then diluted with ethyl acetate (1100 mL). The organic phase was washed with water (1100 mL), saturated aqueous sodium bicarbonate (1100 mL) and brine (1100 mL), dried over sodium sulfate and concentrated in vacuo. Petroleum ether (120 mL)

was added to the crude and the suspension was stirred at room temperature for 20 min. The solid was filtered and dried to afford the title compound (88 g, 90%) as a yellow solid. $^1$H NMR (DMSO-$d_6$, 400 MHz): δ: 7.62-7.56 (m, 1H), 7.21-7.15 (m, 3H), 6.83 (d, J=7.6 Hz, 1H), 6.74 (s, 2H), 6.58 (d, J=7.6 Hz, 1H).

d) (6-amino-3-bromo-2-chloro-phenyl)-(2,6-difluorophenyl)methanone

To a solution of (2-amino-6-chloro-phenyl)-(2,6-difluorophenyl)methanone (88.0 g, 328.8 mmol) in dichloromethane (225 mL) and N,N-dimethylformamide (225 mL) was added 1-bromopyrrolidine-2,5-dione (64.4 g, 362 mmol) at 0° C. The reaction mixture was stirred at 30° C. for 1 h. The mixture was diluted with dichloromethane (600 mL) and washed with water (500 mL) and brine (4×500 mL), dried over sodium sulfate and concentrated in vacuo. The residue was purified by chromatography (silica, petroleum ether/ethyl acetate, 1:0 to 2:1). The solid was suspended in petroleum ether (200 mL) and stirred at room temperature for 20 min. The suspension was filtered and the solid was dried in vacuo to afford the title compound (96.0 g, 84%) as a yellow solid. MS: 345.9 ([{$^{79}$Br, $^{35}$Cl}M+H]$^+$), 347.8 ([{$^{81}$Br, $^{35}$Cl or $^{79}$Br, $^{37}$Cl}M+H]$^+$), ESI pos.

e) 7-bromo-6-chloro-5-(2,6-difluorophenyl-1,3-dihydro-1,4-benzodiazepin-2-one

To a solution of (6-amino-3-bromo-2-chloro-phenyl)-(2,6-difluorophenyl)methanone (25.0 g, 72.1 mmol) in pyridine (625 mL) was added ethyl 2-aminoacetate hydrochloride (70.5 g, 505 mmol). The reaction mixture was stirred at 135° C. for 36 h. The reaction mixture was concentrated in vacuo to remove pyridine. The residue was diluted with ethyl acetate (2000 mL) and washed with HCl (1.0 M, 3×1500 mL), water (2000 mL) and brine (2×1000 mL), dried over sodium sulfate, filtered and concentrated in vacuo. The crude product was purified by flash column chromatography (silica, petroleum ether/ethyl acetate 10:1 to 2:1) to afford the title compound (10.1 g, 12%) as an off-white solid. MS: 385.0 ([{$^{79}$Br, $^{35}$Cl}M+H]$^+$), ESI pos.

Building Block B

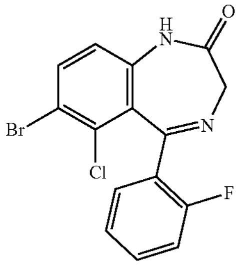 [SMILES: O=C1CN=C(c2ccccc2F)c2c(ccc(Br)c2Cl)N1]

7-bromo-6-chloro-5-(2-fluorophenyl)-1,3-dihydro-1,4-benzodiazepin-2-one a) N-[3-chloro-2-(2-fluorobenzoyl)phenyl]acetamide To a solution of 5-chloro-2-methyl-3,1-benzoxazin-4-one (20.0 g, 102.3 mmol) and 1-bromo-2-fluorobenzene (17.9 g, 102.3 mmol) in tetrahydrofuran (600 mL) at −70° C. was added dropwise n-BuLi in tetrahydrofuran (2.5 M, 49 mL, 123 mmol). The reaction mixture was stirred at −60° C. for 1 h, then quenched with aqueous ammonium chloride (200 mL). The aqueous layer was extracted with tetrahydrofuran (2×250 mL) and ethyl acetate (2×250 mL). The combined organic phase was washed with brine (200 mL), dried over sodium sulfate and concentrated in vacuo. Purification by flash column chromatography (silica, petroleum ether/ethyl acetate 20:1 to 3:1) afforded the title compound (21 g, 70%) as a white solid. MS: 292.3 ([M+H]$^+$), ESI pos.

b) (2-amino-6-chloro-phenyl)-(2-fluorophenyl)methanone

In analogy to experiment of building block A c, N-[3-chloro-2-(2-fluorobenzoyl)phenyl]acetamide was converted into the title compound (10 g, 58%) which was obtained as a yellow solid. MS: 250.1 ([M+H]$^+$), ESI pos.

c) (6-amino-3-bromo-2-chloro-phenyl)-(2-fluorophenyl)methanone

In analogy to experiment of building block A d, (2-amino-6-chloro-phenyl)-(2-fluorophenyl)methanone was converted into the title compound (32.4 g, 70%) which was obtained as a yellow solid. MS: 327.9 ([{$^{79}$Br, $^{35}$Cl}M+H]$^+$), 330.0 ([{$^{81}$Br, $^{35}$Cl or $^{79}$Br, $^{37}$Cl}M+H]$^+$), ESI pos.

d) 7-bromo-6-chloro-5-(2-fluorophenyl-1,3-dihydro-1,4-benzodiazepin-2-one

To a solution of (6-amino-3-bromo-2-chloro-phenyl)-(2-fluorophenyl)methanone (35.0 g, 98.3 mmol) in pyridine (210 mL) was added ethyl 2-aminoacetate hydrochloride (96.0 g, 688 mmol) at 90° C. The reaction mixture was stirred at 110° C. for 16 h. The reaction mixture was cooled down to room temperature and most of pyridine was removed in vacuo. The residue was diluted with ethyl acetate (1250 mL). The organic phase was washed with aqueous HCl (1.0 M, 1250 mL), water (500 mL) and brine (1000 mL), dried over sodium sulfate, filtered and concentrated in vacuo. The crude was purified by flash column chromatography (silica, petroleum ether/ethyl acetate 1:0, 25:1, 1:1). The product was dissolved in ethyl acetate (15 mL). Petroleum ether (45 mL) was added dropwise to get a white slurry. The solid was collected by filtration and dried in vacuo to afford the title compound (30.4 g, 39%) as an off-white solid. MS: 367.0 ([{$^{79}$Br, $^{35}$Cl}M+H]$^+$), 368.9 ([{$^{81}$Br, $^{35}$Cl or $^{79}$Br, $^{37}$Cl}M+H]$^+$), ESI pos.

Building Block G (rac)-7-bromo-6-chloro-5-(2-fluorophenyl)-3-methyl-1,3-dihydro-1,4-benzodiazepin-2-one

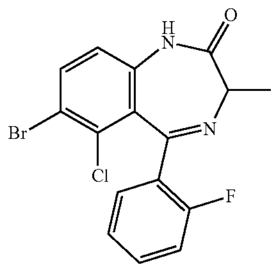 [SMILES: CC1N=C(c2ccccc2F)c2c(ccc(Br)c2Cl)NC1=O]

a) (rac)-tert-butyl N-[2-[4-bromo-3-chloro-2-(2-fluorobenzoyl)anilino]-1-methyl-2-oxo-ethyl]carbamate To a solution of (6-amino-3-bromo-2-chloro-phenyl)-(2-fluorophenyl)methanone (2.0 g, 6.09 mmol) and 2-(tert-butoxycarbonylamino)propanoic acid (1.73 g, 9.13 mmol) in pyridine (20 mL) was added phosphoryl chloride (1.22 g, 7.98 mmol) slowly at −5° C. The reaction mixture was stirred at −5° C. for 1 h, before being slowly poured into water (200 mL) and extracted with ethyl acetate (2×100 mL). The combined organic phase was washed with brine (2×50 mL), dried over sodium sulfate and concentrated in vacuo. The residue was purified by flash column chromatography (petroleum ether/ethyl acetate 5:1) to afford the title compound (2.95 g, 97%) as a yellow solid. MS: 399.1 ([{$^{79}$Br, $^{35}$Cl}M-$C_4H_8$—$CO_2$+H]$^+$), 401.0 ([{$^{81}$Br, $^{35}$Cl or $^{79}$Br, $^{37}$Cl}M–$C_4H_8$—$CO_2$+H]$^+$), ESI pos.

b) (rac)-2-amino-N-[4-bromo-3-chloro-2-(2-fluorobenzoyl)phenyl]propanamide

To a solution of (rac)-tert-butyl N-[2-[4-bromo-3-chloro-2-(2-fluorobenzoyl)anilino]-1-methyl-2-oxo-ethyl]carbamate (2.9 g, 5.8 mmol) in dichloromethane (14.5 mL) was slowly added hydrochloric acid (4.0 M in dioxane, 14.5 mL, 58.0 mmol). The reaction mixture was stirred at 25° C. for 2 h. Saturated aqueous sodium bicarbonate was added slowly until pH>8, then the mixture was extracted with dichloromethane (3×100 mL). The combined organic phase was washed with brine (100 mL), dried over sodium sulfate and concentrated in vacuo to afford the title compound (2.2 g, 92%) as a yellow oil. MS: 399.0 ([{$^{79}$Br, $^{35}$Cl}M+H]$^+$), 401.0 ([{$^{81}$Br, $^{35}$Cl or $^{79}$Br, $^{37}$Cl}M+H]$^+$), ESI pos.

c) (rac)-7-bromo-6-chloro-5-(2-fluorophenyl)-3-methyl-1,3-dihydro-1,4-benzodiazepin-2-one To a solution of (rac)-2-amino-N-[4-bromo-3-chloro-2-(2-fluorobenzoyl)phenyl]propanamide (2.2 g, 5.5 mmol) in ethanol (20 mL) was added acetic acid (4 mL). The reaction mixture was stirred at 80° C. for 16 h, then concentrated in vacuo. The formed crystals were filtered, purified by trituration with ethyl acetate (15 mL), then collected by filtration and dried in vacuo to afford the title compound (1.6 g, 76%) as a yellow solid. MS: 381.0 ([{$^{79}$Br, $^{35}$Cl}M+H]$^+$), 383.0 ([{$^{81}$Br, $^{35}$Cl or $^{79}$Br, $^{37}$Cl}M+H]$^+$), ESI pos.

Building Block L (3S)-7-bromo-6-chloro-5-(2,6-difluorophenyl)-3-methyl-1,3-dihydro-1,4-benzodiazepin-2-one

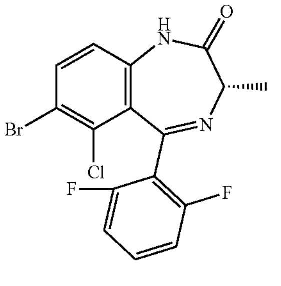 [SMILES: C[C@@H]1N=C(c2c(F)cccc2F)c2c(ccc(Br)c2Cl)NC1=O]

a) tert-butyl N-[(1S)-2-[4-bromo-3-chloro-2-(2,6-difluorobenzoyl)anilino]-1-methyl-2-oxo-ethyl]carbamate In analogy to experiment of building block G a, (6-amino-3-bromo-2-chloro-phenyl)-(2,6-difluorophenyl)methanone using (2S)-2-(tert-butoxycarbonylamino)propanoic acid was converted into the title compound (1.50 g, 98%) which was obtained as a yellow solid. MS: 418.7 ([{$^{81}$Br, $^{35}$Cl or $^{79}$Br, $^{37}$Cl}M–$C_4H_8$—$CO_2$+H]$^+$), 540.7 ([{$^{81}$Br, $^{35}$Cl or $^{79}$Br, $^{37}$Cl}M+Na]$^+$), ESI pos.

b) (2S)-2-amino-N-[4-bromo-3-chloro-2-(2,6-difluorobenzoyl)phenyl]propanamide

In analogy to experiment of building block G b, tert-butyl N-[(1S)-2-[4-bromo-3-chloro-2-(2,6-difluorobenzoyl)anilino]-1-methyl-2-oxo-ethyl]carbamate was converted into the title compound (1.1 g, 94%) which was obtained as a yellow oil, which was used as such in the following step without further characterization.

c) (3S)-7-bromo-6-chloro-5-(2,6-difluorophenyl)-3-methyl-1,3-dihydro-1,4-benzodiazepin-2-one To a solution of (2S)-2-amino-N-[4-bromo-3-chloro-2-(2,6-difluorobenzoyl)phenyl]propanamide (960 mg, 2.30 mmol) in toluene (9.19 mL) was added silica (138 mg, 2.30 mmol). The reaction mixture was stirred at 90° C. for 15 h, then concentrated in vacuo. The residue was purified by flash column chromatography (petroleum ether/ethyl acetate 3:1) to afford the title compound (920 mg, 95%) as a yellow solid. MS: 399.1 ([{$^{79}$Br, $^{35}$Cl}M+H]$^+$), 401.1 ([{$^{81}$Br, $^{35}$Cl or $^{79}$Br, $^{37}$Cl}M+H]$^+$), ESI pos.

Building Block M (3S)-6,7-dichloro-5-(2,6-difluorophenyl)-3-methyl-1,3-dihydro-1,4-benzodiazepin-2-one

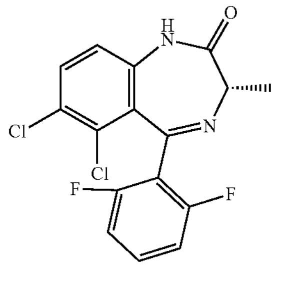 [SMILES: C[C@@H]1N=C(c2c(F)cccc2F)c2c(ccc(Cl)c2Cl)NC1=O]

a) tert-butyl N-[(1S)-2-[3,4-dichloro-2-(2,6-difluorobenzoyl)anilino]-1-methyl-2-oxo-ethyl]carbamate In analogy to experiment of building block G a, (6-amino-2,3-dichloro-phenyl)-(2,6-difluorophenyl)methanone using (2S)-2-(tert-butoxycarbonylamino)propanoic acid was converted into the title compound (5.0 g, 64%) which was obtained as a yellow foam. The crude was used as such in the following step without further characterization.

b) (2S)-2-amino-N-[3,4-dichloro-2-(2,6-difluorobenzoyl)phenyl]propanamide

In analogy to experiment of building block G b, tert-butyl N-[(1S)-2-[3,4-dichloro-2-(2,6-difluorobenzoyl)anilino]-1- methyl-2-oxo-ethyl]carbamate was converted into the title compound (3.6 g, 91%) which was obtained as a yellow oil. MS: 373.0 ([{$^{35}$Cl, $^{35}$Cl}M+H]$^+$), ESI pos.

c) (3S)-6,7-dichloro-5-(2,6-difluorophenyl)-3-methyl-1,3-dihydro-1,4-benzodiazepin-2-one In analogy to experiment of building block L c, (2S)-2-amino-N-[3,4-dichloro-2-(2,6-difluorobenzoyl)phenyl]propanamide was converted into the title compound (3.20 g, 93%) which was obtained as a yellow foam. MS: 355.0 ([{$^{35}$Cl, $^{35}$Cl}M+H]$^+$), ESI pos.

Building Block O (3S)-6,7-dichloro-5-(3-fluoro-2-pyridyl)-3-methyl-1,3-dihydro-1,4-benzodiazepin-2-one

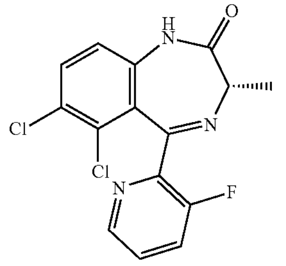 [SMILES: C[C@@H]1N=C(c2ncccc2F)c2c(ccc(Cl)c2Cl)NC1=O]

a) tert-butyl N-[(1S)-2-[3,4-dichloro-2-(3-fluoropyridine-2-carbonyl)anilino]-1-methyl-2-oxo-ethyl]carbamate In analogy to experiment of building block G a, N-[3,4-dichloro-2-(3-fluoropyridine-2-carbonyl)phenyl]acetamide using (2S)-2-(tert-butoxycarbonylamino)propanoic acid was converted into the title compound (8.6 g, 67%) as a white solid. MS: 456.0 ([{$^{35}$Cl, $^{35}$Cl}M+H]$^+$), ESI pos.

b) (2S)-2-amino-N-[3,4-dichloro-2(3-fluoropyridine-2-carbonyl)phenyl]propanamide In analogy to experiment of building block G b, tert-butyl N-[(1S)-2-[3,4-dichloro-2-(3-fluoropyridine-2-carbonyl)anilino]-1-methyl-2-oxo-ethyl]carbamate was converted into the title compound (6.6 g, 100%) which was obtained as a yellow solid. MS: 356.0 ([{$^{35}$Cl, $^{35}$Cl}M+H]$^+$), ESI pos.

c) (3S)-6,7-dichloro-5-(3-fluoro-2-pyridyl-3-methyl-1,3-dihydro-1,4-benzodiazepin-2-one In analogy to experiment of building block L c, (2S)-2-amino-N-[3,4-dichloro-2-(3-fluoropyridine-2-carbonyl)phenyl]propanamide was converted into the title compound (5.5 g, 88%) which was obtained as a yellow solid. MS: 338.0 ([{$^{35}$Cl, $^{35}$Cl}M+H]$^+$), ESI pos.

Building Block Q (3S)-6-bromo-7-chloro-5-(2,6-difluorophenyl)-3-methyl-1,3-dihydro-1,4-benzodiazepin-2-one

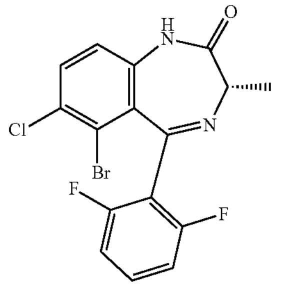 [SMILES: C[C@@H]1N=C(c2c(F)cccc2F)c2c(ccc(Cl)c2Br)NC1=O]

a) N-[3-bromo-4-chloro-2-(2,6-difluorobenzoyl)phenyl]acetamide

In analogy to experiment of building block A d, N-(3-bromo-2-(2,6-difluorobenzoyl)phenyl)acetamide using 1-chloropyrrolidine-2,5-dione was converted into the title compound (10.1 g, 70%) which was obtained as a light yellow solid. MS: 388.0 ([{$^{79}$Br, $^{35}$Cl}M+H]$^+$), 390.1 ([{$^{81}$Br, $^{35}$Cl or $^{79}$Br, $^{37}$Cl}M+H]$^+$), ESI pos.

b) (6-amino-2-bromo-3-chloro-phenyl)-(2,6-difluorophenyl)methanone

In analogy to experiment of building block A c, N-[3-bromo-4-chloro-2-(2,6-difluorobenzoyl)phenyl]acetamide was converted into the title compound (8.2 g, 92%) which was obtained as a yellow solid. MS: 346.0 ([{$^{79}$Br, $^{35}$Cl}M+H]$^+$), 348.0 ([{$^{81}$Br, $^{35}$Cl or $^{79}$Br, $^{37}$Cl}M+H]$^+$), ESI pos.

c) tert-butyl N-[(1S)-2-[3-bromo-4-chloro-2-(2,6-difluorobenzoyl)anilino]-1-methyl-2-oxo-ethyl]carbamate In analogy to experiment of building block G a, (6-amino-2-bromo-3-chloro-phenyl)-(2,6-difluorophenyl)methanone using (2S)-2-(tert-butoxycarbonylamino)propanoic acid was converted into the title compound (8.64 g, 69%) which was obtained as a yellow solid. MS: 515.2 ([{$^{79}$Br, $^{35}$Cl}M−H]$^-$), 517.1 ([{$^{81}$Br, $^{35}$Cl or $^{79}$Br, $^{37}$Cl}M−H]$^-$), ESI neg.

d) (2S)-2-amino-N-[3-bromo-4-chloro-2-(2,6-difluorobenzoyl)phenyl]propanamide

In analogy to experiment of building block G b, tert-butyl N-[(1S)-2-[3-bromo-4-chloro-2-(2,6-difluorobenzoyl)anilino]-1-methyl-2-oxo-ethyl]carbamate was converted into the title compound (6.27 g, 90%) which was obtained as a light brown oil. MS: 417.1 ([{$^{79}$Br, $^{35}$Cl}M+H]$^+$), 419.0 ([{$^{81}$Br, $^{35}$Cl or $^{79}$Br, $^{37}$Cl}M+H]$^+$), ESI pos.

e) (3S)-6-bromo-7-chloro-5-(2,6-difluorophenyl)-3-methyl-1,3-dihydro-1,4-benzodiazepin-2-one In analogy to experiment of building block L c, (2S)-2-amino-N-[3-bromo-4-chloro-2-(2,6-difluorobenzoyl)phenyl]propanamide was converted into the title compound (3.98 g, 68%) which was obtained as a yellow solid. MS: 399.1 ([{$^{79}Br$, $^{35}Cl$}M+H]$^+$), 401.0 ([{$^{81}Br$, $^{35}Cl$ or $^{79}Br$, $^{37}Cl$}M+H]$^+$), ESI pos.

Building Block R (3S)-7-bromo-6-chloro-5-(3-fluoro-2-pyridyl)-3-methyl-1,3-dihydro-1,4-benzodiazepin-2-one

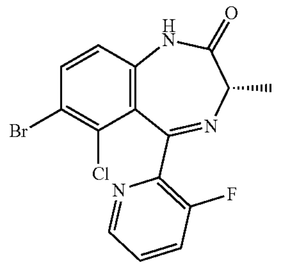

a) tert-butyl N-[(1S)-2-[4-bromo-3-chloro-2(3-fluoropyridine-2-carbonyl)anilino]-1-methyl-2-oxo-ethyl]carbamate In analogy to experiment of building block G a, (6-amino-3-bromo-2-chloro-phenyl)-(3-fluoro-2-pyridyl)methanone using (2S)-2-(tert-butoxycarbonylamino)propanoic acid was converted into the title compound (1.4 g, 97%) which was obtained as a yellow foam. The crude was used as such in the following step without further characterization.

b) (2S)-2-amino-N-[4-bromo-3-chloro-2-(3-fluoropyridine-2-carbonyl)phenyl]propanamide In analogy to experiment of building block G b, tert-butyl N-[(1S)-2-[4-bromo-3-chloro-2-(3-fluoropyridine-2-carbonyl)anilino]-1-methyl-2-oxo-ethyl]carbamate was converted into the title compound (1.1 g, 98%) which was obtained as a yellow oil. The crude was used as such in the following step without further characterization.

c) (3S)-7-bromo-6-chloro-5-(3-fluoro-2-pyridyl)-3-methyl-1,3-dihydro-1,4-benzodiazepin-2-one In analogy to experiment of building block L c, (2S)-2-amino-N-[4-bromo-3-chloro-2-(3-fluoropyridine-2-carbonyl)phenyl]propanamide was converted into the title compound (430 mg, 40%) which was obtained as a yellow solid. MS: 381.9 ([{$^{79}Br$, $^{35}Cl$}M+H]$^+$), 383.9 ([{$^{81}Br$, $^{35}Cl$ or $^{79}Br$, $^{37}Cl$}M+H]$^+$), ESI pos.

Building Block S (3S)-6-chloro-5-(2,6-difluorophenyl)-7-iodo-3-methyl-1,3-dihydro-1,4-benzodiazepin-2-one

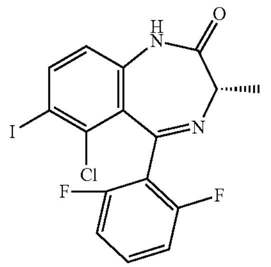 [SMILES: C[C@@H]1N=C(c2c(F)cccc2F)c2c(ccc(I)c2Cl)NC1=O]

a) tert-butyl N-[(1S)-2-[3-chloro-2-(2,6-difluorobenzoyl)-4-iodo-anilino]-1-methyl-2-oxo-ethyl]carbamate In analogy to experiment of building block G a, (6-amino-2-chloro-3-iodo-phenyl)-(2,6-difluorophenyl)methanone using (2S)-2-(tert-butoxycarbonylamino)propanoic acid was converted into the title compound (5.8 g, 81%) which was obtained as a yellow solid. MS: 465.0 ([M–$C_4H_8$—$CO_2$+H]$^+$), 509.0 ([M–$C_4H_8$+H]$^+$), ESI pos.

b) (2S)-2-amino-N-[3-chloro-2-(2,6-difluorobenzoyl)-4-iodo-phenyl]propanamide

In analogy to experiment of building block G b, tert-butyl N-[(1S)-2-[3-chloro-2-(2,6-difluorobenzoyl)-4-iodo-anilino]-1-methyl-2-oxo-ethyl]carbamate was converted into the title compound (4.7 g, 99%) which was obtained as a yellow solid. The crude was used as such in the following step without further characterization.

c) (3S)-6-chloro-5-(2,6-difluorophenyl)-7-iodo-3-methyl-1,3-dihydro-1,4-benzodiazepin-2-one In analogy to experiment of building block L c, (2S)-2-amino-N-[3-chloro-2-(2,6-difluorobenzoyl)-4-iodo-phenyl]propanamide was converted into the title compound (3.8 g, 94%) which was obtained as a yellow solid. MS: 446.8 ([M+H]$^+$), ESI pos.

Building Block T (3S)-7-bromo-6-chloro-5-(2,6-difluorophenyl)-3-ethyl-1,3-dihydro-1,4-benzodiazepin-2-one

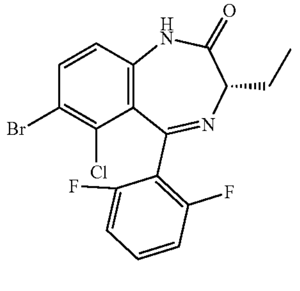 [SMILES: CC[C@@H]1N=C(c2c(F)cccc2F)c2c(ccc(Br)c2Cl)NC1=O]

a) tert-butyl N-[(1S)-1-[[4-bromo-3-chloro-2-(2,6-difluorobenzoyl)phenyl]carbamoyl]propyl]carbamate In analogy to experiment of building block G a, (6-amino-3-bromo-2-chloro-phenyl)-(2,6-difluorophenyl)methanone using (2S)-2-(tert-butoxycarbonylamino)butanoic acid was converted into the title compound (1.08 g, 68%) which was obtained as a yellow solid. MS: 433.1 ([{$^{81}$Br, $^{35}$Cl or $^{79}$Br, $^{37}$Cl}M−$C_4H_8$—$CO_2$+H]$^+$), 477.1 ([{$^{81}$Br, $^{35}$Cl or $^{79}$Br, $^{37}$Cl}M−$C_4H_8$+H]$^+$), ESI pos.

b) (2S)-2-amino-N-[4-bromo-3-chloro-2-(2,6-difluorobenzoyl)phenyl]butanamide

In analogy to experiment of building block G b, tert-butyl N-[(1S)-1-[[4-bromo-3-chloro-2-(2,6-difluorobenzoyl)phenyl]carbamoyl]propyl]carbamate was converted into the title compound (730 mg, 90%) which was obtained as a yellow oil. MS: 433.0 ([{$^{81}$Br, $^{35}$Cl or $^{79}$Br, $^{37}$Cl}M+H]$^+$), ESI pos.

c) (3S)-7-bromo-6-chloro-5-(2,6-difluorophenyl)-3-ethyl-1,3-dihydro-1,4-benzodiazepin-2-one In analogy to experiment of building block L c, (2S)-2-amino-N-[4-bromo-3-chloro-2-(2,6-difluorobenzoyl)phenyl]butanamide was converted into the title compound (650 mg, 97%) which was obtained as a light brown foam. MS: 414.9 ([{$^{81}$Br, $^{35}$Cl or $^{79}$Br, $^{37}$Cl}M+H]$^+$), ESI pos.

Building Block U (3S)-7-bromo-6-chloro-5-(2,6-difluorophenyl)-3-(methoxymethyl)-1,3-dihydro-1,4-benzodiazepin-2-one

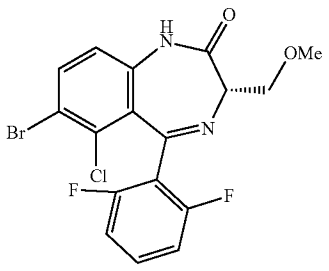 [SMILES: COC[C@@H]1N=C(c2c(F)cccc2F)c2c(ccc(Br)c2Cl)NC1=O]

a) tert-butyl N-[(1S)-2-[4-bromo-3-chloro-2-(2,6-difluorobenzoyl)anilino]-1-(methoxymethyl)-2-oxo-ethyl]carbamate In analogy to experiment of building block G a, (6-amino-3-bromo-2-chloro-phenyl)-(2,6-difluorophenyl)methanone using (2S)-2-(tert-butoxycarbonylamino)-3-methoxy-propanoic acid was converted into the title compound (4.3 g, 85%) which was obtained as a yellow solid. The crude was used as such in the following step without further characterization.

b) (2S)-2-amino-N-[4-bromo-3-chloro-2-(2,6-difluorobenzoyl)phenyl]-3-methoxy-propanamide In analogy to experiment of building block G b, tert-butyl N-[(1S)-2-[4-bromo-3-chloro-2-(2,6-difluorobenzoyl)anilino]-1-(methoxymethyl)-2-oxo-ethyl]carbamate was converted into the title compound (3.0 g, 96%) which was obtained as a yellow oil. MS: 447.0 ([{$^{79}$Br, $^{35}$Cl}M+H]$^+$), 449.1 ([{$^{81}$Br, $^{35}$Cl or $^{79}$Br, $^{37}$Cl}M+H]$^+$), ESI pos.

c) (3S)-7-bromo-6-chloro-5-(2,6-difluorophenyl-3-(methoxymethyl-1,3-dihydro-1,4-benzodiazepin-2-one In analogy to experiment of building block L c, (2S)-2-amino-N-[4-bromo-3-chloro-2-(2,6-difluorobenzoyl)phenyl]-3-methoxy-propanamide was converted into the title compound (1.9 g, 78%) which was obtained as a white solid. The crude was used as such in the following step without further characterization. MS: 429.1 ([{$^{79}$Br, $^{35}$Cl}M+H]$^+$), 431.1 ([{$^{81}$Br, $^{35}$Cl or $^{79}$Br, $^{37}$Cl}M+H]$^+$), ESI pos.

Example 30

(4S)-8-bromo-7-chloro-6-(2-fluorophenyl)-4-methyl-4H-[1,2,4]triazolo[4,3-a][1,4]benzodiazepine

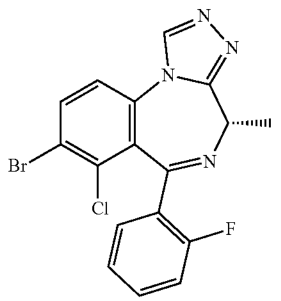 [SMILES: C[C@@H]1N=C(c2ccccc2F)c2c(ccc(Br)c2Cl)-n2cnnc21]

a) (rac)-7-bromo-6-chloro-5-(2-fluorophenyl-3-methyl-1,3-dihydro-1,4-benzodiazepine-2-thione To a suspension of (rac)-7-bromo-6-chloro-5-(2-fluorophenyl)-3-methyl-1,3-dihydro-1,4-benzodiazepin-2-one (building block G, 500 mg, 1.31 mmol) in toluene (8.33 mL) at room temperature was added Lawesson's reagent (635 mg, 1.57 mmol). The reaction mixture was stirred at 110° C. for 1 h, before being concentrated in vacuo. The crude material was purified by flash column chromatography (silica, 15-25% ethyl acetate in heptane) to afford the title compound (820 mg, 91%) which was obtained as a yellow solid. The crude was used as such in the following step without further characterization.

b) (rac)-8-bromo-7-chloro-6-(2-fluorophenyl-4-methyl-4H-[1,2,4]triazolo[4,3-a][1,4]benzodiazepine To a solution of (rac)-7-bromo-6-chloro-5-(2-fluorophenyl)-3-methyl-1,3-dihydro-1,4-benzodiazepine-2-thione (240 mg, 0.600 mmol) in butan-1-ol (3.2 mL) was added formohydrazide (108 mg, 1.81 mmol). The reaction mixture was stirred at 120° C. for 16 h. The mixture was diluted with dichloromethane (20 mL), washed with water (20 mL), brine (20 mL), dried over sodium sulfate and concentrated in vacuo. The residue was purified by preparative HPLC (TFA) to afford the title compound (250 mg, 100%) which was obtained as a white solid. MS: 404.8 ([{$^{79}$Br, $^{35}$Cl}M+H]$^+$), 406.7 ([{$^{81}$Br, $^{35}$Cl or $^{79}$Br, $^{37}$Cl}M+H]$^+$), ESI pos.

c) (4S)-8-bromo-7-chloro-6-(2-fluorophenyl)-4-methyl-4H-[1,2,4]triazolo[4,3-a][1,4]benzodiazepine (rac)-8-bromo-7-chloro-6-(2-fluorophenyl)-4-methyl-4H-[1,2,4]triazolo[4,3-a][1,4]benzodiazepine (254 mg, 0.630 mmol) was purified by SFC (Chiralcel OJ-3, 0.05% diethylamine in methanol, 5-40%) affording:

(−)-enantiopure (S)-title compound (88.1 mg) as a white solid. MS: 404.8 ([{$^{79}$Br, $^{35}$Cl}M+H]$^+$), 406.8 ([{$^{81}$Br, $^{35}$Cl or $^{79}$Br, $^{37}$Cl}M+H]$^+$), ESI pos.

(+)-enantiopure (R)-title compound (80.4 mg) as a white solid. MS: 404.9 ([{$^{79}$Br, $^{35}$Cl}M+H]$^+$), 406.8 ([{$^{81}$Br, $^{35}$Cl or $^{79}$Br, $^{37}$Cl}M+H]$^+$), ESI pos.

Example 31

8-bromo-7-chloro-6-(2,6-difluorophenyl)-4H-[1,2,4]triazolo[4,3-a][1,4]benzodiazepin-4-ol

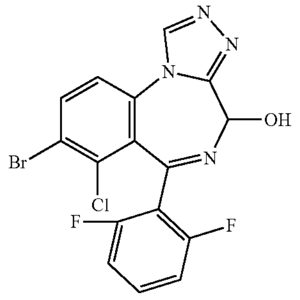 [SMILES: OC1N=C(c2c(F)cccc2F)c2c(ccc(Br)c2Cl)-n2cnnc21]

a) 7-bromo-6-chloro-5-(2,6-difluorophenyl-1,3-dihydro-1,4-benzodiazepin-2-thione To a suspension of 7-bromo-6-chloro-5-(2,6-difluorophenyl)-1,3-dihydro-1,4-benzodiazepin-2-one (building block A, 6.7 g, 17.4 mmol) in toluene (167 mL) at room temperature was added Lawesson's reagent (8.43 g, 20.9 mmol). The reaction mixture was stirred at 120° C. for 1.5 h, before being diluted with ethyl acetate (400 mL). The organic layer was washed with water (300 mL) and brine (300 mL), dried over sodium sulfate, filtered and concentrated in vacuo. The crude material was purified by flash column chromatography (silica, 15-30% ethyl acetate in heptane) to afford the title compound (6.98 g, 100%) as a yellow solid. MS: 400.8 ([{$^{79}$Br, $^{35}$Cl}M+H]$^+$), 402.9 ([{$^{81}$Br, $^{35}$Cl or $^{79}$Br, $^{37}$Cl}M+H]$^+$), ESI pos.

b) 8-bromo-7-chloro-6-(2,6-difluorophenyl)-4H-[1,2,4]triazolo[4,3-a][1,4]benzodiazepine In analogy to experiment of example 30 b, 7-bromo-6-chloro-5-(2,6-difluorophenyl)-1,3-dihydro-1,4-benzodiazepin-2-thione using formohydrazide was converted into the title compound (2.4 g, 32%) which was obtained as a white solid. MS: 409.1 ([{$^{79}$Br, $^{35}$Cl}M+H]$^+$), 411.1 ([{$^{81}$Br, $^{35}$Cl or $^{79}$Br, $^{37}$Cl}M+H]$^+$), ESI pos.

c) 8-bromo-7-chloro-6-(2,6-difluorophenyl-4H-[1,2,4]triazolo[4,3-a][1,4]benzodiazepin-4-ol To a solution of sodium bis(trimethylsilyl)amide (1.0 M in tetrahydrofuran, 0.37 mL, 0.370 mmol) in tetrahydrofuran (5 mL) was added 8-bromo-7-chloro-6-(2,6-difluorophenyl)-4H-[1,2,4]triazolo[4,3-a][1,4]benzodiazepine (100.0 mg, 0.240 mmol) at −65° C. The mixture was stirred at −65° C. for 30 min, then 2-(benzenesulfonyl)-3-phenyl-oxaziridine (97 mg, 0.370 mmol) was added. The reaction mixture was stirred at −65° C. for 2 h, before being quenched by addition of saturated aqueous ammonium chloride. The aqueous phase was extracted with ethyl acetate (2×10 mL). The combined organic layers were washed with brine (2×30 mL), filtered and concentrated in vacuo. The residue was purified by preparative HPLC (Boston Prime C18, 0.1% trifluoroacetic acid in water/acetonitrile) followed by chiral-HPLC (Daicel Chiralcel OJ-H, methanol) to afford the title compound (30 mg, 29%) as a white solid. MS: 424.9 ([{$^{79}$Br, $^{35}$Cl}M+H]$^+$), 426.8 ([{$^{81}$Br, $^{35}$Cl or $^{79}$Br, $^{37}$Cl}M+H]$^+$), ESI pos.

Example 32

(4S)-8-bromo-7-chloro-6-(2-fluorophenyl)-4-methyl-1-pyridazin-3-yl-4H-[1,2,4]triazolo[4,3-a][1,4]benzodiazepine

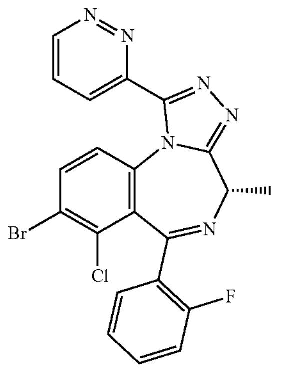 [SMILES: C[C@@H]1N=C(c2ccccc2F)c2c(ccc(Br)c2Cl)-n2c(-c3cccnn3)nnc21]

a) (rac)-8-bromo-7-chloro-6-(2-fluorophenyl-4-methyl-1-pyridazin-3-yl-4H-[1,2,4]triazolo[4,3-a][1,4]benzodiazepine In analogy to experiment of example 30 b, (rac)-7-bromo-6-chloro-5-(2-fluorophenyl)-3-methyl-1,3-dihydro-1,4-benzodiazepine-2-thione using pyridazine-3-carbohydrazide was converted into the title compound (220 mg, 75%) which was obtained as a white solid. MS: 482.9 ([{$^{79}$Br, $^{35}$Cl}M+H]$^+$), 484.8 ([{$^{81}$Br, $^{35}$Cl or $^{79}$Br, $^{37}$Cl}M+H]$^+$), ESI pos.

b) (4S)-8-bromo-7-chloro-6-(2-fluorophenyl-4-methyl-1-pyridazin-3-yl-4H-[1,2,4]triazolo[4,3-a][1,4]benzodiazepine (rac)-8-bromo-7-chloro-6-(2-fluorophenyl)-4-methyl-1-pyridazin-3-yl-4H-[1,2,4]triazolo[4,3-a][1,4]benzodiazepine (220 mg, 0.450 mmol) was purified by SFC (Chiralcel OJ-3, 0.05% diethylamine in methanol, 5-40%), followed by lyophilization affording:

(−)-enantiopure (S)-title compound (64.3 mg) as a white solid. MS: 483.1 ([{$^{79}$Br, $^{35}$Cl}M+H]$^+$), 485.1 ([{$^{81}$Br, $^{35}$Cl or $^{79}$Br, $^{37}$Cl}M+H]$^+$), ESI pos.

(+)-enantiopure (R)-title compound (61.4 mg) as a white solid. MS: 483.1 ([{$^{79}$Br, $^{35}$Cl}M+H]$^+$), 485.1 ([{$^{81}$Br, $^{35}$Cl or $^{79}$Br, $^{37}$Cl}M+H]$^+$), ESI pos.

Example 35

8-bromo-7-chloro-6-(2-fluorophenyl)-1-pyridazin-3-yl-4H-[1,2,4]triazolo[4,3-a][1,4]benzodiazepin-4-ol

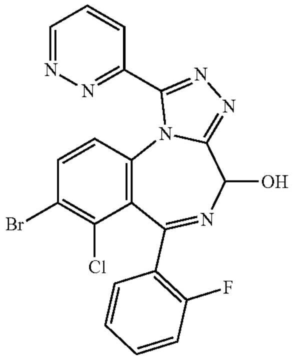 [SMILES: OC1N=C(c2ccccc2F)c2c(ccc(Br)c2Cl)-n2c(-c3cccnn3)nnc21]

a) 7-bromo-6-chloro-5-(2-fluorophenyl-1,3-dihydro-1,4-benzodiazepine-2-thione

In analogy to experiment of example 30 a, 7-bromo-6-chloro-5-(2-fluorophenyl)-1,3-dihydro-1,4-benzodiazepin-2-one was converted into the title compound (390 mg, 54%) which was obtained as a yellow solid. The crude was used as such in the following step without further characterization.

b) 8-bromo-7-chloro-6-(2-fluorophenyl)-1-pyridazin-3-yl-4H-[1,2,4]triazolo[4,3-a][1,4]benzodiazepine In analogy to experiment of example 30 b, 7-bromo-6-chloro-5-(2-fluorophenyl)-1,3-dihydro-1,4-benzodiazepine-2-thione using pyridazine-3-carbohydrazide was converted into the title compound (294 mg, 73%) which was obtained as a white solid. MS: 469.1 ([{$^{79}$Br, $^{35}$Cl}M+H]$^+$), 471.1 ([{$^{81}$Br, $^{35}$Cl or $^{79}$Br, $^{37}$Cl}M+H]$^+$), ESI pos.

c) [8-bromo-7-chloro-6-(2-fluorophenyl)-1-pyridazin-3-yl-4H-[1,2,4]triazolo[4,3-a][1,4]benzodiazepin-4-yl]acetate To a solution of 8-bromo-7-chloro-6-(2-fluorophenyl)-1-pyridazin-3-yl-4H-[1,2,4]triazolo[4,3-a][1,4]benzodiazepine (100 mg, 0.21 mmol) in acetic acid (2 mL) was added iodine (27 mg, 0.11 mmol), potassium acetate (42 mg, 0.43 mmol) and potassium persulfate (58 mg, 0.21 mmol). The reaction mixture was heated to 90° C. for 12 h, before being quenched by addition of saturated aqueous $Na_2SO_3$ (10 mL). The mixture was extracted with ethyl acetate (30 mL). The organic layer was washed with water (10 mL), dried over sodium sulfate and concentrated in vacuo. The residue was purified by flash column chromatography (silica, dichloromethane/methanol 100:1 to 80:1) to afford the title compound (55 mg, 49%) as a white solid. MS: 526.9 ([{$^{81}$Br, $^{35}$Cl}M+H]$^+$), 528.9 ([{$^{81}$Br, $^{35}$Cl or $^{79}$Br, $^{37}$Cl}M+H]$^+$), ESI pos.

d) 8-bromo-7-chloro-6-(2-fluorophenyl)-1-pyridazin-3-yl-4H-[1,2,4]triazolo[4,3-a][1,4]benzodiazepin-4-ol To a solution of [8-bromo-7-chloro-6-(2-fluorophenyl)-1-pyridazin-3-yl-4H-[1,2,4]triazolo[4,3-a][1,4]benzodiazepin-4-yl] acetate (55 mg, 0.10 mmol) in ethanol (2.75 mL) was added sodium carbonate (22 mg, 0.21 mmol). The reaction mixture was stirred at room temperature for 4 h, then filtered and concentrated in vacuo. The residue was purified by preparative TLC (dichloromethane/methanol), followed by preparative HPLC (Shim-pack C18, 0.225% trifluoroacetic acid in water/acetonitrile) and lyophilized to afford the title compound (13.1 mg, 26%) as a white solid. MS: 485.0 ([{$^{79}$Br, $^{35}$Cl}M+H]$^+$), 487.0 ([{$^{81}$Br, $^{35}$Cl or $^{79}$Br, $^{35}$Cl}M+H]$^+$), ESI pos.

Example 51

(4S)-8-bromo-7-chloro-6-(2,6-difluorophenyl)-4-methyl-4H-[1,2,4]triazolo[4,3-a][1,4]benzodiazepine

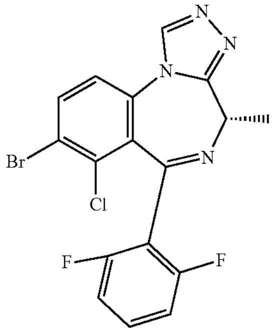 [SMILES: C[C@@H]1N=C(c2c(F)cccc2F)c2c(ccc(Br)c2Cl)-n2cnnc21]

a) (3S)-7-bromo-6-chloro-5-(2,6-difluorophenyl-3-methyl-1,3-dihydro-1,4-benzodiazepine-2-thione In analogy to experiment of example 30 a, (3S)-7-bromo-6-chloro-5-(2,6-difluorophenyl)-3-methyl-1,3-dihydro-1,4-benzodiazepin-2-one (building block L) was converted into the title compound (410 mg, % %) which was obtained as a yellow solid. MS: 415.1 ([{$^{79}$Br, $^{35}$Cl}M+H]$^+$), 417.0 ([{$^{81}$Br, $^{35}$Cl or $^{79}$Br, $^{37}$Cl}M+H]$^+$), ESI pos.

b) (4S)-8-bromo-7-chloro-6-(2,6-difluorophenyl-4-methyl-4H-[1,2,4]triazolo[4,3-a][1,4]benzodiazepine In analogy to experiment of example 30 b, (3S)-7-bromo-6-chloro-5-(2,6-difluorophenyl)-3-methyl-1,3-dihydro-1,4-benzodiazepine-2-thione using formohydrazide was converted after chiral purification into the (−)-enantiopure (S)-title compound (66 mg, 43%) which was obtained as a white solid. MS: 423.0 ([{$^{79}$Br, $^{35}$Cl}M+H]$^+$), 425.1 ([{$^{81}$Br, $^{35}$Cl or $^{79}$Br, $^{37}$Cl}M+H]$^+$), ESI pos.

Example 52

(4S)-7,8-dichloro-6-(2,6-difluorophenyl)-4-methyl-1-pyrimidin-4-yl-4H-[1,2,4]triazolo[4,3-a][1,4]benzodiazepine

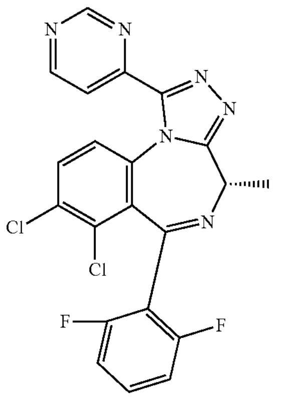 [SMILES: C[C@@H]1N=C(c2c(F)cccc2F)c2c(ccc(Cl)c2Cl)-n2c(-c3ccncn3)nnc21]

a) (3S)-6,7-dichloro-5-(2,6-difluorophenyl)-3-methyl-1,3-dihydro-1,4-benzodiazepine-2-thione In analogy to experiment of example 30 a, (3S)-6,7-dichloro-5-(2,6-difluorophenyl)-3-methyl-1,3-dihydro-1,4-benzodiazepin-2-one (building block M) was converted into the title compound (4.2 g, 90%) which was obtained as a yellow solid. The crude was used as such in the following step without further characterization.

b) (4S)-7,8-dichloro-6-(2,6-difluorophenyl-4-methyl-1-pyrimidin-4-yl-4H-[1,2,4]triazolo[4,3-a][1,4]benzodiazepine In analogy to experiment of example 30 b, (3S)-6,7-dichloro-5-(2,6-difluorophenyl)-3-methyl-1,3-dihydro-1,4-benzodiazepine-2-thione using pyrimidine-4-carbohydrazide was converted after chiral purification into the (−)-enantiopure (S)-title compound (71.6 mg, 31%) which was obtained as a white solid. MS: 456.9 ([{$^{35}$Cl, $^{35}$Cl}M+H]$^+$), ESI pos.

Example 53

(4S)-7,8-dichloro-6-(2,6-difluorophenyl)-4-methyl-1-(1-methylpyrazol-4-yl)-4H-[1,2,4]triazolo[4,3-a][1,4]benzodiazepine

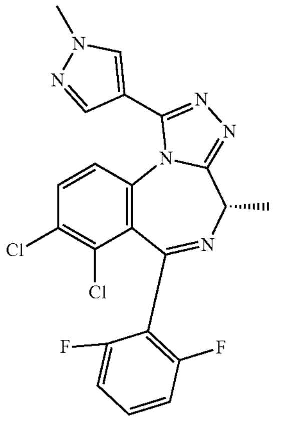 [SMILES: C[C@@H]1N=C(c2c(F)cccc2F)c2c(ccc(Cl)c2Cl)-n2c(-c3cnn(C)c3)nnc21]

In analogy to experiment of example 30 b, (3S)-6,7-dichloro-5-(2,6-difluorophenyl)-3-methyl-1,3-dihydro-1,4-benzodiazepine-2-thione using 1-methylpyrazole-4-carbohydrazide was converted after chiral purification into the (−)-enantiopure (S)-title compound (60.8 mg, 29%) which was obtained as a white solid. MS: 459.1 ([{$^{35}$Cl, $^{35}$Cl}M+H]$^+$), ESI pos.

Example 56

(4S)-7,8-dichloro-6-(2,6-difluorophenyl)-4-methyl-1-pyridazin-3-yl-4H-[1,2,4]triazolo[4,3-a][1,4]benzodiazepine

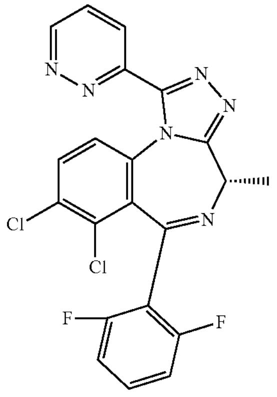 [SMILES: C[C@@H]1N=C(c2c(F)cccc2F)c2c(ccc(Cl)c2Cl)-n2c(-c3cccnn3)nnc21]

In analogy to experiment of example 30 b, (3S)-6,7-dichloro-5-(2,6-difluorophenyl)-3-methyl-1,3-dihydro-1,4-benzodiazepine-2-thione using pyridazine-3-carbohydrazide was converted after chiral purification into the (−)-enantiopure (S)-title compound (80.0 mg, 21%) which was obtained as a white solid. MS: 457.0 ([{$^{35}$Cl, $^{35}$Cl}M+H]$^+$), ESI pos.

Example 63

(4S)-7,8-dichloro-6-(3-fluoro-2-pyridyl)-4-methyl-1-pyridazin-3-yl-4H-[1,2,4]triazolo[4,3-a][1,4]benzodiazepine

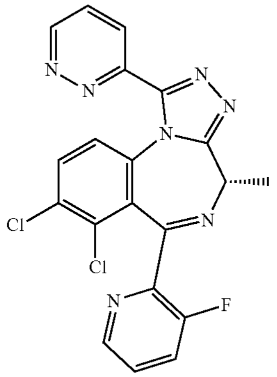 [SMILES: C[C@@H]1N=C(c2ncccc2F)c2c(ccc(Cl)c2Cl)-n2c(-c3cccnn3)nnc21]

a) (3S)-6,7-dichloro-5-(3-fluoro-2-pyridyl-3-methyl-1,3-dihydro-1,4-benzodiazepine-2-thione In analogy to experiment of example 30 a, (3S)-6,7-dichloro-5-(3-fluoro-2-pyridyl)-3-methyl-1,3-dihydro-1,4- benzodiazepin-2-one (building block O) was converted into the title compound (2.56 g, 67%) which was obtained as a light yellow solid. MS: 354.0 ([{$^{35}$Cl, $^{35}$Cl}M+H]$^+$), ESI pos.

b) (4S)-7,8-dichloro-6-(3-fluoro-2-pyridyl)-4-methyl-1-pyridazin-3-yl-4H-[1,2,4]triazolo[4,3-a][1,4]benzodiazepine In analogy to experiment of example 30 b, (3S)-6,7-dichloro-5-(3-fluoro-2-pyridyl)-3-methyl-1,3-dihydro-1,4-benzodiazepine-2-thione was converted after chiral purification into the (+)-enantiopure (S)-title compound (8.8 mg, 2%) which was obtained as a white solid. MS: 440.1 ([{$^{35}$Cl, $^{35}$Cl}M+H]$^+$), ESI pos.

Example 64

(4S)-7,8-dichloro-6-(2,6-difluorophenyl)-4-methyl-2,4-dihydro-[1,2,4]triazolo[4,3-a][1,4]benzodiazepin-1-one

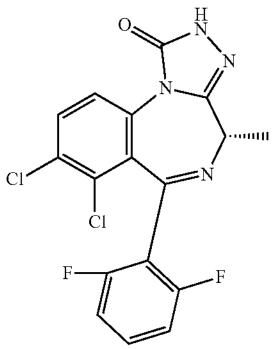 [SMILES: C[C@@H]1N=C(c2c(F)cccc2F)c2c(ccc(Cl)c2Cl)-n2c1n[nH]c2=O]

a) (3S)-6,7-dichloro-5-(2,6-difluorophenyl)-3-methyl-1,3-dihydro-1,4-benzodiazepin-2-one hydrazone To a solution of (3S)-6,7-dichloro-5-(2,6-difluorophenyl)-3-methyl-1,3-dihydro-1,4-benzodiazepine-2-thione (400 mg, 1.08 mmol) in tetrahydrofuran (8.7 mL) was added at room temperature hydrazine monohydrate (109 mg, 104 µl, 2.15 mmol). The mixture was stirred at room temperature for 2 h under argon. The suspension was concentrated in vacuo to give a light yellow solid that was treated with methyl tert-butyl ether (2 mL) and diluted with pentane (4 mL). The mixture was scratched to give a suspension that was stirred for 10 min. The solid was filtered, washed with pentane (2×3 mL) and dried in high vacuo to afford the title compound (300 mg, 75%) which was obtained as a yellow solid. MS: 369.1 ([{$^{35}$Cl, $^{35}$Cl}M+H]$^+$), ESI pos.

b) (4S)-7,8-dichloro-6-(2,6-difluorophenyl-4-methyl-2,4-dihydro-[1,2,4]triazolo[4,3-a][1,4]benzodiazepin-1-one To a solution of (3S)-6,7-dichloro-5-(2,6-difluorophenyl)-3-methyl-1,3-dihydro-1,4-benzodiazepin-2-one hydrazone (250 mg, 0.68 mmol) in tetrahydrofuran (6 mL) was added at room temperature 1,1'-carbonyldiimidazole (132 mg, 0.81 mmol). The reaction mixture was stirred at 70° C. for 5 h, then concentrated in vacuo. The residue was purified by SFC (Chiralcel OJ-3, 0.05% diethylamine in methanol, 5 to 40%) to give the (−)-enantiopure (S)-title compound (141.2 mg, 53%) which was obtained as a white solid. MS: 395.1 ({$^{35}$Cl, $^{35}$Cl}[M+H]$^+$), ESI pos.

Example 66

(4S)-7,8-dichloro-6-(3-fluoro-2-pyridyl)-4-methyl-1-pyrimidin-4-yl-4H-[1,2,4]triazolo[4,3-a][1,4]benzodiazepine

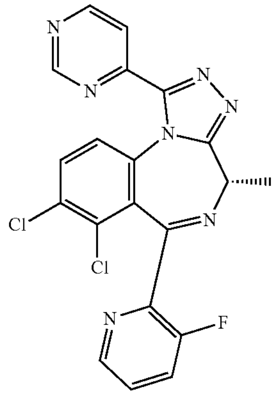 [SMILES: C[C@@H]1N=C(c2ncccc2F)c2c(ccc(Cl)c2Cl)-n2c(-c3ccncn3)nnc21]

In analogy to experiment of example 30 b, (3S)-6,7-dichloro-5-(3-fluoro-2-pyridyl)-3-methyl-1,3-dihydro-1,4-benzodiazepine-2-thione using pyrimidine-4-carbohydrazide was converted after chiral purification into the (+)-enantiopure (S)-title compound (17 mg, 3%) which was obtained as a white solid. MS: 440.1 ([{$^{35}$Cl, $^{35}$Cl}M+H]$^+$), ESI pos.

Example 67

(4S)-7,8-dichloro-6-(3-fluoro-2-pyridyl)-4-methyl-1-(1-methylpyrazol-4-yl)-4H-[1,2,4]triazolo[4,3-a][1,4]benzodiazepine

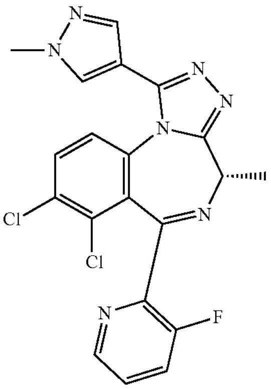

In analogy to experiment of example 30 b, (3S)-6,7-dichloro-5-(3-fluoro-2-pyridyl)-3-methyl-1,3-dihydro-1,4-benzodiazepine-2-thione using 1-methylpyrazole-4-carbohydrazide was converted after chiral purification into the (+)-enantiopure (S)-title compound (86 mg, 46%) which was obtained as a white solid. MS: 442.2 ([{$^{35}$Cl, $^{35}$Cl}M+H]$^+$), ESI pos.

Example 68

(4S)-7,8-dichloro-1-cyclopropyl-6-(3-fluoro-2-pyridyl)-4-methyl-4H-[1,2,4]triazolo[4,3-a][1,4]benzodiazepine

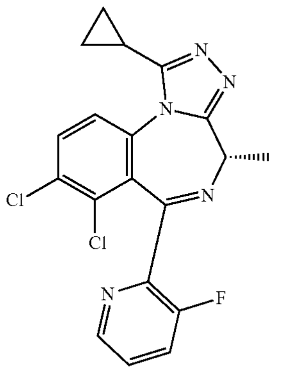 [SMILES: C[C@@H]1N=C(c2ncccc2F)c2c(ccc(Cl)c2Cl)-n2c(C3CC3)nnc21]

In analogy to experiment of example 30 b, (3S)-6,7-dichloro-5-(3-fluoro-2-pyridyl)-3-methyl-1,3-dihydro-1,4-benzodiazepine-2-thione using cyclopropanecarbohydrazide was converted after chiral purification into the (+)-enantiopure (S)-title compound (123 mg, 21%) which was obtained as a white solid. MS: 402.1 ([{$^{35}$Cl, $^{35}$Cl}M+H]$^+$), ESI pos.

Example 73

(4S)-7-bromo-8-chloro-6-(2,6-difluorophenyl)-4-methyl-1-(pyridazin-3-yl)-4H-benzo[f][1,2,4]triazolo[4,3-a][1,4]diazepine

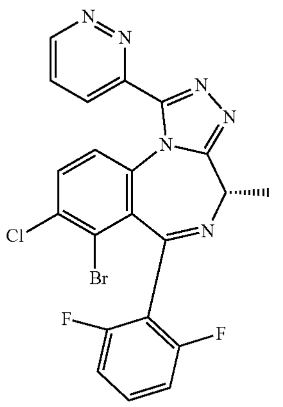 [SMILES: C[C@@H]1N=C(c2c(F)cccc2F)c2c(ccc(Cl)c2Br)-n2c(-c3cccnn3)nnc21]

a) (3S)-6-bromo-7-chloro-5-(2,6-difluorophenyl-3-methyl-1,3-dihydro-1,4-benzodiazepine-2-thione In analogy to experiment of example 30 a, (3S)-6-bromo-7-chloro-5-(2,6-difluorophenyl)-3-methyl-1,3-dihydro-1,4-benzodiazepin-2-one (building block Q) was converted into the title compound (2.72 g, 77%) which was obtained as a yellow powder. MS: 415.1 ([{$^{79}$Br, $^{35}$Cl}M+H]$^+$), 417.0 ([{$^{81}$Br, $^{35}$Cl or $^{79}$Br, $^{37}$Cl}M+H]$^+$), ESI pos.

b) (4S)-7-bromo-8-chloro-6-(2,6-difluorophenyl-4-methyl-1-pyridazin-3-yl-4H-[1,2,4]triazolo[4,3-a][1,4]benzodiazepine In analogy to experiment of example 30 b, (3S)-6-bromo-7-chloro-5-(2,6-difluorophenyl)-3-methyl-1,3-dihydro-1,4-benzodiazepine-2-thione using pyridazine-3-carbohydrazide was converted after chiral purification into the (−)-enantiopure (S)-title compound (24 mg, 20%) which was obtained as a white solid. MS: 501.0 ([{$^{79}$Br, $^{35}$Cl}M+H]$^+$), 503.1 ([{$^{81}$Br, $^{35}$Cl or $^{79}$Br, $^{37}$Cl}M+H]$^+$), ESI pos.

Example 74

(4S)-7-bromo-8-chloro-6-(2,6-difluorophenyl)-4-methyl-1-pyrimidin-4-yl-4H-[1,2,4]triazolo[4,3-a][1,4]benzodiazepine

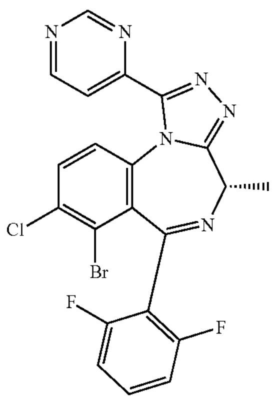 [SMILES: C[C@@H]1N=C(c2c(F)cccc2F)c2c(ccc(Cl)c2Br)-n2c(-c3ccncn3)nnc21]

In analogy to experiment of example 30 b, (3S)-6-bromo-7-chloro-5-(2,6-difluorophenyl)-3-methyl-1,3-dihydro-1,4-benzodiazepine-2-thione using pyrimidine-4-carbohydrazide was converted after chiral purification into the (−)-enantiopure (S)-title compound (13 mg, 11%) which was obtained as a white solid. MS: 501.1 ([{$^{79}$Br, $^{35}$Cl}M+H]$^+$), 503.0 ([{$^{81}$Br, $^{35}$Cl or $^{79}$Br, $^{37}$Cl}M+H]$^+$), ESI pos.

Example 75

(4S)-8-bromo-7-chloro-6-(2,6-difluorophenyl)-1,4-dimethyl-4H-[1,2,4]triazolo[4,3-a][1,4]benzodiazepine

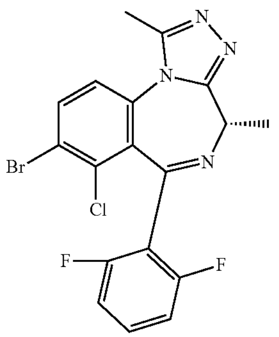 [SMILES: Cc1nnc2n1-c1ccc(Br)c(Cl)c1C(c1c(F)cccc1F)=N[C@H]2C]

In analogy to experiment of example 30 b, (3S)-7-bromo-6-chloro-5-(2,6-difluorophenyl)-3-methyl-1,3-dihydro-1,4-benzodiazepine-2-thione using acetohydrazide was converted after chiral purification into the (−)-enantiopure (S)-title compound (36 mg, 23%) which was obtained as a white solid. MS: 437.0 ([{$^{79}$Br, $^{35}$Cl}M+H]$^+$), 439.1 ([{$^{81}$Br, $^{35}$Cl or $^{79}$Br, $^{37}$Cl}M+H]$^+$), ESI pos.

Example 76

(4S)-7-bromo-8-chloro-6-(2,6-difluorophenyl)-4-methyl-1-(1-methylpyrazol-4-yl)-4H-[1,2,4]triazolo[4,3-a][1,4]benzodiazepine

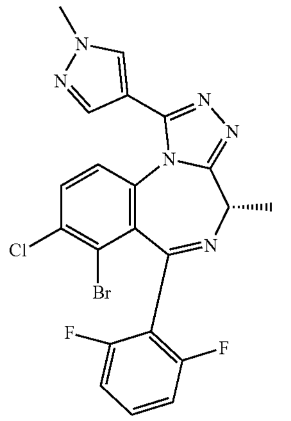 [SMILES: C[C@@H]1N=C(c2c(F)cccc2F)c2c(ccc(Cl)c2Br)-n2c(-c3cnn(C)c3)nnc21]

In analogy to experiment of example 30 b, (3S)-6-bromo-7-chloro-5-(2,6-difluorophenyl)-3-methyl-1,3-dihydro-1,4-benzodiazepine-2-thione using 1-methylpyrazole-4-carbohydrazide was converted after chiral purification into the (−)-enantiopure (S)-title compound (13 mg, 11%) which was obtained a white solid. MS: 503.1 ([{$^{79}$Br, $^{35}$Cl}M+H]$^+$), 505.1 ([{$^{81}$Br, $^{35}$Cl or $^{79}$Br, $^{35}$Cl}M+H]$^+$), ESI pos.

Example 80

(4S)-7-bromo-8-chloro-6-(2,6-difluorophenyl)-1,4-dimethyl-4H-[1,2,4]triazolo[4,3-a][1,4]benzodiazepine

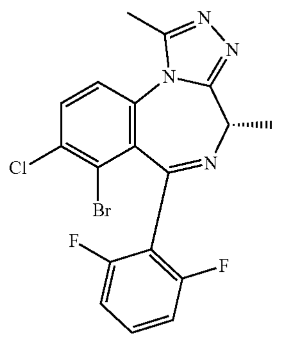 [SMILES: Cc1nnc2n1-c1ccc(Cl)c(Br)c1C(c1c(F)cccc1F)=N[C@H]2C]

In analogy to experiment of example 30 b, (3S)-6-bromo-7-chloro-5-(2,6-difluorophenyl)-3-methyl-1,3-dihydro-1,4-benzodiazepine-2-thione using acetohydrazide was converted after chiral purification into the (−)-enantiopure (S)-title compound (13 mg, 11%) which was obtained as a white solid. MS: 436.9 ([{$^{79}$Br, $^{35}$Cl}M+H]$^+$), 438.9 ([{$^{81}$Br, $^{35}$Cl or $^{79}$Br, $^{35}$Cl}M+H]$^+$), ESI pos.

Example 81

(4S)-7-bromo-8-chloro-6-(2,6-difluorophenyl)-4-methyl-1-(1-methylpyrazol-3-yl)-4H-[1,2,4]triazolo[4,3-a][1,4]benzodiazepine

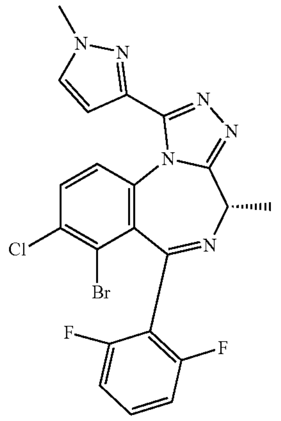 [SMILES: C[C@@H]1N=C(c2c(F)cccc2F)c2c(ccc(Cl)c2Br)-n2c(-c3ccn(C)n3)nnc21]

In analogy to experiment of example 30 b, (3S)-6-bromo-7-chloro-5-(2,6-difluorophenyl)-3-methyl-1,3-dihydro-1,4-benzodiazepine-2-thione using 1-methylpyrazole-3-carbohydrazide was converted after chiral purification into the (−)-enantiopure (S)-title title compound (38 mg, 26%) which was obtained as a white solid. MS: 503.0 ([{$^{79}$Br, $^{35}$Cl}M+H]$^+$), 505.1 ([{$^{81}$Br, $^{35}$Cl or $^{79}$Br, $^{37}$Cl}M+H]$^+$), ESI pos.

Example 82

(4S)-7,8-dichloro-6-(2,6-difluorophenyl)-1,4-dimethyl-4H-[1,2,4]triazolo[4,3-a][1,4]benzodiazepine

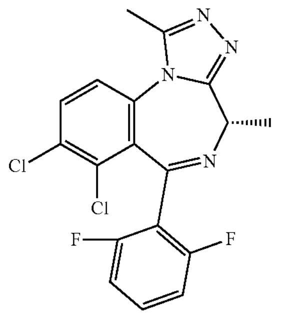 [SMILES: Cc1nnc2n1-c1ccc(Cl)c(Cl)c1C(c1c(F)cccc1F)=N[C@H]2C]

In analogy to experiment of example 30 b, (3S)-6,7-dichloro-5-(2,6-difluorophenyl)-3-methyl-1,3-dihydro-1,4-benzodiazepine-2-thione using acetohydrazide was converted after chiral purification into the (−)-enantiopure (S)-title compound (62.3 mg, 19%) which was obtained as a white solid. MS: 393.0 ([{$^{35}$Cl, $^{35}$Cl}M+H]$^+$), ESI pos.

Example 83

(4S)-8-bromo-7-chloro-1-cyclopropyl-6-(3-fluoro-2-pyridyl)-4-methyl-4H-[1,2,4]triazolo[4,3-a][1,4]benzodiazepine

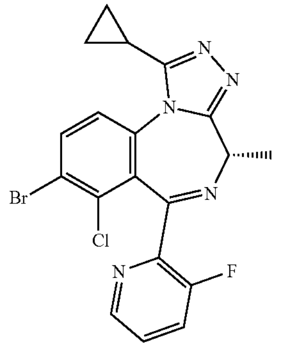 [SMILES: C[C@@H]1N=C(c2ncccc2F)c2c(ccc(Br)c2Cl)-n2c(C3CC3)nnc21]

a) (3S)-7-bromo-6-chloro-5-(3-fluoro-2-pyridyl)-3-methyl-1,3-dihydro-1,4-benzodiazepine-2-thione In analogy to experiment of example 30 a, (3S)-7-bromo-6-chloro-5-(3-fluoro-2-pyridyl)-3-methyl-1,3-dihydro-1,4-benzodiazepin-2-one (building block R) was converted into the title compound (720 mg, 46%) which was obtained as a yellow solid. MS: 398.0 ([{$^{79}$Br, $^{35}$Cl}M+H]$^+$), 400.1 ([{$^{81}$Br, $^{35}$Cl or $^{79}$Br, $^{37}$Cl}M+H]$^+$), ESI pos.

b) (4S)-8-bromo-7-chloro-1-cyclopropyl-6-(3-fluoro-2-pyridyl-4-methyl-4H-[1,2,4]triazolo[4,3-a][1,4]benzodiazepine In analogy to experiment of example 30 b, (3S)-7-bromo-6-chloro-5-(3-fluoro-2-pyridyl)-3-methyl-1,3-dihydro-1,4-benzodiazepine-2-thione using cyclopropanecarbohydrazide was converted after chiral purification into the (+)-enantiopure (S)-title compound (38 mg, 11%) which was obtained as a light yellow solid. MS: 446.1 ([{$^{79}$Br, $^{35}$Cl}M+H]$^+$), 448.0 ([{$^{81}$Br, $^{35}$Cl or $^{79}$Br, $^{37}$Cl}M+H]$^+$), ESI pos.

Example 84

(4S)-8-bromo-7-chloro-6-(3-fluoro-2-pyridyl)-4-methyl-4H-[1,2,4]triazolo[4,3-a][1,4]benzodiazepine

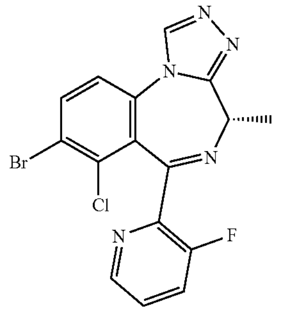 [SMILES: C[C@@H]1N=C(c2ncccc2F)c2c(ccc(Br)c2Cl)-n2cnnc21]

In analogy to experiment of example 30 b, (3S)-7-bromo-6-chloro-5-(3-fluoro-2-pyridyl)-3-methyl-1,3-dihydro-1,4-benzodiazepine-2-thione using formohydrazide was converted after chiral purification into the (+)-enantiopure (S)-title compound (38 mg, 12%) which was obtained as a light yellow solid MS: 406.0 ([{$^{79}$Br, $^{35}$Cl}M+H]$^+$), 408.1 ([{$^{81}$Br, $^{35}$Cl or $^{79}$Br, $^{37}$Cl}M+H]$^+$), ESI pos.

Example 85

(4S)-8-bromo-7-chloro-6-(3-fluoro-2-pyridyl)-1,4-dimethyl-4H-[1,2,4]triazolo[4,3-a][1,4]benzodiazepine

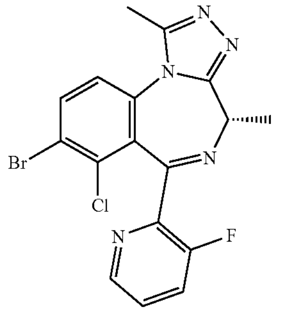 [SMILES: Cc1nnc2n1-c1ccc(Br)c(Cl)c1C(c1ncccc1F)=N[C@H]2C]

In analogy to experiment of example 30 b, (3S)-7-bromo-6-chloro-5-(3-fluoro-2-pyridyl)-3-methyl-1,3-dihydro-1,4-benzodiazepine-2-thione using acetohydrazide was converted after chiral purification into the (+)-enantiopure (S)-title compound (31 mg, 8%) which was obtained as a white solid MS: 420.0 ([{$^{79}$Br, $^{35}$Cl}M+H]$^+$), 422.0 ([{$^{81}$Br, $^{35}$Cl or $^{79}$Br, $^{37}$Cl}M+H]$^+$), ESI pos.

Example 86

(4S)-7,8-dichloro-6-(2,6-difluorophenyl)-4-methyl-1-(6-methylpyridazin-3-yl)-4H-[1,2,4]triazolo[4,3-a][1,4]benzodiazepine

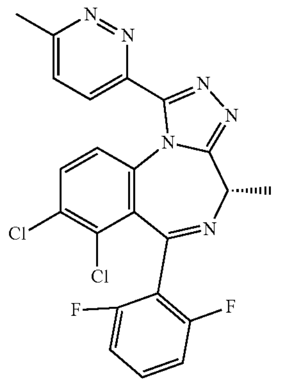

a) 6-methylpyridazine-3-carbohydrazide

A solution of ethyl 6-methylpyridazine-3-carboxylate (3.71 g, 22.3 mmol) in methanol (40 mL) was heated to 60° C. After 10 min, hydrazine-monohydrate (1.62 mL, 33.5 mmol) was carefully added and the reaction mixture was allowed to cool down to room temperature. Following up the addition of diethyl ether (60 mL), the reaction mixture was cooled down to 0° C. After 2 hours, the resulting suspension was filtered through a sintered funnel. The collected solid was washed with diethyl ether and dried under high vacuum to afford the title compound (1.4 g, 41%) which was obtained as an off-white powder. MS: 153.1 ($[M+H]^+$), ESI pos.

b) (4S)-7,8-dichloro-6-(2,6-difluorophenyl-4-methyl-1-(6-methylpyridazin-3-yl)-4H-[1,2,4]triazolo[4,3-a][1,4]benzodiazepine In analogy to experiment of example 30 b, (3S)-6,7-dichloro-5-(2,6-difluorophenyl)-3-methyl-1,3-dihydro-1,4-benzodiazepine-2-thione using 6-methylpyridazine-3-carbohydrazide was converted after chiral purification into the (−)-enantiopure (S)-title compound (52.6 mg, 44%) which was obtained as a white solid. MS: 471.1 ($[\{^{35}Cl, ^{35}Cl\}M+H]^+$), ESI pos.

Example 87

5-[(4S)-7,8-dichloro-6-(2,6-difluorophenyl)-4-methyl-4H-[1,2,4]triazolo[4,3-a][1,4]benzodiazepin-1-yl]-3-methyl-isoxazole

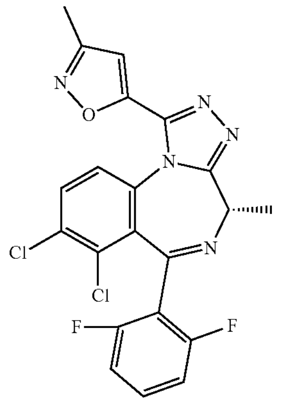 [SMILES: Cc1cc(-c2nnc3n2-c2ccc(Cl)c(Cl)c2C(c2c(F)cccc2F)=N[C@H]3C)on1]

a) 3-methyl-1,2-didehydroisoxazole-5-carbohydrazide

In analogy to experiment of example 86 a, methyl 3-methyl-1,2-didehydroisoxazole-5-carboxylate was converted into the title compound (800 mg, 74%) which was obtained as a white solid. MS: 142.1 ($[M+H]^+$), ESI pos.

b) 5-[(4S)-7,8-dichloro-6-(2,6-difluorophenyl-4-methyl-4H-[1,2,4]triazolo[4,3-a][1,4]benzodiazepin-1-yl]-3-methyl-isoxazole In analogy to experiment of example 30 b, (3S)-6,7-dichloro-5-(2,6-difluorophenyl)-3-methyl-1,3-dihydro-1,4-benzodiazepine-2-thione using 3-methyl-1,2-didehydroisoxazole-5-carbohydrazide was converted after chiral purification into the (−)-enantiopure (S)-title compound (54.1 mg, 31%) which was obtained as a white solid. MS: 460.1 ($[\{^{35}Cl, ^{35}Cl\}M+H]^+$), ESI pos.

Example 88

(4S)-7-bromo-8-chloro-6-(2,6-difluorophenyl)-4-methyl-1-(6-methylpyridazin-3-yl)-4H-[1,2,4]triazolo[4,3-a][1,4]benzodiazepine

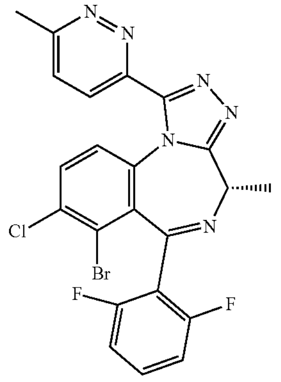

In analogy to experiment of example 30 b, (3S)-6-bromo-7-chloro-5-(2,6-difluorophenyl)-3-methyl-1,3-dihydro-1,4-benzodiazepine-2-thione using 6-methylpyridazine-3-carbohydrazide was converted after chiral purification into the (−)-enantiopure (S)-title compound (30 mg, 24%) which was obtained as a white solid MS: 515.0 ($[\{^{79}Br, ^{35}Cl\}M+H]^+$), 517.0 ($[\{^{81}Br, ^{35}Cl$ or $^{79}Br, ^{37}Cl\}M+H]^+$), ESI pos.

Example 89

(4S)-7-bromo-8-chloro-6-(2,6-difluorophenyl)-4-methyl-2,4-dihydro-[1,2,4]triazolo[4,3-a][1,4]benzodiazepin-1-one

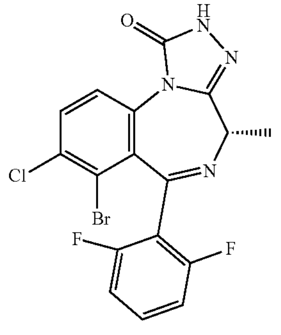 [SMILES: C[C@@H]1N=C(c2c(F)cccc2F)c2c(ccc(Cl)c2Br)-n2c1n[nH]c2=O]

a) (3S)-6-bromo-7-chloro-5-(2,6-difluorophenyl-3-methyl-1,3-dihydro-1,4-benzodiazepin-2-one hydrazone In analogy to experiment of example 64 a, (3S)-6-bromo-7-chloro-5-(2,6-difluorophenyl)-3-methyl-1,3-dihydro-1,4-benzodiazepine-2-thione was converted into the title compound (40 mg, 20%) which was obtained as a powder. MS: 413.0 ($[\{^{79}Br, ^{35}Cl\}M+H]^+$), 415.0 ($[\{^{81}Br, ^{35}Cl$ or $^{79}Br, ^{37}Cl\}M+H]^+$), ESI pos.

b) (4S)-7-bromo-8-chloro-6-(2,6-difluorophenyl-4-methyl-2,4-dihydro-[1,2,4]triazolo[4,3-a][1,4]benzodiazepin-1-one In analogy to experiment of example 64 b, (3S)-6-bromo-7-chloro-5-(2,6-difluorophenyl)-3-methyl-1,3-dihydro-1,4-benzodiazepin-2-one hydrazone was converted after chiral purification into the (−)-enantiopure (S)-title compound (12 mg, 28%) which was obtained as a white solid. MS: 439.0 ([{$^{79}$Br, $^{35}$Cl}M+H]$^+$), 441.1 ([{$^{81}$Br, $^{35}$Cl or $^{79}$Br, $^{37}$Cl}M+H]$^+$), ESI pos.

Example 92

(4S)-7-chloro-6-(2,6-difluorophenyl)-1,4-dimethyl-8-(trifluoromethyl)-4H-[1,2,4]triazolo[4,3-a][1,4]benzodiazepine

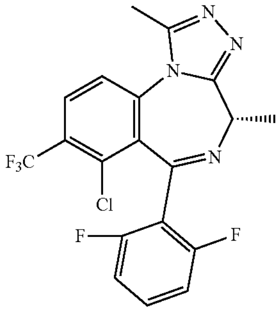 [SMILES: Cc1nnc2n1-c1ccc(C(F)(F)F)c(Cl)c1C(c1c(F)cccc1F)=N[C@H]2C]

a) (3S)-6-chloro-5-(2,6-difluorophenyl-3-methyl-7-(trifluoromethyl-1,3-dihydro-1,4-benzodiazepin-2-one A solution of (3S)-6-chloro-5-(2,6-difluorophenyl)-3-methyl-7-iodo-1,3-dihydro-1,4-benzodiazepin-2-one (building block S, 500 mg, 1.12 mmol), iodocopper (426 mg, 2.24 mmol), hexamethylphosphoramide (2.5 mL, 1.12 mmol) and methyl 2,2-difluoro-2-fluorosulfonyl-acetate (645 mg, 3.36 mmol) in N,N-dimethylformamide (5 mL) was stirred at 70° C. for 16 h. Methyl 2,2-difluoro-2-fluorosulfonyl-acetate (430 mg, 2.24 mmol) and iodocopper (213 mg, 1.12 mmol) were added and the reaction mixture stirred at 70° C. for additional 4 h. The mixture was diluted with ethyl acetate (150 mL), washed with saturated aqueous ammonium chloride (80 mL) and the organic layer was filtered through a sintered funnel. The filtrate was washed with water (50 mL) and brine (50 mL), dried over sodium sulfate and concentrated in vacuo. The crude was purified by flash column chromatography (silica, petroleum ether/ethyl acetate, 20:1 to 1:1) to afford the title compound (550 mg, 127%) which was obtained as a dark red oil. MS: 389.0 ([M+H]$^+$), ESI pos.

b) (3S)-6-chloro-5-(2,6-difluorophenyl-3-methyl-7-(trifluoromethyl)-1,3-dihydro-1,4-benzodiazepine-2-thione In analogy to experiment of example 30 a, (3S)-6-chloro-5-(2,6-difluorophenyl)-3-methyl-7-(trifluoromethyl)-1,3-dihydro-1,4-benzodiazepin-2-one was converted into the title compound (400 mg, 77%) which was obtained as a yellow solid. MS: 405.0 ([M+H]$^+$), ESI pos.

c) (4S)-7-chloro-6-(2,6-difluorophenyl)-1,4-dimethyl-8-(trifluoromethyl)-4H-[1,2,4]triazolo[4,3-a][1,4]benzodiazepine In analogy to experiment of example 30 b, (3S)-6-chloro-5-(2,6-difluorophenyl)-3-methyl-7-(trifluoromethyl)-1,3-dihydro-1,4-benzodiazepine-2-thione using acetohydrazide was converted after chiral purification into the (−)-enantiopure (S)-title compound (63.5 mg, 32%) which was obtained as a white solid. MS: 427.1 ([M+H]$^+$), ESI pos.

Example 93

(4S)-7-chloro-8-(1,1-difluoroethyl)-6-(2,6-difluorophenyl)-1,4-dimethyl-4H-[1,2,4]triazolo[4,3-a][1,4]benzodiazepine

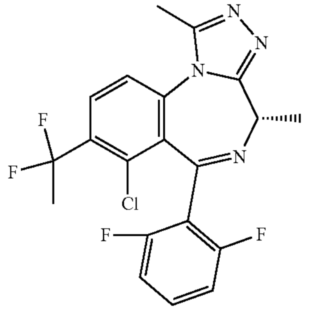 [SMILES: Cc1nnc2n1-c1ccc(C(C)(F)F)c(Cl)c1C(c1c(F)cccc1F)=N[C@H]2C]

a) (4S)-7-chloro-6-(2,6-difluorophenyl-8(1-ethoxyvinyl)-1,4-dimethyl-4H-[1,2,4]triazolo[4,3-a][1,4]benzodiazepine To a suspension of (4S)-8-bromo-7-chloro-6-(2,6-difluorophenyl)-1,4-dimethyl-4H-[1,2,4]triazolo[4,3-a][1,4]benzodiazepine (example 75, 210.0 mg, 0.480 mmol) and tributyl(1-ethoxyvinyl)tin (346.57 mg, 0.960 mmol) in N,N-dimethylformamide (2.1 mL) was added tetrakis(triphenylphosphine)palladium(0) (56.42 mg, 0.050 mmol). The reaction mixture was stirred at 80° C. for 1 h. The mixture was diluted with dichloromethane (2×20 mL), washed with water (20 mL) and brine (20 mL), dried over sodium sulfate and concentrated in vacuo. The residue was purified by flash column chromatography (silica, petroleum ether/ethyl acetate 10:1, dichloromethane/methanol 80:1) to afford the title compound (300 mg, 98%) which was obtained as a colorless oil. MS: 429.1 ([M+H]$^+$), ESI pos.

b) 1-[(4S)-7-chloro-6-(2,6-difluorophenyl)-1,4-dimethyl-4H-[1,2,4]triazolo[4,3-a][1,4]benzodiazepin-8-yl]ethanone To a solution of (4S)-7-chloro-6-(2,6-difluorophenyl)-8-(1-ethoxyvinyl)-1,4-dimethyl-4H-[1,2,4]triazolo[4,3-a][1,4]benzodiazepine (280 mg, 0.650 mmol) in 1,4-dioxane (7 mL) was added aqueous hydrochloric acid (2.0 M, 1.62 mL, 3.23 mmol). The mixture was stirred at room temperature for 0.5 h, before being diluted with dichloromethane (100 mL). The organic layer was washed with water (3×10 mL), aqueous sodium bicarbonate (3×50 mL) and brine (50 mL), then dried over sodium sulfate and concentrated in vacuo. The residue was purified by preparative HPLC (Boston Prime C18, 0.1% trifluoroacetic acid in water/acetonitrile) and lyophilized to afford the title compound (220 mg, 84%) which was obtained as a light yellow solid. MS: 401.1 ([M+H]$^+$), ESI pos.

c) (4S)-7-chloro-8-(1,1-difluoroethyl)-6-(2,6-difluorophenyl)-1,4-dimethyl-4H-[1,2,4]triazolo[4,3-a][1,4]benzodiazepine To a solution 1-[(4S)-7-chloro-6-(2,6-difluorophenyl)-1,4-dimethyl-4H-[1,2,4]triazolo[4,3-a][1,4]benzodiazepin-8-yl]ethanone (100 mg, 0.250 mmol) in dichloroethane (2 mL) was added diethylaminosulfur trifluoride (120.6 mg, 0.750 mmol) at 0° C. The mixture was stirred at room temperature for 24 h, before being poured into saturated aqueous sodium bicarbonate (20 mL). The mixture was extracted with dichloromethane (2×50 mL). The combined organic extracts were washed with brine (30 mL), dried over sodium sulfate and concentrated in vacuo. The residue was purified by preparative HPLC (Phenomenex Synergi C18, 0.1% trifluoroacetic acid in water/acetonitrile) to afford the (−)-enantiopure (S)-title compound (20.1 mg, 18%) which was obtained as a white solid. MS: 423.0 ([M+H]$^+$), ESI pos.

Example 94

(4S)-7,8-dichloro-6-(2,6-difluorophenyl)-4-methyl-1-(6-methylpyrimidin-4-yl)-4H-[1,2,4]triazolo[4,3-a][1,4]benzodiazepine

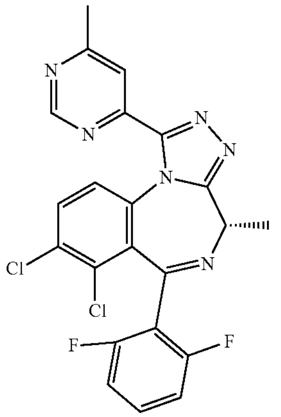 [SMILES: Cc1cc(-c2nnc3n2-c2ccc(Cl)c(Cl)c2C(c2c(F)cccc2F)=N[C@H]3C)ncn1]

In analogy to experiment of example 30 b, (3S)-6,7-dichloro-5-(2,6-difluorophenyl)-3-methyl-1,3-dihydro-1,4-benzodiazepine-2-thione using 6-methylpyrimidine-4-carbohydrazide was converted after chiral purification into the (−)-enantiopure (S)-title compound (70.0 mg, 35%) which was obtained as a white solid. MS: 471.2 ([{$^{35}$Cl, $^{35}$Cl}M+H]$^+$), ESI pos.

Example 95

(4S)-7,8-dichloro-6-(2,6-difluorophenyl)-4-methyl-1-(2-methylpyrimidin-4-yl)-4H-[1,2,4]triazolo[4,3-a][1,4]benzodiazepine

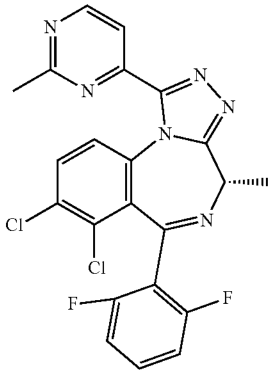

In analogy to experiment of example 30 b, (3S)-6,7-dichloro-5-(2,6-difluorophenyl)-3-methyl-1,3-dihydro-1,4-benzodiazepine-2-thione using 2-methylpyrimidine-4-carbohydrazide was converted after chiral purification into the (−)-enantiopure (S)-title compound (12.0 mg, 20%) which was obtained as a white solid. MS: 471.2 ([{$^{35}$Cl, $^{35}$Cl}M+H]$^+$), ESI pos.

Example 96 (4S)-7,8-dichloro-6-(2,6-difluorophenyl)-1-(2,6-dimethylpyrimidin-4-yl)-4-methyl-4H-[1,2,4]triazolo[4,3-a][1,4]benzodiazepine

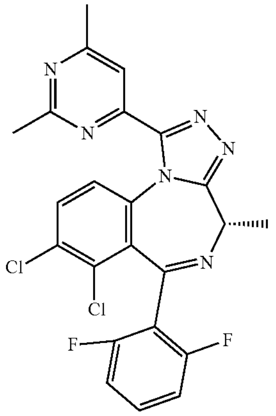

In analogy to experiment of example 30 b, (3S)-6,7-dichloro-5-(2,6-difluorophenyl)-3-methyl-1,3-dihydro-1,4-benzodiazepine-2-thione using 2,6-dimethylpyrimidine-4-carbohydrazide was converted after chiral purification into the (−)-enantiopure (S)-title compound (66.8 mg, 44%) which was obtained as a white solid. MS: 485.1 ([{$^{35}$Cl, $^{35}$Cl}M+H]$^+$), ESI pos.

Example 97

(4S)-7-chloro-6-(2,6-difluorophenyl)-1,4,8-trimethyl-4H-[1,2,4]triazolo[4,3-a][1,4]benzodiazepine

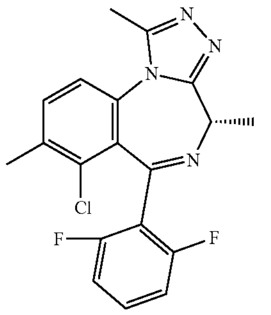

A mixture of (4S)-8-bromo-7-chloro-6-(2,6-difluorophenyl)-1,4-dimethyl-4H-[1,2,4]triazolo[4,3-a][1,4]benzodiazepine (300 mg, 0.690 mmol), tetrakis (triphenylphosphine) palladium (0) (79.2 mg, 0.070 mmol), trimethylaluminum (2.0 M in toluene, 0.51 mL, 1.03 mmol) in N,N-dimethylformamide (6 mL) was heated to 70° C. After 16 h, the mixture was diluted with dichloromethane (30 mL). The organic layer was washed with water (20 mL), brine (30 mL), dried over sodium sulfate and concentrated in vacuo. The residue was purified by preparative HPLC (Boston Prime, 0.1% trifluoroacetic acid in water/acetonitrile) and lyophilized to afford the (−)-enantiopure (S)-title compound (27.3 mg, 58%) which was obtained as a white solid. MS: 373.2 ([M+H]$^+$), ESI pos.

Example 98

(4S)-8-bromo-7-chloro-6-(2,6-difluorophenyl)-4-ethyl-1-methyl-4H-[1,2,4]triazolo[4,3-a][1,4]benzodiazepine

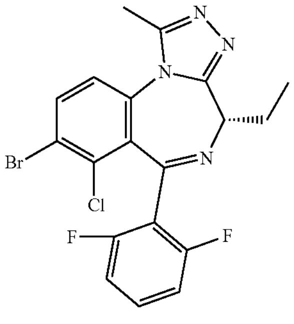 [SMILES: CC[C@@H]1N=C(c2c(F)cccc2F)c2c(ccc(Br)c2Cl)-n2c(C)nnc21]

a) (3S)-7-bromo-6-chloro-5-(2,6-difluorophenyl)-3-ethyl-1,3-dihydro-1,4-benzodiazepine-2-thione In analogy to experiment of example 30 a, (3S)-7-bromo-6-chloro-5-(2,6-difluorophenyl)-3-ethyl-1,3-dihydro-1,4-benzodiazepin-2-one (building block T) was converted into the title compound (600 mg, 92%) which was obtained as a yellow solid. MS: 429.0 ([{$^{79}$Br, $^{35}$Cl}M+H]$^+$), 431.1 ([{$^{81}$Br, $^{35}$Cl or $^{79}$Br, $^{37}$Cl}M+H]$^+$), ESI pos.

b) (3S)-7-bromo-6-chloro-5-(2,6-difluorophenyl-3-ethyl-1,3-dihydro-1,4-benzodiazepin-2-one hydrazone A solution of (3S)-7-bromo-6-chloro-5-(2,6-difluorophenyl)-3-ethyl-1,3-dihydro-1,4-benzodiazepine-2-thione (500 mg, 1.16 mmol) and hydrazine hydrate (117 mg, 2.33 mmol) in tetrahydrofuran (5 mL) was cooled to 15° C. and stirred for 1 h. The mixture was concentrated in vacuo to afford the title compound (450 mg, 90%) as a light green foam. MS: 427.2 ([{$^{79}$Br, $^{35}$Cl}M+H]$^+$), 429.3 ([{$^{81}$Br, $^{35}$Cl or $^{79}$Br, $^{37}$Cl}M+H]$^+$), ESI pos.

c) (4S)-8-bromo-7-chloro-6-(2,6-difluorophenyl)-4-ethyl-1-methyl-4H-[1,2,4]triazolo[4,3-a][1,4]benzodiazepine A solution of (3S)-7-bromo-6-chloro-5-(2,6-difluorophenyl)-3-ethyl-1,3-dihydro-1,4-benzodiazepin-2-one hydrazone (450 mg, 1.05 mmol) and triethyl orthoacetate (854 mg, 5.26 mmol) in toluene (5 mL) was heated to 120° C. After 1 h, the reaction mixture was concentrated in vacuo. The residue was purified directly by flash column chromatography (dichloromethane/methanol 20:1) followed by chiral purification to afford the (−)-enantiopure (S)-title compound (400 mg, 82%) as a light yellow foam. MS: 451.0 ([{$^{79}$Br, $^{35}$Cl}M+H]$^+$), 453.0 ([{$^{81}$Br, $^{35}$Cl or $^{79}$Br, $^{37}$Cl}M+H]$^+$), ESI pos.

Example 99

(4S)-7-chloro-8-(difluoromethyl)-6-(2,6-difluorophenyl)-1,4-dimethyl-4H-[1,2,4]triazolo[4,3-a][1,4]benzodiazepine

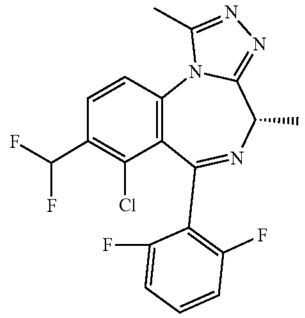 [SMILES: Cc1nnc2n1-c1ccc(C(F)F)c(Cl)c1C(c1c(F)cccc1F)=N[C@H]2C]

a) (4S)-7-chloro-6-(2,6-difluorophenyl)-1,4-dimethyl-8-vinyl-4H-[1,2,4]triazolo[4,3-a][1,4]benzodiazepine To a solution of (4S)-8-bromo-7-chloro-6-(2,6-difluorophenyl)-1,4-dimethyl-4H-[1,2,4]triazolo[4,3-a][1,4]benzodiazepine (3.0 g, 6.85 mmol) in ethanol (70 mL) was added potassium vinyltrifluoroborate (1.85 g, 1.37 mmol), triethylamine (2.08 g, 20.56 mmol), [1,1'-bis (diphenylphosphino)ferrocene]dichloropalladium(II) (0.5 g, 0.690 mmol). The reaction mixture was heated to 80° C. After 16 h, water (100 mL) was added and the reaction mixture was extracted with ethyl acetate (2×100 mL). The combined organic extracts were washed with brine (100 mL), dried over sodium sulfate, filtered and concentrated in vacuo. The residue was purified by flash column chromatography (petroleum ether/ethyl acetate/ethanol 20:3:1 to 8:3:1) to afford the title compound (2.8 g, 88%) which was obtained as a brown solid. MS: 385.1 ([M+H]$^+$), ESI pos.

b) (4S)-7-chloro-6-(2,6-difluorophenyl-1,4-dimethyl-4H-[1,2,4]triazolo[4,3-a][1,4]benzodiazepine-8-carbaldehyde To a solution of (4S)-7-chloro-6-(2,6-difluorophenyl)-1,4-dimethyl-8-vinyl-4H-[1,2,4]triazolo[4,3-a][1,4]benzodiazepine (2.8 g, 7.28 mmol) in acetone (56 mL) and water (14 mL) was added osmium tetroxide (184.99 mg, 0.730 mmol). After 10 min stirring at room temperature, sodium periodate (3.1 g, 14.5 mmol) was added and the mixture was stirred for further 1 h at room temperature. The reaction mixture was diluted with water (10 mL) and ethyl acetate (100 mL). The organic layer was washed with brine (2×50 mL), dried over sodium sulfate, filtered and concentrated in vacuo. The residue was purified by flash column chromatography (silica, dichloromethane/methanol 200:1 to 60:1) to afford the title compound (1.8 g, 47%) which was obtained as a yellow solid. MS: 387.1 ([M+H]$^+$), ESI pos.

c) (4S)-7-chloro-8-(difluoromethyl)-6-(2,6-difluorophenyl)-1,4-dimethyl-4H-[1,2,4]triazolo[4,3-a][1,4]benzodiazepine To a solution of (4S)-7-chloro-6-(2,6-difluorophenyl)-1,4-dimethyl-4H-[1,2,4]triazolo[4,3-a][1,4]benzodiazepine-8-carbaldehyde (1.8 g, 4.65 mmol) in dichloroethane (37.0 mL) was added diethylaminosulfur trifluoride (2.25 g, 14.0 mmol) at 0° C. Upon addition, the reaction mixture was warmed up to room temperature and stirred for further 2 h. The reaction mixture was quenched by addition of saturated aqueous sodium bicarbonate (10 mL), then extracted with dichloromethane (2×30 mL). The combined organic extracts were washed with brine (2×50 mL), filtered and concentrated in vacuo. The residue was purified by preparative HPLC (Boston Prime C18, 0.1% trifluoroacetic acid in water/acetonitrile) and lyophilized to afford the (−)-enantiopure (S)-title compound (359 mg, 50%) which was obtained as a white solid. MS: 409.1 ([M+H]$^+$), ESI pos.

Example 100

(4R)-8-bromo-7-chloro-6-(2,6-difluorophenyl)-4-(methoxymethyl)-1-methyl-4H-[1,2,4]triazolo[4,3-a][1,4]benzodiazepine

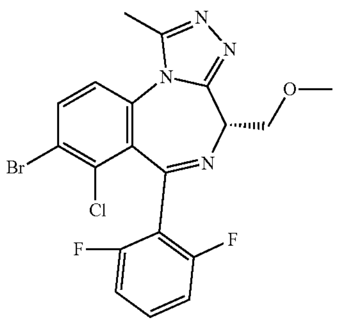 [SMILES: COC[C@@H]1N=C(c2c(F)cccc2F)c2c(ccc(Br)c2Cl)-n2c(C)nnc21]

a) (3S)-7-bromo-6-chloro-5-(2,6-difluorophenyl)-3-(methoxymethyl-1,3-dihydro-1,4-benzodiazepine-2-thione In analogy to experiment of example 30 a, (3S)-7-bromo-6-chloro-5-(2,6-difluorophenyl)-3-(methoxymethyl)-1,3-dihydro-1,4-benzodiazepin-2-one (building block U) was converted into the title compound (1.2 g, 76%) which was obtained as a yellow solid. MS: 445.0 ([{$^{79}$Br, $^{35}$Cl}M+H]$^+$), 447.1 ([{$^1$Br, $^{35}$Cl or $^{79}$Br, $^{37}$Cl}M+H]$^+$), ESI pos.

b) (3R)-7-bromo-6-chloro-5-(2,6-difluorophenyl)-3-(methoxymethyl-1,3-dihydro-1,4-benzodiazepin-2-one hydrazone In analogy to experiment of example 98 b, (3S)-7-bromo-6-chloro-5-(2,6-difluorophenyl)-3-(methoxymethyl)-1,3-dihydro-1,4-benzodiazepine-2-thione was converted into the title compound (1.1 g, 96%) which was obtained as a yellow solid. MS: 443.1 ([{$^{79}$Br, $^{35}$Cl}M+H]$^+$), 445.1 ([{$^{81}$Br, $^{35}$Cl or $^{79}$Br, $^{37}$Cl}M+H]$^+$), ESI pos.

c) (4R)-8-bromo-7-chloro-6-(2,6-difluorophenyl)-4-(methoxymethyl-1-methyl-4H-[1,2,4]triazolo[4,3-a][1,4]benzodiazepine In analogy to experiment of example 98 c, (3R)-7-bromo-6-chloro-5-(2,6-difluorophenyl)-3-(methoxymethyl)-1,3-dihydro-1,4-benzodiazepin-2-one hydrazone was converted after chiral purification into the (−)-enantiopure (R)-title compound (68 mg, 6%) which was obtained as a white solid. MS: 467.2 ([{$^{79}$Br, $^{35}$Cl}M+H]$^+$), 469.1 ([{$^{81}$Br, $^{35}$Cl or $^{79}$Br, $^{37}$Cl}M+H]$^+$), ESI pos.

Example 101

[(4R)-8-bromo-7-chloro-6-(2,6-difluorophenyl)-1-methyl-4H-[1,2,4]triazolo[4,3-a][1,4]benzodiazepin-4-yl]methanol

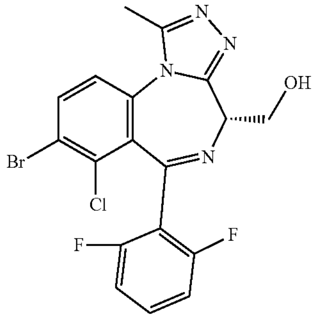 [SMILES: Cc1nnc2n1-c1ccc(Br)c(Cl)c1C(c1c(F)cccc1F)=N[C@H]2CO]

To a stirred suspension of (4R)-8-bromo-7-chloro-6-(2,6-difluorophenyl)-4-(methoxymethyl)-1-methyl-4H-[1,2,4]triazolo[4,3-a][1,4]benzodiazepine (230.0 mg, 0.490 mmol) and sodium iodide (147.43 mg, 0.980 mmol) in dichloromethane (3 mL) was added at −30° C. a solution of boron tribromide (308.0 mg, 1.23 mmol) in dichloromethane (0.5 mL). The reaction mixture was warmed up to room temperature and stirred for further 1 h, before being concentrated in vacuo. The residue was purified by preparative HPLC (Phenomenex luna, 0.1% trifluoroacetic acid in water/acetonitrile) then SFC (Daicel Chiralpak AD-H, 0.1% ammonia in methanol) to afford the (−)-enantiopure (R)-title compound (71 mg, 47%) as a white solid. MS: 453.2 ([{$^{79}$Br, $^{35}$Cl}M+H]$^+$), 455.2 ([{$^{81}$Br, $^{35}$Cl or $^{79}$Br, $^{37}$Cl}M+H]$^+$), ESI pos.

Example 102

(4S)-7-chloro-6-(2,6-difluorophenyl)-8-iodo-1,4-dimethyl-4H-[1,2,4]triazolo[4,3-a][1,4]benzodiazepine

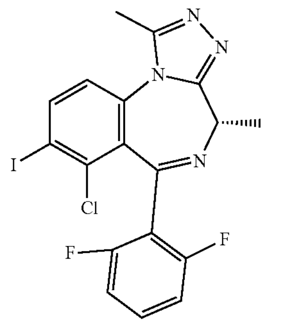 [SMILES: Cc1nnc2n1-c1ccc(I)c(Cl)c1C(c1c(F)cccc1F)=N[C@H]2C]

To a mixture of (4S)-8-bromo-7-chloro-6-(2,6-difluorophenyl)-1,4-dimethyl-4H-[1,2,4]triazolo[4,3-a][1,4]benzodiazepine (100 mg, 0.228 mmol), rac-trans-N1,N2-dimethylcyclohexane-1,2-diamine (35.3 μL, 0.228 mmol), sodium iodide (342 mg, 2.28 mmol) and copper(I) iodide (21.8 mg, 114 μmol) was added 1,4-dioxane (10 mL) under Argon. The resulting suspension was heated to 115° C. for 6 days. A further amount of sodium iodide (685 mg, 4.57 mmol) and copper(I) iodide (218 mg, 1.14 mmol) were added and the reaction mixture was stirred for further 2 days. The mixture was diluted with ethyl acetate and the organic layer was washed twice with aqueous ammonia, brine, dried over sodium sulfate and concentrated in vacuo. The crude material was purified by flash column chromatography (silica, methanol in dichloromethane 0-15%), followed by chiral HPLC (Chiracel OD; eluent: 20% (ammonium acetate 0.1 mol in ethanol) in heptane) to afford the (−)-enantiopure (S)-title compound (41.2 mg, 37%) as a white solid. MS: 485.0 ([M+H]$^+$), ESI pos.

Example 103

[(4S)-7-chloro-6-(2,6-difluorophenyl)-4-methyl-8-(trifluoromethyl)-4H-[1,2,4]triazolo[4,3-a][1,4]benzodiazepin-1-yl]methanol

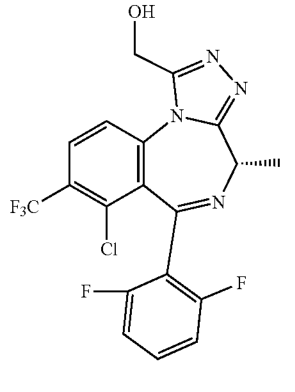 [SMILES: C[C@@H]1N=C(c2c(F)cccc2F)c2c(ccc(C(F)(F)F)c2Cl)-n2c(CO)nnc21]

a) [(4S)-7-chloro-6-(2,6-difluorophenyl-4-methyl-8-(trifluoromethyl)-4H-[1,2,4]triazolo[4,3-a][1,4]benzodiazepin-1-yl]methoxy-triisopropyl-silane In analogy to experiment of example 30 b, (3S)-6-chloro-5-(2,6-difluorophenyl)-3-methyl-7-(trifluoromethyl)-1,3-dihydro-1,4-benzodiazepine-2-thione using 2-triisopropylsilyloxyacetohydrazide was converted into the title compound (300 mg, 33%) which was obtained as a light yellow oil. MS: 599.2 ([M+H]$^+$), ESI pos.

b) [(4S)-7-chloro-6-(2,6-difluorophenyl)-4-methyl-8-(trifluoromethyl)-4H-[1,2,4]triazolo[4,3-a][1,4]benzodiazepin-1-yl]methanol To a solution of [(4S)-7-chloro-6-(2,6-difluorophenyl)-4-methyl-8-(trifluoromethyl)-4H-[1,2,4]triazolo[4,3-a][1,4]benzodiazepin-1-yl]methoxy-triisopropyl-silane (200.0 mg, 0.270 mmol) in tetrahydrofuran (4 mL) was slowly added TBAF (1.0 M in tetrahydrofuran, 0.81 mL, 0.810 mmol). The mixture was stirred at room temperature for 1 h, before being concentrated in vacuo. The residue was purified by flash column chromatography (dichloromethane/methanol 50:1 to 20:1), followed by preparative HPLC (UniSil 3-100 C18 Ultra, 0.225% trifluoroacetic acid in water/acetonitrile) and SFC separation (Daicel Chiralcel OJ, 0.1% ammonia in ethanol) to afford the (−)-enantiopure (S)-title compound (13.6 mg, 10%) as a white solid. MS: 443.0 ([M+H]$^+$), ESI pos.

Example 105

(4R)-7-chloro-6-(2,6-difluorophenyl)-4-(methoxymethyl)-1-methyl-8-(trifluoromethyl)-4H-[1,2,4]triazolo[4,3-a][1,4]benzodiazepine

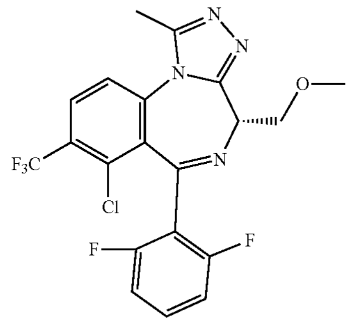 [SMILES: COC[C@@H]1N=C(c2c(F)cccc2F)c2c(ccc(C(F)(F)F)c2Cl)-n2c(C)nnc21]

To an oven-dried vial equipped with a magnetic stir bar and a Teflon septum was added (4R)-8-bromo-7-chloro-6-(2,6-difluorophenyl)-4-(methoxymethyl)-1-methyl-4H-[1,2,4]triazolo[4,3-a][1,4]benzodiazepine (10 mg, 21.4 □mol), sodium carbonate (9.06 mg, 85.5 □mol), $CuBr_2\cdot 2LiBr$ (4.28 μmol), Mes-Umemoto reagent (22 mg, 42.8 □mol), Ir[dFMeppy]$_2$-(4,4'-dCF$_3$bpy)PF$_6$ (56 μg, 0.0535 μmol) and $(Me_3Si)_3SiOH$ (8.5 mg, 32.1 μmol). The vial was then degassed by alternative evacuation and back filling with nitrogen, then degassed acetone (0.2 mL) was added via syringe addition. The reaction mixture was stirred at room temperature for 16 h under irradiation of a blue LED (Kessil lamp 40 W, 420 nm). The vial was opened and the reaction mixture was filtered directly through a plug of celite. The filter cake was rinsed with ethyl acetate (2.0 mL) and the filtrate concentrated in vacuo. The residue was dissolved in ethyl acetate (20 mL) and washed with water and brine (3×15 mL), dried over sodium sulfate, filtered and concentrated in vacuo. The crude material was purified by preparative HPLC (Gemini NX5Y, 0.1% formic acid in water/acetonitrile) to afford the (−)-enantiopure (R)-title compound (3 mg, 30%) as a white solid. MS: 457.2 ([M+H]$^+$), ESI pos.

Example 106

[(4R)-7-chloro-6-(2,6-difluorophenyl)-1-methyl-8-(trifluoromethyl)-4H-[1,2,4]triazlo[4,3-a][1,4]benzodiazepin-4-yl]methanol

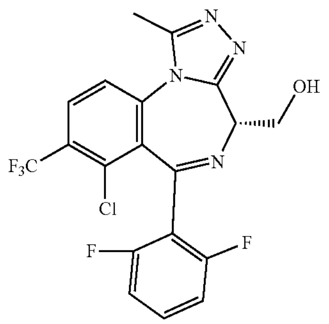 [SMILES: Cc1nnc2n1-c1ccc(C(F)(F)F)c(Cl)c1C(c1c(F)cccc1F)=N[C@H]2CO]

In analogy to experiment of example 105, [(4R)-8-bromo-7-chloro-6-(2,6-difluorophenyl)-1-methyl-4H-[1,2,4]triazolo[4,3-a][1,4]benzodiazepin-4-yl]methanol was converted into the (−)-enantiopure (R)-title compound (9 mg, 31%) which was obtained as a white lyophilized powder. MS: 443.1 ([M+H]$^+$), ESI pos.

Example 107

(4S)-7-chloro-6-(2,6-difluorophenyl)-4-methyl-8-(trifluoromethyl)-4H-[1,2,4]triazolo[4,3-a][1,4]benzodiazepine

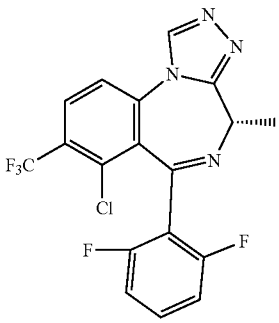 [SMILES: C[C@@H]1N=C(c2c(F)cccc2F)c2c(ccc(C(F)(F)F)c2Cl)-n2cnnc21]

In analogy to experiment of example 105, (4S)-8-bromo-7-chloro-6-(2,6-difluorophenyl)-4-methyl-4H-[1,2,4]triazolo[4,3-a][1,4]benzodiazepine was converted into the (−)-enantiopure (S)-title compound (1 mg, 10%) which was obtained as a white solid. MS: 413.2 ([M+H]$^+$), ESI pos.

Example 108

(4S)-7-chloro-6-(2,6-difluorophenyl)-1-ethyl-4-methyl-8-(trifluoromethyl)-4H-[1,2,4]triazolo[4,3-a][1,4]benzodiazepine

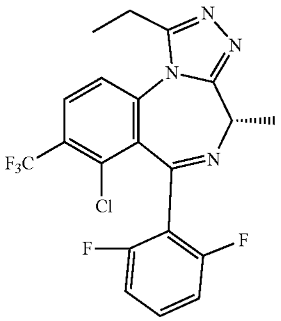 [SMILES: CCc1nnc2n1-c1ccc(C(F)(F)F)c(Cl)c1C(c1c(F)cccc1F)=N[C@H]2C]

In analogy to experiment of example 30 b, (3S)-6-chloro-5-(2,6-difluorophenyl)-3-methyl-7-(trifluoromethyl)-1,3-dihydro-1,4-benzodiazepine-2-thione using propanehydrazide was converted after chiral purification into the (−)-enantiopure (S)-title compound (16.4 mg, 13%) which was obtained as a white solid. MS: 444.1 ([M+H]$^+$), ESI pos.

Example 109

(4S)-7-chloro-6-(2,6-difluorophenyl)-8-ethyl-1,4-dimethyl-4H-[1,2,4]triazolo[4,3-a][1,4]benzodiazepine

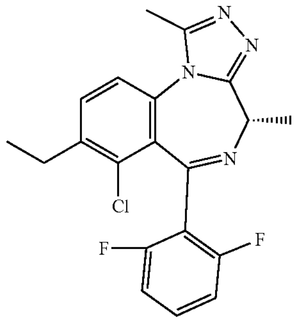 [SMILES: CCc1ccc2c(c1Cl)C(c1c(F)cccc1F)=N[C@@H](C)c1nnc(C)n1-2]

To a solution of (4S)-8-bromo-7-chloro-6-(2,6-difluorophenyl)-1,4-dimethyl-4H-[1,2,4]triazolo[4,3-a][1,4]benzodiazepine (120 mg, 0.274 mmol) and [1,1'-bis(diphenylphosphino)ferrocene]dichloropalladium(II) $CH_2Cl_2$ (4.5 mg, 5.5 μmol) in dry tetrahydrofuran (1.2 mL) at 0° C. was added dropwise diethylzinc (1.0 M in heptane, 0.823 mL, 0.823 mmol). The reaction was allowed to warm to room temperature, before being heated to 55° C. for 15 h. The reaction mixture was poured into water and extracted twice with ethyl acetate. The combined organic layers were washed with water and brine, dried over sodium sulfate, filtered and concentrated in vacuo. The crude material was purified by preparative HPLC (Gemini NX, 0.1% triethylamine in water/methanol), followed by chiral HPLC (Reprosil Chiral NR, 0.01 M ammonium acetate in ethanol, 30%) to afford the (−)-enantiopure (S)-title compound (31.7 mg, 30%) as a white powder. MS: 387.3 ([M+H]$^+$), ESI pos.

Reference Compounds

RE-A 8-bromo-6-(2,6-difluorophenyl)-1-methyl-4H-[1,2,4]triazolo[4,3-a][1,4]benzodiazepine

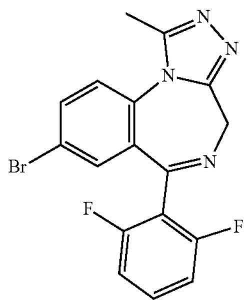 [SMILES: Cc1nnc2n1-c1ccc(Br)cc1C(c1c(F)cccc1F)=NC2]

a) N-[2-(2,6-difluorobenzoyl)phenyl]acetamide

In analogy to experiment of building block A b, 2-methyl-3,1-benzoxazin-4-one (CAS #525-76-8) was converted into the title compound (40 g, 80%) which was obtained as a light yellow solid. MS: 276.2 ([M+H]$^+$), ESI pos.

b) (2-aminophenyl)-(2,6-difluorophenyl)methanone

In analogy to experiment of building block A c, N-[2-(2,6-difluorobenzoyl)phenyl]acetamide was converted into the title compound (19.5 g, 75%) which was obtained as a yellow solid. MS: 234.1 ([M+H]$^+$), ESI pos.

c) (2-amino-5-bromo-phenyl)-(2,6-difluorophenyl)methanone

To a solution of (2-aminophenyl)-(2,6-difluorophenyl)methanone (5.00 g, 21.4 mmol) in dichloromethane (50 mL) was added portionwise N-bromosuccinimide (4.02 g, 22.51 mmol) at −15° C. The reaction mixture was stirred at −15° C. for 1 h, till complete consumption of starting material (as judged by LCMS analysis). The mixture was concentrated under reduced pressure and the resulting residue purified by preparative HPLC (Shim-pack C18, 0.225% trifluoroacetic acid in water/acetonitrile). The combined fractions were diluted with saturate aqueous sodium bicarbonate and extracted with ethyl acetate (3×200 mL). The organic phase was washed with brine (2×100 mL), dried ($Na_2SO_4$) and concentrated in vacuo to afford the title compound (4.44 g, 66%) as a yellow solid. MS: 311.9 ([{$^{79}$Br}M+H]$^+$), 314.0 ([{$^{81}$Br}M+H]$^+$), ESI pos.

d) 7-bromo-5-(2,6-difluorophenyl-1,3-dihydro-1,4-benzodiazepin-2-one

In analogy to experiment of building block A e, (2-amino-5-bromo-phenyl)-(2,6-difluorophenyl)methanone was converted into the title compound (300 mg, 13%) which was obtained as a yellow solid. MS: 351.0 ([{$^{79}$Br}M+H]$^+$), 353.0 ([{$^{81}$Br}M+H]$^+$), ESI pos.

e) 7-bromo-5-(2,6-difluorophenyl)-1,3-dihydro-1,4-benzodiazepine-2-thione

In analogy to experiment of example 30 a, 7-bromo-5-(2,6-difluorophenyl)-1,3-dihydro-1,4-benzodiazepin-2-one was converted into the title compound (310 mg, 92%) which was obtained as a yellow solid. The crude was used as such in the following step without further characterization.

f) 8-bromo-6-(2,6-difluorophenyl-1-methyl-4H-[1,2,4]triazolo[4,3-a][1,4]benzodiazepine In analogy to experiment of example 30 b, 7-bromo-5-(2,6-difluorophenyl)-1,3-dihydro-1,4-benzodiazepine-2-thione using acetohydrazide was converted into the title compound (5.1 mg, 4%) which was obtained as a white solid. MS: 389.0 ([{$^{79}$Br}M+H]$^+$), 391.0 ([{$^{81}$Br}M+H]$^+$), ESI pos.

RE-B 6-(2,6-difluorophenyl)-1-methyl-8-(trifluoromethyl)-4H-[1,2,4]triazolo[4,3-a][1,4]benzodiazepine

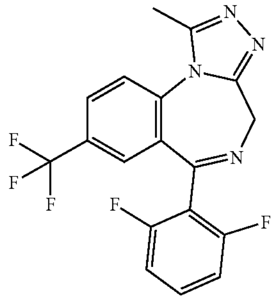 [SMILES: Cc1nnc2n1-c1ccc(C(F)(F)F)cc1C(c1c(F)cccc1F)=NC2]

a) (2-amino-5-iodo-phenyl)-(2,6-difluorophenyl)methanone

To a solution of (2-aminophenyl)-(2,6-difluorophenyl)methanone (1.6 g, 6.86 mmol) in DMF (15 mL) was added portionwise N-iodosuccinimide (1.62 g, 7.2 mmol). The reaction mixture was stirred at 20° C. for 16 h, before being diluted with water (20 mL). The mixture was extracted with ethyl acetate (3×20 mL), then the combined organic extracts were washed with brine (2×10 mL), dried ($Na_2SO_4$) and concentrated in vacuo. The residue was purified by flash column chromatography (petroleum ether/ethyl acetate, 10:1 to 5:1) to afford the title compound (2.0 g, 81%) as a yellow solid. MS: 360.0 ([M+H]$^+$), ESI pos.

b) 5-(2,6-difluorophenyl)-7-iodo-1,3-dihydro-1,4-benzodiazepin-2-one

In analogy to experiment of building block A e, (2-amino-5-iodo-phenyl)-(2,6-difluorophenyl)methanone was converted into the title compound (650 mg, 12%) which was obtained as a yellow solid. MS: 399.0 ([M+H]$^+$), ESI pos.

c) 5-(2,6-difluorophenyl)-7-iodo-1,3-dihydro-1,4-benzodiazepine-2-thione

In analogy to experiment of example 30 a, 5-(2,6-difluorophenyl)-7-iodo-1,3-dihydro-1,4-benzodiazepin-2-one was converted into the title compound (200 mg, 82%) which was obtained as a yellow solid. MS: 414.9 ([M+H]$^+$), ESI pos.

d) 5-(2,6-difluorophenyl)-7-iodo-1,3-dihydro-1,4-benzodiazepin-2-one hydrazone

In analogy to experiment of example 64 a, 5-(2,6-difluorophenyl)-7-iodo-1,3-dihydro-1,4-benzodiazepine-2-thione was converted into the title compound (220 mg, 98%) which was obtained as a yellow solid. MS: 413.0 ([M+H]$^+$), ESI pos.

e) 6-(2,6-difluorophenyl)-8-iodo-1-methyl-4H-[1,2,4]triazolo[4,3-a][1,4]benzodiazepine In analogy to experiment of example 98 c, 5-(2,6-difluorophenyl)-7-iodo-1,3-dihydro-1,4-benzodiazepin-2-one hydrazone was converted into the title compound (150 mg, 64%) which was obtained as a yellow solid. MS: 437.0 ([M+H]$^+$), ESI pos.

f) 6-(2,6-difluorophenyl-1-methyl-8-(trifluoromethyl)-4H-[1,2,4]triazolo[4,3-a][1,4]benzodiazepine In analogy to experiment of example 92 a, 6-(2,6-difluorophenyl)-8-iodo-1-methyl-4H-[1,2,4]triazolo[4,3-a][1,4]benzodiazepine was converted into the title compound (5 mg, 6%) which was obtained as a white solid. MS: 379.0 ([M+H]$^+$), ESI pos.

RE-C 6-(2,6-difluorophenyl)-1-methyl-4H-[1,2,4]triazolo[4,3-a][1,4]benzodiazepine

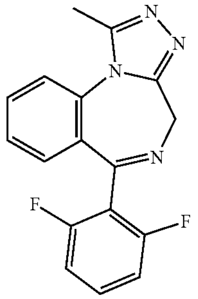 [SMILES: Cc1nnc2n1-c1ccccc1C(c1c(F)cccc1F)=NC2]

To a stirred solution of 8-bromo-6-(2,6-difluorophenyl)-1-methyl-4H-[1,2,4]triazolo[4,3-a][1,4]benzodiazepine (30 mg, 0.08 mmol) in methanol (0.5 mL) was added 10 wt. % Pd/C (2.5 mg, 2.4 μmol) and the resulting black suspension was purged by evacuation and then back filled with a stream of hydrogen (balloon) for three times. The mixture was stirred for 16 hours at room temperature under hydrogen atmosphere then filtered through a pad of dicalite. The filter cake was rinsed with methanol and the filtrate was concentrated in vacuo. The residue was purified by preparative HPLC (Phenomenex Gemini-NX C18, 0.1% trifluoroacetic acid in water/acetonitrile) followed by preparative TLC (silica, dichloromethane/methanol, 20:1) to obtain the title compound (5 mg, 20%) as a white solid. MS: 276.2 ([M+H]$^+$), ESI pos.

RE-D (4S)-7-chloro-6-(2,6-difluorophenyl)-1,4-dimethyl-4H-[1,2,4]triazolo[4,3-a][1,4]benzodiazepine

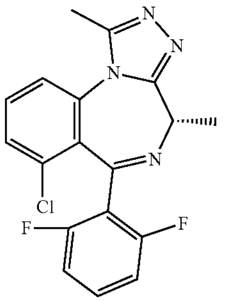 [SMILES: Cc1nnc2n1-c1cccc(Cl)c1C(c1c(F)cccc1F)=N[C@H]2C]

In analogy to experiment of reference compound RE-C, (4S)-8-bromo-7-chloro-6-(2,6-difluorophenyl)-1,4-dimethyl-4H-[1,2,4]triazolo[4,3-a][1,4]benzodiazepine was converted into the title compound (2 mg, 15%) which was obtained as a white solid. MS: 359.1 ([M+H]$^+$), ESI pos.

The invention claimed is:

1. A method for treating a gamma-aminobutyric acid A gamma1 (GABA$_A$ γ1) receptor related disease or condition in a subject, wherein the method comprises administering to the subject in need thereof an effective amount of a compound selected from the group consisting of:

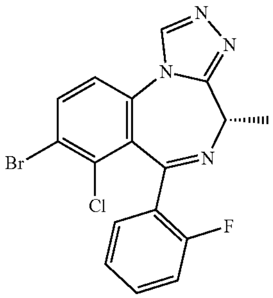

,

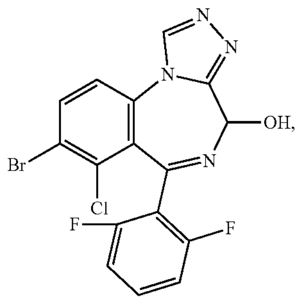

,

-continued
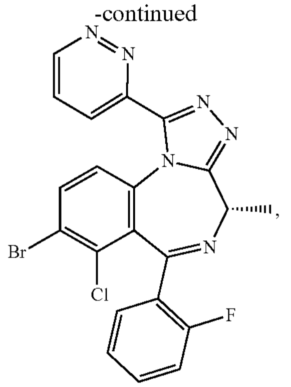
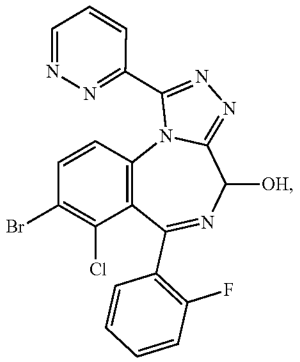
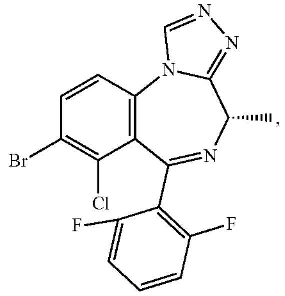
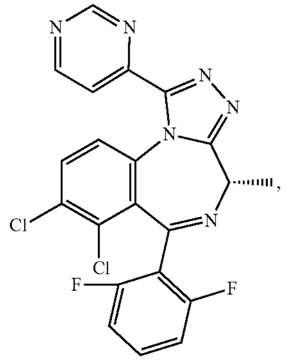
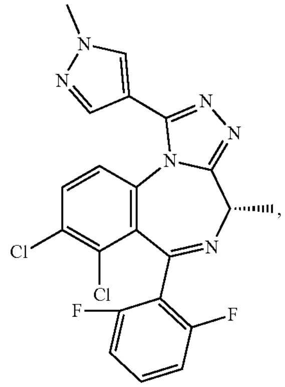
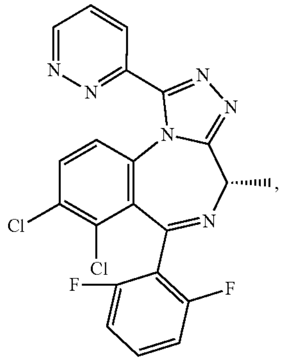
-continued
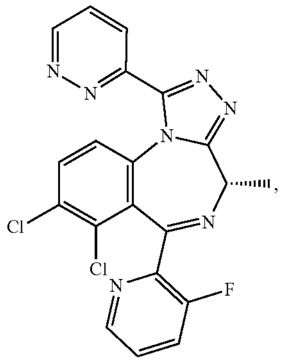
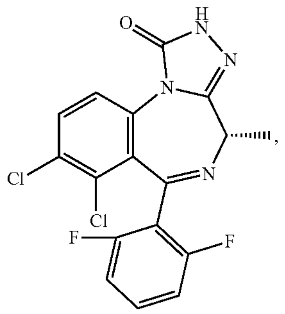
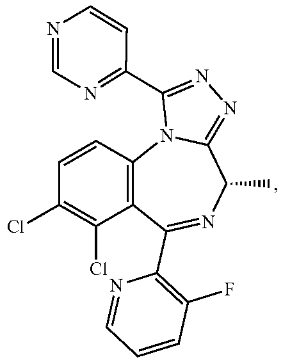
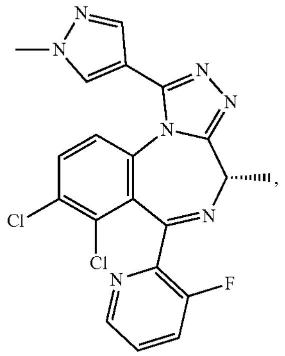
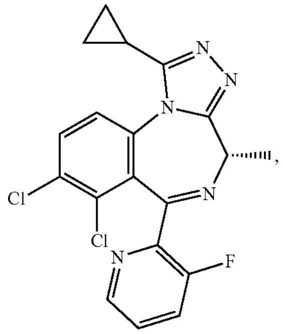
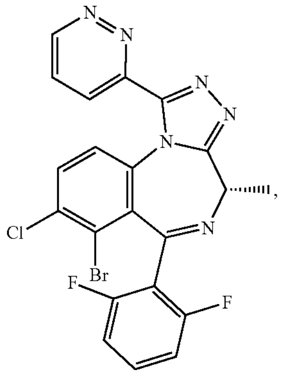
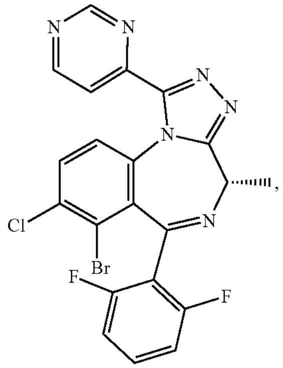
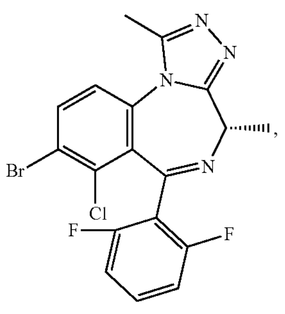

-continued
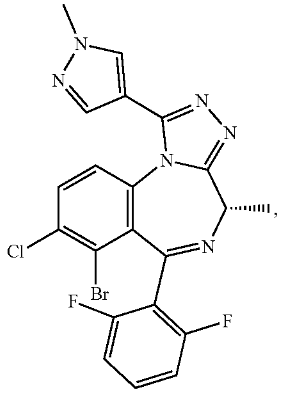,
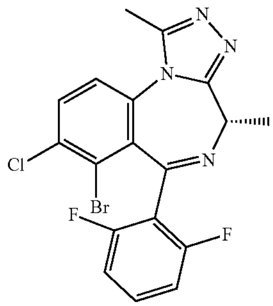,
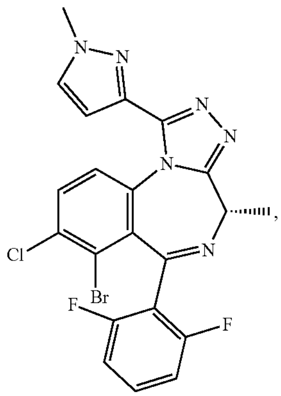,
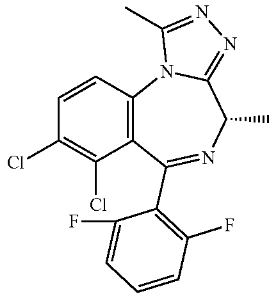,
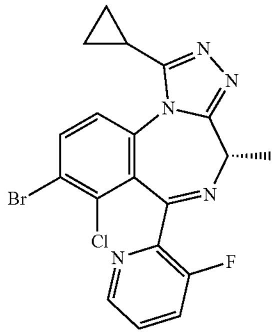,
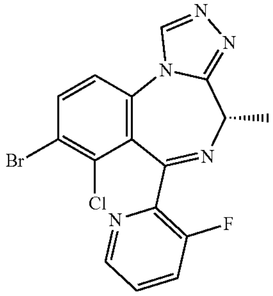,
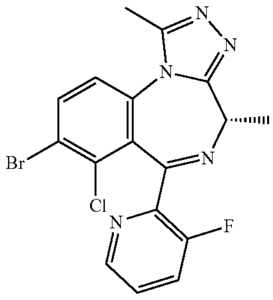,
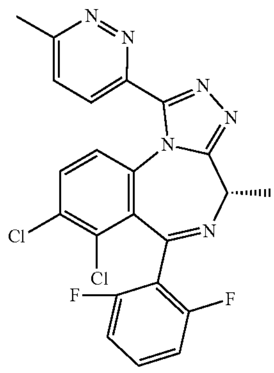,
-continued
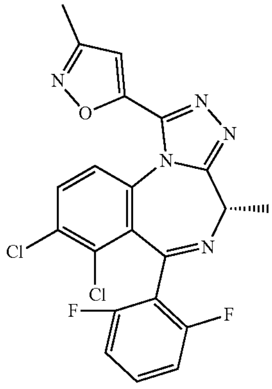,
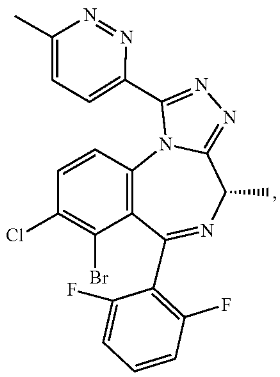,
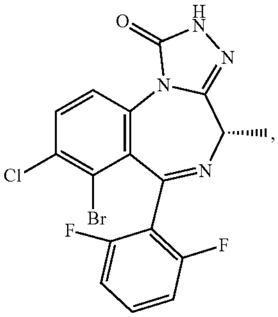,
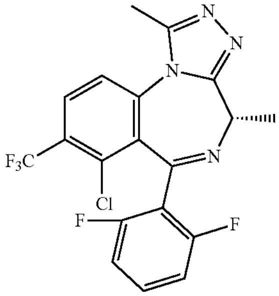,
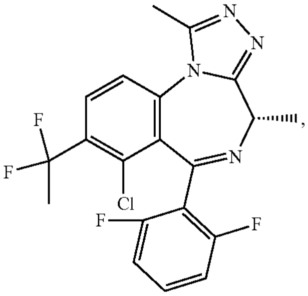,
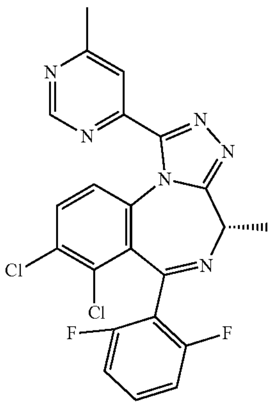,
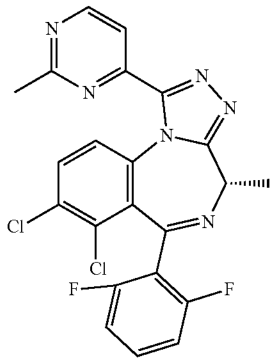, -continued
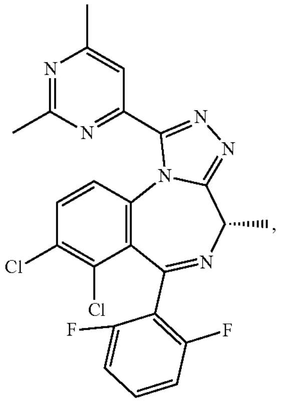
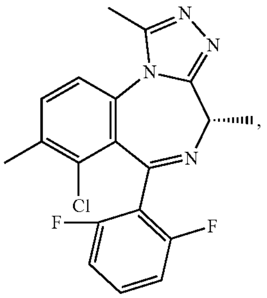
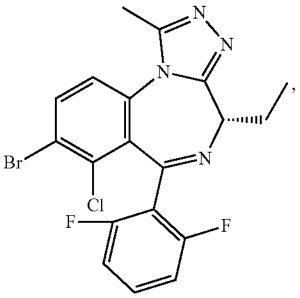
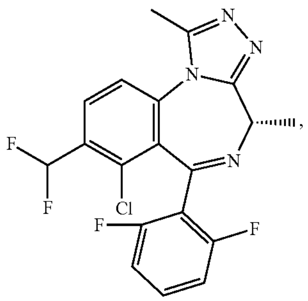
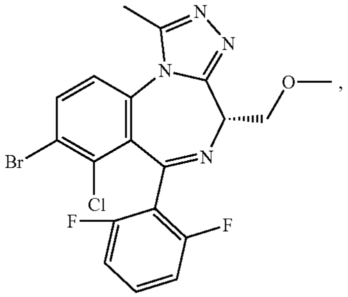
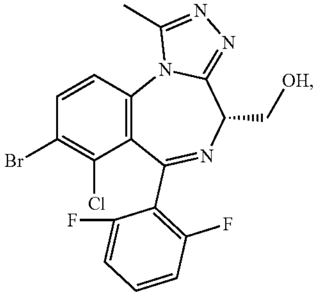
-continued
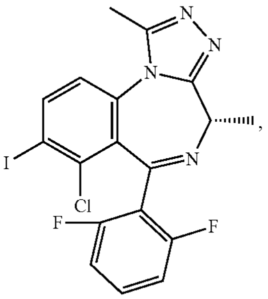
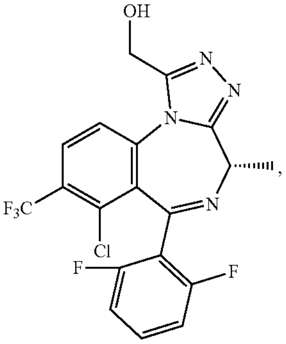
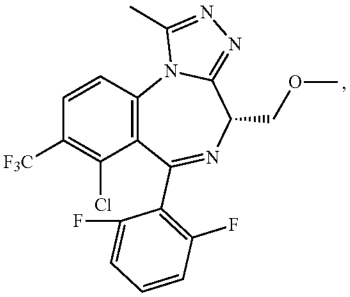
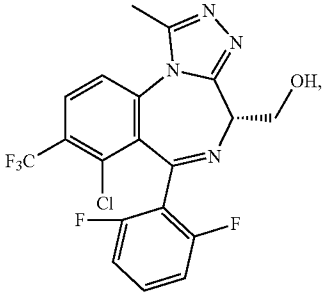
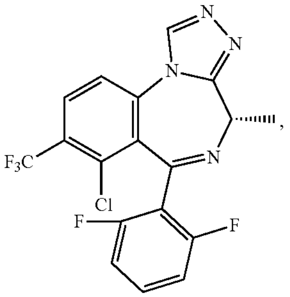
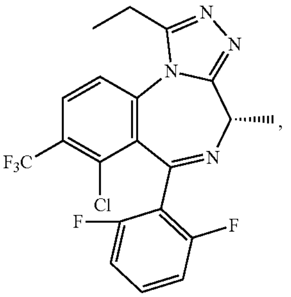 and -continued

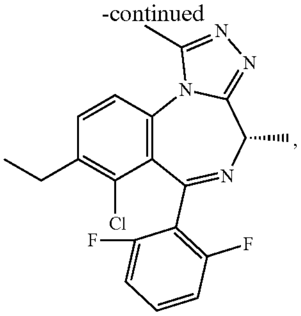

or a pharmaceutically acceptable salt thereof;

wherein the gamma-aminobutyric acid A gamma1 ($GABA_A$ γ1) receptor related disease or condition is selected from the group consisting of anxiety, autism spectrum disorder, fragile-X disorder, generalized anxiety disorder, post-traumatic stress disorder, Rett syndrome, and social anxiety disorder.

2. The method of claim 1, wherein the gamma-aminobutyric acid A gamma1 ($GABA_A$ γ1) receptor related disease or condition is anxiety.

3. The method of claim 1, wherein the gamma-aminobutyric acid A gamma1 ($GABA_A$ γ1) receptor related disease or condition is selected from the group consisting of autism spectrum disorder, fragile-X disorder, post-traumatic stress disorder, and Rett syndrome.

4. The method of claim 1, wherein the gamma-aminobutyric acid A gamma1 ($GABA_A$ γ1) receptor related disease or condition is autism spectrum disorder.

5. The method of claim 1, wherein the gamma-aminobutyric acid A gamma1 ($GABA_A$ γ1) receptor related disease or condition is fragile-X disorder.

6. The method of claim 1, wherein the gamma-aminobutyric acid A gamma1 ($GABA_A$ γ1) receptor related disease or condition is generalized anxiety disorder.

7. The method of claim 1, wherein the gamma-aminobutyric acid A gamma1 ($GABA_A$ γ1) receptor related disease or condition is post-traumatic stress disorder.

8. The method of claim 1, wherein the gamma-aminobutyric acid A gamma1 ($GABA_A$ γ1) receptor related disease or condition is Rett syndrome.

9. The method of claim 1, wherein the gamma-aminobutyric acid A gamma1 ($GABA_A$ γ1) receptor related disease or condition is social anxiety disorder.

10. The method of claim 1, wherein the compound is:

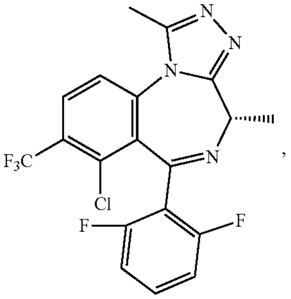 [SMILES: Cc1nnc2n1-c1ccc(C(F)(F)F)c(Cl)c1C(c1c(F)cccc1F)=N[C@H]2C]

or a pharmaceutically acceptable salt thereof.

11. The method of claim 10, wherein the gamma-aminobutyric acid A gamma1 ($GABA_A$ γ1) receptor related disease or condition is anxiety.

12. The method of claim 10, wherein the gamma-aminobutyric acid A gamma1 ($GABA_A$ γ1) receptor related disease or condition is selected from the group consisting of autism spectrum disorder, fragile-X disorder, post-traumatic stress disorder, and Rett syndrome.

13. The method of claim 10, wherein the gamma-aminobutyric acid A gamma1 ($GABA_A$ γ1) receptor related disease or condition is autism spectrum disorder.

14. The method of claim 10, wherein the gamma-aminobutyric acid A gamma1 ($GABA_A$ γ1) receptor related disease or condition is fragile-X disorder.

15. The method of claim 10, wherein the gamma-aminobutyric acid A gamma1 ($GABA_A$ γ1) receptor related disease or condition is generalized anxiety disorder.

16. The method of claim 2, wherein the gamma-aminobutyric acid A gamma1 ($GABA_A$ γ1) receptor related disease or condition is post-traumatic stress disorder.

17. The method of claim 10, wherein the gamma-aminobutyric acid A gamma1 ($GABA_A$ γ1) receptor related disease or condition is Rett syndrome.

18. The method of claim 10, wherein the gamma-aminobutyric acid A gamma1 ($GABA_A$ γ1) receptor related disease or condition is social anxiety disorder.

* * * * *